US009097713B2

(12) United States Patent
Dye et al.

(10) Patent No.: US 9,097,713 B2
(45) Date of Patent: Aug. 4, 2015

(54) MONOCLONAL ANTIBODIES AGAINST GLYCOPROTEIN OF EBOLA SUDAN BONIFACE VIRUS

(75) Inventors: John M. Dye, Frederick, MD (US); Ana I. Kuehne, Frederick, MD (US); Shawn B. Guest, Frederick, MD (US)

(73) Assignee: THE UNITED STATES OF AMERICA AS REPRESENTED BY THE SECRETARY OF THE ARMY ON BEHALF OF USAMRMC, Washington, DC (US)

( * ) Notice: Subject to any disclaimer, the term of this patent is extended or adjusted under 35 U.S.C. 154(b) by 203 days.

(21) Appl. No.: 13/393,622

(22) PCT Filed: Sep. 1, 2010

(86) PCT No.: PCT/US2010/047586
§ 371 (c)(1),
(2), (4) Date: Mar. 1, 2012

(87) PCT Pub. No.: WO2011/071574
PCT Pub. Date: Jun. 16, 2011

(65) Prior Publication Data
US 2012/0164153 A1   Jun. 28, 2012

Related U.S. Application Data

(60) Provisional application No. 61/239,166, filed on Sep. 2, 2009, provisional application No. 61/290,725, filed on Dec. 29, 2009.

(51) Int. Cl.
*G01N 33/569* (2006.01)
*C07K 16/10* (2006.01)
*A61K 39/00* (2006.01)

(52) U.S. Cl.
CPC .......... *G01N 33/56983* (2013.01); *C07K 16/10* (2013.01); *A61K 2039/505* (2013.01); *C07K 2317/34* (2013.01); *C07K 2317/76* (2013.01); *C12N 2760/14111* (2013.01); *G01N 2333/08* (2013.01)

(58) Field of Classification Search
CPC .................... G01N 33/56983; G01N 2333/08; C07K 16/10; C07K 2317/34; C07K 2317/76; A61K 2039/505
See application file for complete search history.

(56) References Cited

U.S. PATENT DOCUMENTS

| 6,630,144 | B1 | 10/2003 | Hart et al. |
| 6,875,433 | B2 | 4/2005 | Hart et al. |
| 6,984,504 | B2 | 1/2006 | Hart et al. |
| 7,335,356 | B2 | 2/2008 | Hart et al. |
| 2002/0164582 | A1 | 11/2002 | Hart et al. |
| 2003/0224015 | A1 | 12/2003 | Hart et al. |
| 2004/0053865 | A1 | 3/2004 | Hart et al. |
| 2004/0146859 | A1 | 7/2004 | Hart et al. |

FOREIGN PATENT DOCUMENTS

WO    96/37616    11/1996

OTHER PUBLICATIONS

TheiBen, G., 2002, Secret life of genes, Nature 415:741.*
Choi, K. H., et al., 2004, Design, expression, and purification of a Flaviviridae polymerase using a high-throughput approach to facilitate crystal structure determination, Prot. Sci. 13:2685-2692.*
Li, Yi., et al., 1996, The I binding specificity of human VH4-34 (VH4-21) encoded by antibodies is determined by both VH framework region 1 and complementarity determining region 3, J. Mol. Biol. 256:577-589.*
Winkler, K., et al., 2000, Changing the antigen binding specificity by single point mutations of an anti-p24 (HIV-1) antibody, J. Immunol. 165:4505-4514.*
S.V.S. Kashmiri et al., "Development of a minimally immunogenic variant of humanized anti-carcinoma monoclonal antibody CC49," Critical Reviews in Oncology/Hematology, vol. 38, 2001, pp. 3-16.
J. Pettitt et al., "Therapeutic Intervention of Ebola Virus Infection in Rhesus Macaques with the MB-003 Monoclonal Antibody Cocktail," Science Translational Medicine, vol. 5, Issue 199 199ra113, Aug. 21, 2013, pp. 1-6.
J. Dye et al., "Sudan Ebolavirus Specific Murine Monoclonal Antibodies," presented at 3rd Annual International Filovirus Symposium, Gabon, Africa (Mar. 26-28, 2008).
Ana Kuehne et al., "Sudan Ebolavirus Specific Murine Monoclonal Antibodies," presented at ASM Biodefense and Emerging Diseases Research Meeting, Baltimore, MD (Feb. 22-25, 2009).
International Search Report issued on Aug. 18, 2011 in International Application No. PCT/US2010/047586 filed Sep. 1, 2010.

* cited by examiner

*Primary Examiner* — Jeffrey Parkin
(74) *Attorney, Agent, or Firm* — Drinker Biddle & Reath LLP

(57) ABSTRACT

We disclose Ebola Sudan Boniface virus GP Monoclonal antibodies, epitopes recognized by these monoclonal antibodies, and the sequences of the variable regions of some of these antibodies. Also provided are mixtures of antibodies of the present invention, as well as methods of using individual antibodies or mixtures thereof for the detection, prevention, and/or therapeutic treatment of Ebola Sudan Boniface virus infections in vitro and in vivo.

8 Claims, 23 Drawing Sheets

Table 1. OVERVIEW OF MURINE ANTIBODIES GENERATED AGAINST SUDAN BONIFACE GLYCOPROTEIN.

| Hybridoma | Isotype[1] | Western Blot[2] | Specificity by ELISA[3] | Specificity for Gulu[4] | Specificity for Boniface[4] | Specificity for Zaire[4] | Specificity for Lassa[4] | Linear Epitope by SPOTS membrane and sequence[5] |
|---|---|---|---|---|---|---|---|---|
| 3C10 | IgG2a | positive | Sudan | positive | positive | negative | negative | Bon-LHVPEGETT, Gulu-LHIPEGETT |
| 16F6 | IgG1 | positive | Sudan + Zaire | positive | positive | negative | negative | No binding to either Sudan or Zaire |
| 16H11 | IgG1 | positive | Sudan | N/A | N/A | N/A | N/A | No binding to Sudan |
| 17F6 | IgG2a | positive | Sudan | positive | positive | negative | negative | Bon-LHVPEGETT, Gulu-LHIPEGETT |
| 19B3 | IgG1 | positive | Sudan | ? | Negative | negative | negative | Bon-LHVPEGETT, Gulu-LHIPEGETT |
| 19E4 | IgG1 | positive | Sudan | N/A | N/A | N/A | N/A | Not Done |
| 19F10 | IgG1 | positive | Sudan | negative | negative | negative | negative | No binding to Sudan |
| 1A1 | IgG1 | | Sudan | | | | | |
| 1G1 | IgG1 | | Sudan | | | | | |
| 5G2 | IgG1 | | Sudan | | | | | |
| 6G12 | IgG1 | | Sudan | | | | | |
| 6H1 | IgG1 | | Sudan + Zaire | | | | | |
| 8C10 | IgG1 | | Sudan + Zaire | | | | | |
| 3F10 | IgG1 | | Sudan + Zaire | | | | | |
| 5A11 | IgM+IgG3 | | Sudan + Zaire | | | | | |
| 5B4 | IgG1 | | Sudan + Zaire | | | | | |
| 8E9 | IgM+IgG2b | | Sudan + Zaire | | | | | |
| 5G10 | IgG2a | | Sudan | | | | | |

1. Isotype determined by ISOSTRIP assay. 2. Western blot against whole irradiated Ebola Sudan. 3. ELISA against whole irradiated Ebola Sudan Boniface and Ebola Zaire. 4. Specificity against Gulu, Boniface, Zaire and Lassa determined by ability to bind VERO cells after infection with VRP expressing the given protein. 5. Linear epitope determined by capacity to bind overlapping 13-mer-synthetic peptides bound to nitrocellulose wells and detection.

FIG. 7

Table  Overview Of Murine Antibodies Generated Against Sudan Boniface Glycoprotein

| Hybridoma | Isotype[1] |

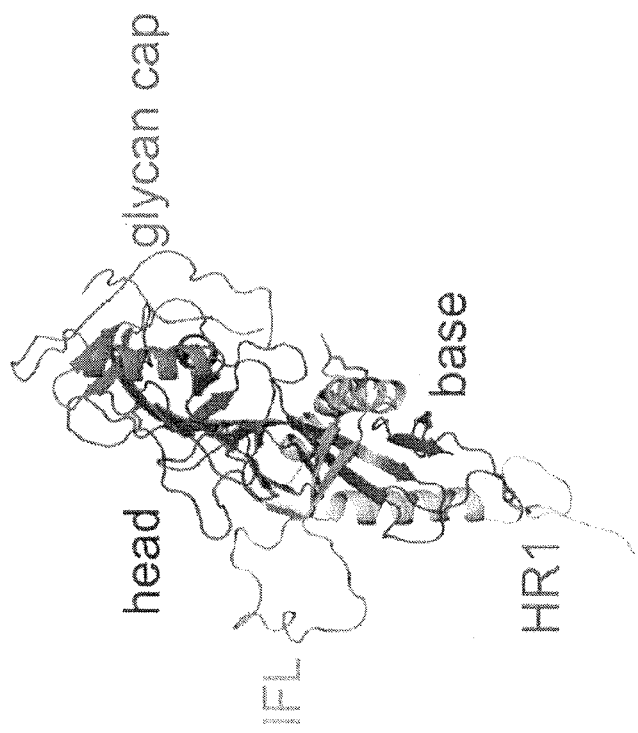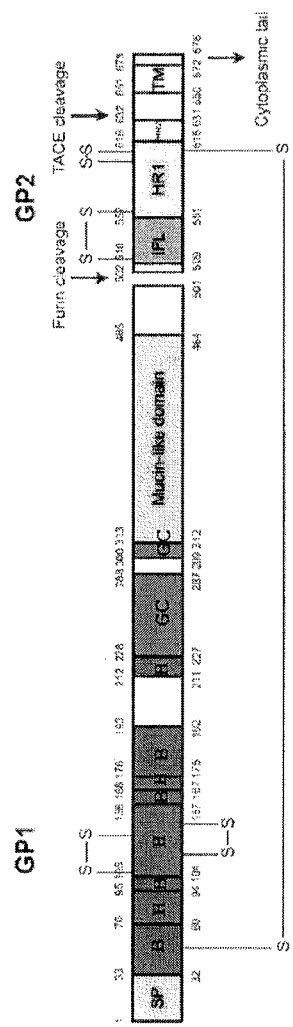
FIG. 18

SEQUENCE LISTING

```
<160> NUMBER OF SEQ ID NOS: 25

<210> SEQ ID NO 1
<211> LENGTH: 451
<212> TYPE: DNA
<213> ORGANISM: artificial
<220> FEATURE:
<223> OTHER INFORMATION: Synthetic heavy chain of Mab 16H11 DNA Sequence

<400> SEQUENCE: 1
tggagctggg tcatcctctt cctgttttca gtaactgcag gtgtccactc ccaggtccag      60
cttcagcagt ctggggctga actggcaaaa cctggggcct cagtgaagat gtcctgcaag     120
gcttctggct acacctttac tagctactgg atgcactggg taaaacagag gcctggacag     180
ggtctggaat ggattggata cattaatcct agcactggtt atactgagta caatcagaag     240
ttcaaggaca aggccacatt gactgcagac aaatcctcca ccacagccta catgcaactg     300
agcagcctga catctgagga ctctgcagtc tattactgtg caagatcggg tgcctattac     360
tacggtagta gcccctactt tgactactgg ggccaaggca ccactctcac agtctcctca     420
gccaaaacga cacccccatc cgtttatcca c                                    451

<210> SEQ ID NO 2
<211> LENGTH: 150
<212> TYPE: PRT
<213> ORGANISM: artificial
<220> FEATURE:
<223> OTHER INFORMATION: Synthetic heavy chain of Mab 16H11 amino acid
      Sequence

<400> SEQUENCE: 2

Trp Ser Trp Val Ile Leu Phe Leu Phe Ser Val Thr Ala Gly Val His
1               5                   10                  15

Ser Gln Val Gln Leu Gln Gln Ser Gly Ala Glu Leu Ala Lys Pro Gly
            20                  25                  30

Ala Ser Val Lys Met Ser Cys Lys Ala Ser Gly Tyr Thr Phe Thr Ser
        35                  40                  45

Tyr Trp Met His Trp Val Lys Gln Arg Pro Gly Gln Gly Leu Glu Trp
    50                  55                  60

Ile Gly Tyr Ile Asn Pro Ser Thr Gly Tyr Thr Glu Tyr Asn Gln Lys
65                  70                  75                  80

Phe Lys Asp Lys Ala Thr Leu Thr Ala Asp Lys Ser Ser Thr Thr Ala
                85                  90                  95

Tyr Met Gln Leu Ser Ser Leu Thr Ser Glu Asp Ser Ala Val Tyr Tyr
            100                 105                 110

Cys Ala Arg Ser Gly Ala Tyr Tyr Tyr Gly Ser Ser Pro Tyr Phe Asp
        115                 120                 125
```

Tyr Trp Gly Gln Gly Thr Thr Leu Thr Val Ser Ser Ala Lys Thr Thr
130                 135                 140

Pro Pro Ser Val Tyr Pro
145                 150

<210> SEQ ID NO 3
<211> LENGTH: 452
<212> TYPE: DNA
<213> ORGANISM: artificial
<220> FEATURE:
<223> OTHER INFORMATION: Synthetic heavy chain of Mab 19B3 DNA Sequence

<400> SEQUENCE: 3
gaattcatgg aatggagctg ggtcatcctc ttcctcctgt cagtaactgc aggtgtccac    60
tcccaggttc agctgcagca gtctggagct gagctgatga agcctggggc ctcagtgaag    120
atatcctgca aggctactgg ctacacattc agtagctact ggatagagtg ggtaaagcag    180
aggcctggac atggccttga gtggattgga gagattttac ctggaagtgg tagtactaac    240
tacaatgaga agttcaaggg caaggccaca ttcactgcag atacatcctc caacacagcc    300
tacatgcaac tcagcagcct gacatctgag gactctgccg tctattactg tgcaagaaac    360
tatgcttact ggggccaagg gactctggtc actgtctctg cagccaaaac gacaccccca    420
tccgtttatc cattggcccc tggaagcttg gg                                  452

<210> SEQ ID NO 4
<211> LENGTH: 150
<212> TYPE: PRT
<213> ORGANISM: artificial
<220> FEATURE:
<223> OTHER INFORMATION: Synthetic heavy chain of Mab 19B3 amino acid
      Sequence

<400> SEQUENCE: 4

Glu Phe Met Glu Trp Ser Trp Val Ile Leu Phe Leu Leu Ser Val Thr
1               5                   10                  15

Ala Gly Val His Ser Gln Val Gln Leu Gln Gln Ser Gly Ala Glu Leu
                20                  25                  30

Met Lys Pro Gly Ala Ser Val Lys Ile Ser Cys Lys Ala Thr Gly Tyr
            35                  40                  45

Thr Phe Ser Ser Tyr Trp Ile Glu Trp Val Lys Gln Arg Pro Gly His
        50                  55                  60

Gly Leu Glu Trp Ile Gly Glu Ile Leu Pro Gly Ser Gly Ser Thr Asn
65                  70                  75                  80

Tyr Asn Glu Lys Phe Lys Gly Lys Ala Thr Phe Thr Ala Asp Thr Ser
                85                  90                  95

Ser Asn Thr Ala Tyr Met Gln Leu Ser Ser Leu Thr Ser Glu Asp Ser
            100                 105                 110

Ala Val Tyr Tyr Cys Ala Arg Asn Tyr Ala Tyr Trp Gly Gln Gly Thr
        115                 120                 125

Leu Val Thr Val Ser Ala Ala Lys Thr Thr Pro Pro Ser Val Tyr Pro
130                 135                 140

Leu Ala Pro Gly Ser Leu
145                 150

<210> SEQ ID NO 5
<211> LENGTH: 428
<212> TYPE: DNA
<213> ORGANISM: Artificial Sequence
<220> FEATURE:

<223> OTHER INFORMATION: Synthetic heavy chain of Mab 17F6 DNA Sequence

<400> SEQUENCE: 5

```
gtcgttcctg gtatcctgtc tgatgtgcag cttcaggagt caggacctgg tctggtgaaa      60
ccttctcaga cagtgtccct cacctgcact gtcactggca tctccatcac cgctggaaat     120
tacagatgga gctggatccg ggagtttcca ggaaacaaac tggagtggat agggaacata     180
tactacagtg gtaccattgc ctacaatcca tctctcacaa gtcgaaccgs catcactaga     240
gacagytcca agaaccaatt cttcctggaa atgaactctt tgactgctga agacacagcc     300
acatactact gtgcacgaga tcggggatgg ttactacttg actactgggg ccaaggcacc     360
actctcacag tctcctcaga aaaacaacag ccccatccgt ttatccattg gcccctggaa     420
gcttggga                                                              428
```

<210> SEQ ID NO 6
<211> LENGTH: 142
<212> TYPE: PRT
<213> ORGANISM: artificial
<220> FEATURE:
<223> OTHER INFORMATION: Synthetic heavy chain of Mab 17F6 amino acid
      Sequence
<220> FEATURE:
<221> NAME/KEY: misc_feature
<222> LOCATION: (77)..(77)
<223> OTHER INFORMATION: Xaa can be any naturally occurring amino acid

<400> SEQUENCE: 6

```
Val Val Pro Gly Ile Leu Ser Asp Val Gln Leu Gln Glu Ser Gly Pro
1               5                   10                  15

Gly Leu Val Lys Pro Ser Gln Thr Val Ser Leu Thr Cys Thr Val Thr
            20                  25                  30

Gly Ile Ser Ile Thr Ala Gly Asn Tyr Arg Trp Ser Trp Ile Arg Glu
        35                  40                  45

Phe Pro Gly Asn Lys Leu Glu Trp Ile Gly Asn Ile Tyr Tyr Ser Gly
    50                  55                  60

Thr Ile Ala Tyr Asn Pro Ser Leu Thr Ser Arg Thr Xaa Ile Thr Arg
65                  70                  75                  80

Asp Ser Ser Lys Asn Gln Phe Phe Leu Glu Met Asn Ser Leu Thr Ala
                85                  90                  95

Glu Asp Thr Ala Thr Tyr Tyr Cys Ala Arg Asp Arg Gly Trp Leu Leu
            100                 105                 110

Leu Asp Tyr Trp Gly Gln Gly Thr Thr Leu Thr Val Ser Ser Glu Lys
        115                 120                 125

Gln Gln Pro His Pro Phe Ile His Trp Pro Leu Glu Ala Trp
    130                 135                 140
```

<210> SEQ ID NO 7
<211> LENGTH: 473
<212> TYPE: DNA
<213> ORGANISM: artificial
<220> FEATURE:
<223> OTHER INFORMATION: Synthetic heavy chain of Mab 16F6 DNA Sequence

<400> SEQUENCE: 7

```
actagtcgac atggactcca ggctcaattt agttttcctt gtccttactt taaaaggtgt      60
gaagtgtgaa gtgcagttgg tggagtctgg gggaggctta gtgacgcctg gagggtccct     120
gaaactctcc tgtgcagcct ctggattcgc tttcaattac tatgacatgt ttgggttcg     180
ccagaatacg gaaaagaggc tggagtgggt cgcatacatt aatagtggtg gtggtaatac     240
```

```
ctactatcca gacactgtga agggccgttt caccatctcc agagacaatg ccaagaaaac    300 cctgttttg caaatgagca gtctgaggtc tgaggacaca gccatgtatt actgtgcaag     360
acaactctat ggtaactcct tctttgacta ctggggccaa ggcacctctc tcactgtctc    420
cgcagccaaa acgacacccc catccgtyta tccmttggyc cctggaagct tgg           473
```

<210> SEQ ID NO 8
<211> LENGTH: 157
<212> TYPE: PRT
<213> ORGANISM: artificial
<220> FEATURE:
<223> OTHER INFORMATION: Synthetic heavy chain of Mab 16F6 amino acid
      Sequence
<220> FEATURE:
<221> NAME/KEY: misc_feature
<222> LOCATION: (149)..(149)
<223> OTHER INFORMATION: Xaa can be any naturally occurring amino acid
<220> FEATURE:
<221> NAME/KEY: misc_feature
<222> LOCATION: (151)..(151)
<223> OTHER INFORMATION: Xaa can be any naturally occurring amino acid
<220> FEATURE:
<221> NAME/KEY: misc_feature
<222> LOCATION: (153)..(153)
<223> OTHER INFORMATION: Xaa can be any naturally occurring amino acid

<400> SEQUENCE: 8

```
Leu Val Asp Met Asp Ser Arg Leu Asn Leu Val Phe Leu Val Leu
1               5                   10                  15

Leu Lys Gly Val Lys Cys Glu Val Gln Leu Val Glu Ser Gly Gly
            20                  25                  30

Leu Val Thr Pro Gly Gly Ser Leu Lys Leu Ser Cys Ala Ala Ser Gly
        35                  40                  45

Phe Ala Phe Asn Tyr Tyr Asp Met Phe Trp Val Arg Gln Asn Thr Glu
    50                  55                  60

Lys Arg Leu Glu Trp Val Ala Tyr Ile Asn Ser Gly Gly Gly Asn Thr
65                  70                  75                  80

Tyr Tyr Pro Asp Thr Val Lys Gly Arg Phe Thr Ile Ser Arg Asp Asn
                85                  90                  95

Ala Lys Lys Thr Leu Phe Leu Gln Met Ser Ser Leu Arg Ser Glu Asp
            100                 105                 110

Thr Ala Met Tyr Tyr Cys Ala Arg Gln Leu Tyr Gly Asn Ser Phe Phe
        115                 120                 125

Asp Tyr Trp Gly Gln Gly Thr Ser Leu Thr Val Ser Ala Ala Lys Thr
    130                 135                 140

Thr Pro Pro Ser Xaa Tyr Xaa Leu Xaa Pro Gly Ser Leu
145                 150                 155
```

<210> SEQ ID NO 9
<211> LENGTH: 442
<212> TYPE: DNA
<213> ORGANISM: artificial
<220> FEATURE:
<223> OTHER INFORMATION: Synthetic light chain of Mab 16F6 DNA Sequence

<400> SEQUENCE: 9

```
gggaattcat ggagacacag actcaggtct ttgtattcgt gtttctctgg ttgtctggtg    60
ttgacggaga cattgtgatg acccagtctc acaaattcat gtccacatca gtaggagaca    120
gggtcaccat cacctgcaag gccagtcagg atgtgactac tgctgtagcc tggtatcagc    180
aaaaaccagg gcactctcct aaactactga tttattgggc gtccacccgc cacactggag    240
```

```
tccctgatcg cttcacaggc agtggatctg ggacagattt tactctcacc ctcaacagtg    300
tgcaggctga agacctggca ctttattact gtcaacaaca ttatagtact ccgctcacgt    360
tcggtgctgg gaccaagctg gagctgaaac gggctgatgc tgcaccaact gtatccatct    420
tcccaccatc cagtaagctt gg                                             442
```

```
<210> SEQ ID NO 10
<211> LENGTH: 146
<212> TYPE: PRT
<213> ORGANISM: artificial
<220> FEATURE:
<223> OTHER INFORMATION: Synthetic light chain of Mab 16F6 amino acid
      Sequence

<400> SEQUENCE: 10

Glu Phe Met Glu Thr Gln Thr Gln Val Phe Val Phe Val Phe Leu Trp
1               5                   10                  15

Leu Ser Gly Val Asp Gly Asp Ile Val Met Thr Gln Ser His Lys Phe
                20                  25                  30

Met Ser Thr Ser Val Gly Asp Arg Val Thr Ile Thr Cys Lys Ala Ser
            35                  40                  45

Gln Asp Val Thr Thr Ala Val Ala Trp Tyr Gln Gln Lys Pro Gly His
        50                  55                  60

Ser Pro Lys Leu Leu Ile Tyr Trp Ala Ser Thr Arg His Thr Gly Val
65                  70                  75                  80

Pro Asp Arg Phe Thr Gly Ser Gly Ser Gly Thr Asp Phe Thr Leu Thr
                85                  90                  95

Leu Asn Ser Val Gln Ala Glu Asp Leu Ala Leu Tyr Tyr Cys Gln Gln
                100                 105                 110

His Tyr Ser Thr Pro Leu Thr Phe Gly Ala Gly Thr Lys Leu Glu Leu
            115                 120                 125

Lys Arg Ala Asp Ala Ala Pro Thr Val Ser Ile Phe Pro Pro Ser Ser
        130                 135                 140

Lys Leu
145
```

```
<210> SEQ ID NO 11
<211> LENGTH: 470
<212> TYPE: DNA
<213> ORGANISM: artificial
<220> FEATURE:
<223> OTHER INFORMATION: Synthetic heavy chain of Mab 17F6 DNA Sequence

<400> SEQUENCE: 11
actagtcgac atgatggtgt taagtcttct gtacctgttg acagtcgttc ctggtatcct    60
gtctgatgtg cagcttcagg agtcaggacc tggtctggtg aaaccttctc agacagtgtc    120
cctcacctgc actgtcactg gcatctccat caccgctgga aattacagat ggagctggat    180
ccggcagttt ccaggaaaca aactggagtg gataggtac atatactaca gtggtaccat    240
tgcctacaat ccatctctca agtcgaac cgccatcact agagacagtt ccaagaacca    300
attcttcctg aaatgaact cttttgactgc tgaagacaca gccacatact actgtgcacg    360
agatcgggga tggttactac ttgactactg gggccaaggc accactctca cagtctcctc    420
agccaaaaca acagcccat ccgtttatcc cttggcccct ggaagcttgg                470
```

```
<210> SEQ ID NO 12
<211> LENGTH: 456
```

```
<212> TYPE: DNA
<213> ORGANISM: artificial
<220> FEATURE:
<223> OTHER INFORMATION: Synthetic light chain of Mab 17F6 DNA Sequence

<400> SEQUENCE: 12
actagtcgac atgaagttgc ctgttaggct gttggtgctg atgttctgga ttcctgcttc      60
cagcagtgat gttttgatga cccaaactcc actctccctg cctgtcagtc ttggagatca     120
agcctccatc tcttgcagat ctagtcagac cattgtacat agtaatggaa acacctattt     180
agaatggtac ctgcagaaac aggccagtcc tccaaagctc ctgatctaca aggtttccag     240
ccgattttct ggggtcccag acaggttcag tggcagtgga tcaggacaga tttcacact     300
caagatcagm agagtggagg ctgaggatct gggagtttat tactgctttc aaggttcaca     360
ttttccgtac acgttcggag gggggaccaa gctggaaata aaacgggctg atgctgcacc     420
aactgtatcc atcttcccac catccagtaa gcttgg                              456
```

```
<210> SEQ ID NO 13
<211> LENGTH: 676
<212> TYPE: PRT
<213> ORGANISM: Ebola virus (Sudan)

<400> SEQUENCE: 13
```

Met Gly Gly Leu Ser Leu Leu Gln Leu Pro Arg Asp Lys Phe Arg Lys
1               5                   10                  15

Ser Ser Phe Phe Val Trp Val Ile Ile Leu Phe Gln Lys Ala Phe Ser
            20                  25                  30

Met Pro Leu Gly Val Val Thr Asn Ser Thr Leu Glu Val Thr Glu Ile
        35                  40                  45

Asp Gln Leu Val Cys Lys Asp His Leu Ala Ser Thr Asp Gln Leu Lys
    50                  55                  60

Ser Val Gly Leu Asn Leu Glu Gly Ser Gly Val Ser Thr Asp Ile Pro
65                  70                  75                  80

Ser Ala Thr Lys Arg Trp Gly Phe Arg Ser Gly Val Pro Pro Lys Val
                85                  90                  95

Val Ser Tyr Glu Ala Gly Glu Trp Ala Glu Asn Cys Tyr Asn Leu Glu
            100                 105                 110

Ile Lys Lys Pro Asp Gly Ser Glu Cys Leu Pro Pro Pro Asp Gly
        115                 120                 125

Val Arg Gly Phe Pro Arg Cys Arg Tyr Val His Lys Ala Gln Gly Thr
    130                 135                 140

Gly Pro Cys Pro Gly Asp Tyr Ala Phe His Lys Asp Gly Ala Phe Phe
145                 150                 155                 160

Leu Tyr Asp Arg Leu Ala Ser Thr Val Ile Tyr Arg Gly Val Asn Phe
                165                 170                 175

Ala Glu Gly Val Ile Ala Phe Leu Ile Leu Ala Lys Pro Lys Glu Thr
            180                 185                 190

Phe Leu Gln Ser Pro Pro Ile Arg Glu Ala Val Asn Tyr Thr Glu Asn
        195                 200                 205

Thr Ser Ser Tyr Tyr Ala Thr Ser Tyr Leu Glu Tyr Glu Ile Glu Asn
    210                 215                 220

Phe Gly Ala Gln His Ser Thr Thr Leu Phe Lys Ile Asp Asn Asn Thr
225                 230                 235                 240

Phe Val Arg Leu Asp Arg Pro His Thr Pro Gln Phe Leu Phe Gln Leu
                245                 250                 255

```
Asn Asp Thr Ile His Leu His Gln Gln Leu Ser Asn Thr Thr Gly Arg
            260                 265                 270

Leu Ile Trp Thr Leu Asp Ala Asn Ile Asn Ala Asp Ile Gly Glu Trp
    275                 280                 285

Ala Phe Trp Glu Asn Lys Lys Asn Leu Ser Glu Gln Leu Arg Gly Glu
290                 295                 300

Glu Leu Ser Phe Glu Ala Leu Ser Leu Asn Glu Thr Glu Asp Asp Asp
305                 310                 315                 320

Ala Ala Ser Ser Arg Ile Thr Lys Gly Arg Ile Ser Asp Arg Ala Thr
                325                 330                 335

Arg Lys Tyr Ser Asp Leu Val Pro Lys Asn Ser Pro Gly Met Val Pro
            340                 345                 350

Leu His Ile Pro Glu Gly Glu Thr Thr Leu Pro Ser Gln Asn Ser Thr
        355                 360                 365

Glu Gly Arg Arg Val Gly Val Asn Thr Gln Glu Thr Ile Thr Glu Thr
    370                 375                 380

Ala Ala Thr Ile Ile Gly Thr Asn Gly Asn His Met Gln Ile Ser Thr
385                 390                 395                 400

Ile Gly Ile Arg Pro Ser Ser Ser Gln Ile Pro Ser Ser Ser Pro Thr
                405                 410                 415

Thr Ala Pro Ser Pro Glu Ala Gln Thr Pro Thr Thr His Thr Ser Gly
            420                 425                 430

Pro Ser Val Met Ala Thr Glu Pro Thr Thr Pro Gly Ser Ser
        435                 440                 445

Pro Gly Pro Thr Thr Glu Ala Pro Thr Leu Thr Thr Pro Glu Asn Ile
    450                 455                 460

Thr Thr Ala Val Lys Thr Val Leu Pro Gln Glu Ser Thr Ser Asn Gly
465                 470                 475                 480

Leu Ile Thr Ser Thr Val Gly Ile Leu Gly Ser Leu Gly Leu Arg
                485                 490                 495

Lys Arg Ser Arg Arg Gln Thr Asn Thr Lys Ala Thr Gly Lys Cys Asn
            500                 505                 510

Pro Asn Leu His Tyr Trp Thr Ala Gln Glu Gln His Asn Ala Ala Gly
        515                 520                 525

Ile Ala Trp Ile Pro Tyr Phe Gly Pro Gly Ala Glu Gly Ile Tyr Thr
    530                 535                 540

Glu Gly Leu Met His Asn Gln Asn Ala Leu Val Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Tyr Thr Ile Leu Asn Arg Lys Ala Ile Asp Phe
            580                 585                 590

Leu Leu Arg Arg Trp Gly Gly Thr Cys Arg Ile Leu Gly Pro Asp Cys
        595                 600                 605

Cys Ile Glu Pro His Asp Trp Thr Lys Asn Ile Thr Asp Lys Ile Asn
    610                 615                 620

Gln Ile Ile His Asp Phe Ile Asp Asn Pro Leu Pro Asn Gln Asp Asn
625                 630                 635                 640

Asp Asp Asn Trp Trp Thr Gly Trp Arg Gln Trp Ile Pro Ala Gly Ile
                645                 650                 655

Gly Ile Thr Gly Ile Ile Ile Ala Ile Ile Ala Leu Leu Cys Val Cys
            660                 665                 670

Lys Leu Leu Cys
```

```
              675
```

<210> SEQ ID NO 14
<211> LENGTH: 677
<212> TYPE: PRT
<213> ORGANISM: Ebola virus (Reston)

<400> SEQUENCE: 14

```
Met Gly Ser Gly Tyr Gln Leu Leu Gln Leu Pro Arg Glu Arg Phe Arg
1               5                   10                  15

Lys Thr Ser Phe Leu Val Trp Val Ile Ile Leu Phe Gln Arg Ala Ile
            20                  25                  30

Ser Met Pro Leu Gly Ile Val Thr Asn Ser Thr Leu Lys Ala Thr Glu
        35                  40                  45

Ile Asp Gln Leu Val Cys Arg Asp Lys Leu Ser Ser Thr Ser Gln Leu
    50                  55                  60

Lys Ser Val Gly Leu Asn Leu Glu Gly Asn Gly Ile Ala Thr Asp Val
65                  70                  75                  80

Pro Ser Ala Thr Lys Arg Trp Gly Phe Arg Ser Gly Val Pro Pro Lys
                85                  90                  95

Val Val Ser Tyr Glu Ala Gly Glu Trp Ala Glu Asn Cys Tyr Asn Leu
            100                 105                 110

Glu Ile Lys Lys Ser Asp Gly Ser Glu Cys Leu Pro Leu Pro Pro Asp
        115                 120                 125

Gly Val Arg Gly Phe Pro Arg Cys Arg Tyr Val His Lys Val Gln Gly
    130                 135                 140

Thr Gly Pro Cys Pro Gly Asp Leu Ala Phe His Lys Asn Gly Ala Phe
145                 150                 155                 160

Phe Leu Tyr Asp Arg Leu Ala Ser Thr Val Ile Tyr Arg Gly Thr Thr
                165                 170                 175

Phe Ala Glu Gly Val Val Ala Phe Leu Ile Leu Ser Glu Pro Lys Lys
            180                 185                 190

His Phe Trp Lys Ala Thr Pro Ala His Glu Pro Val Asn Thr Thr Asp
        195                 200                 205

Asp Ser Thr Ser Tyr Tyr Met Thr Leu Thr Leu Ser Tyr Glu Met Ser
    210                 215                 220

Asn Phe Gly Gly Asn Glu Ser Asn Thr Leu Phe Lys Val Asp Asn His
225                 230                 235                 240

Thr Tyr Val Gln Leu Asp Arg Pro His Thr Pro Gln Phe Leu Val Gln
                245                 250                 255

Leu Asn Glu Thr Leu Arg Arg Asn Asn Arg Leu Ser Asn Ser Thr Gly
            260                 265                 270

Arg Leu Thr Trp Thr Leu Asp Pro Lys Ile Glu Pro Asp Val Gly Glu
        275                 280                 285

Trp Ala Phe Trp Glu Thr Lys Lys Asn Phe Ser Gln Gln Leu His Gly
    290                 295                 300

Glu Asn Leu His Phe Gln Ile Pro Ser Thr His Thr Asn Asn Ser Ser
305                 310                 315                 320

Asp Gln Ser Pro Ala Gly Thr Val Gln Gly Lys Ile Ser Tyr His Pro
                325                 330                 335

Pro Ala Asn Asn Ser Glu Leu Val Pro Thr Asp Ser Pro Pro Val Val
            340                 345                 350

Ser Val Leu Thr Ala Gly Arg Thr Glu Glu Met Ser Thr Gln Gly Leu
        355                 360                 365
```

Thr Asn Gly Glu Thr Ile Thr Gly Phe Thr Ala Asn Pro Met Thr Thr
370                 375                 380

Thr Ile Ala Pro Ser Pro Thr Met Thr Ser Glu Val Asp Asn Asn Val
385                 390                 395                 400

Pro Ser Glu Gln Pro Asn Asn Thr Ala Ser Ile Glu Asp Ser Pro Pro
            405                 410                 415

Ser Ala Ser Asn Glu Thr Ile Tyr His Ser Glu Met Asp Pro Ile Gln
            420                 425                 430

Gly Ser Asn Asn Ser Ala Gln Ser Pro Gln Thr Lys Thr Thr Pro Ala
            435                 440                 445

Pro Thr Thr Ser Pro Met Thr Gln Asp Pro Gln Glu Thr Ala Asn Ser
450                 455                 460

Ser Lys Pro Gly Thr Ser Pro Gly Ser Ala Ala Gly Pro Ser Gln Pro
465                 470                 475                 480

Gly Leu Thr Ile Asn Thr Val Ser Lys Val Ala Asp Ser Leu Ser Pro
                485                 490                 495

Thr Arg Lys Gln Lys Arg Ser Val Arg Gln Asn Thr Ala Asn Lys Cys
                500                 505                 510

Asn Pro Asp Leu Tyr Tyr Trp Thr Ala Val Asp Glu Gly Ala Ala Val
                515                 520                 525

Gly Leu Ala Trp Ile Pro Tyr Phe Gly Pro Ala Ala Glu Gly Ile Tyr
530                 535                 540

Ile Glu Gly Val Met His Asn Gln Asn Gly Leu Ile Cys Gly Leu Arg
545                 550                 555                 560

Gln Leu Ala Asn Glu Thr Thr Gln Ala Leu Gln Leu Phe Leu Arg Ala
                565                 570                 575

Thr Thr Glu Leu Arg Thr Tyr Ser Leu Leu Asn Arg Lys Ala Ile Asp
                580                 585                 590

Phe Leu Leu Gln Arg Trp Gly Gly Thr Cys Arg Ile Leu Gly Pro Ser
                595                 600                 605

Cys Cys Ile Glu Pro His Asp Trp Thr Lys Asn Ile Thr Asp Glu Ile
610                 615                 620

Asn Gln Ile Lys His Asp Phe Ile Asp Asn Pro Leu Pro Asp His Gly
625                 630                 635                 640

Asp Asp Leu Asn Leu Trp Thr Gly Trp Arg Gln Trp Ile Pro Ala Gly
                645                 650                 655

Ile Gly Ile Ile Gly Val Ile Ile Ala Ile Ile Ala Leu Leu Cys Ile
                660                 665                 670

Cys Lys Ile Leu Cys
        675

<210> SEQ ID NO 15
<211> LENGTH: 676
<212> TYPE: PRT
<213> ORGANISM: Ebola virus (Zaire)

<400> SEQUENCE: 15

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
        35                  40                  45

Asp Lys Leu Val Cys Arg Asp Lys Leu Ser Ser Thr Asn Gln Leu Arg
    50                  55                  60

```
Ser Val Gly Leu Asn Leu Glu Gly Asn Gly Val Ala Thr Asp Val Pro
 65                  70                  75                  80

Ser Ala Thr Lys Arg Trp Gly Phe Arg Ser Gly Val Pro Pro Lys Val
                 85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
    130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Thr Ile Arg Tyr Gln Ala Thr Gly
    210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Asn Leu Thr Arg Lys Ile Arg Ser Glu
    290                 295                 300

Glu Leu Ser Phe Thr Ala Val Ser Asn Arg Ala Lys Asn Ile Ser Gly
305                 310                 315                 320

Gln Ser Pro Ala Arg Thr Ser Ser Asp Pro Gly Thr Asn Thr Thr Thr
                325                 330                 335

Glu Asp His Lys Ile Met Ala Ser Glu Asn Ser Ser Ala Met Val Gln
            340                 345                 350

Val His Ser Gln Gly Arg Glu Ala Ala Val Ser His Leu Thr Thr Leu
        355                 360                 365

Ala Thr Ile Ser Thr Ser Pro Gln Pro Pro Thr Thr Lys Pro Gly Pro
    370                 375                 380

Asp Asn Ser Thr His Asn Thr Pro Val Tyr Lys Leu Asp Ile Ser Glu
385                 390                 395                 400

Ala Thr Gln Val Glu Gln His His Arg Arg Thr Asp Asn Asp Ser Thr
                405                 410                 415

Ala Ser Asp Thr Pro Pro Ala Thr Thr Ala Ala Gly Pro Leu Lys Ala
            420                 425                 430

Glu Asn Thr Asn Thr Ser Lys Gly Thr Asp Leu Leu Asp Pro Ala Thr
        435                 440                 445

Thr Thr Ser Pro Gln Asn His Ser Glu Thr Ala Gly Asn Asn Asn Thr
    450                 455                 460

His His Gln Asp Thr Gly Glu Glu Ser Ala Ser Ser Gly Lys Leu Gly
465                 470                 475                 480
```

```
Leu Ile Thr Asn Thr Ile Ala Gly Val Ala Gly Leu Ile Thr Gly Gly
                485                 490                 495

Arg Arg Ala Arg Arg Glu Ala Ile Val Asn Ala Gln Pro Lys Cys Asn
            500                 505                 510

Pro Asn Leu His Tyr Trp Thr Thr Gln Asp Glu Gly Ala Ala Ile Gly
        515                 520                 525

Leu Ala Trp Ile Pro Tyr Phe Gly Pro Ala Ala Glu Gly Ile Tyr Thr
    530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Lys Ile Asp
    610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Ile Ile Ala Val Ile Ala Leu Phe Cys Ile Cys
            660                 665                 670

Lys Phe Val Phe
        675

<210> SEQ ID NO 16
<211> LENGTH: 676
<212> TYPE: PRT
<213> ORGANISM: Ebola virus (Bundibugyo)

<400> SEQUENCE: 16

Met Val Thr Ser Gly Ile Leu Gln Leu Pro Arg Glu Arg Phe Arg Lys
1               5                   10                  15

Thr Ser Phe Phe Val Trp Val Ile Ile Leu Phe His Lys Val Phe Pro
            20                  25                  30

Ile Pro Leu Gly Val Val His Asn Asn Thr Leu Gln Val Ser Asp Ile
        35                  40                  45

Asp Lys Leu Val Cys Arg Asp Lys Leu Ser Ser Thr Ser Gln Leu Lys
    50                  55                  60

Ser Val Gly Leu Asn Leu Glu Gly Asn Gly Val Ala Thr Asp Val Pro
65                  70                  75                  80

Thr Ala Thr Lys Arg Trp Gly Phe Arg Ala Gly Val Pro Pro Lys Val
                85                  90                  95

Val Asn Tyr Glu Ala Gly Glu Trp Ala Glu Asn Cys Tyr Asn Leu Asp
            100                 105                 110

Ile Lys Lys Ala Asp Gly Ser Glu Cys Leu Pro Glu Ala Pro Glu Gly
        115                 120                 125

Val Arg Gly Phe Pro Arg Cys Arg Tyr Val His Lys Val Ser Gly Thr
    130                 135                 140

Gly Pro Cys Pro Glu Gly Tyr Ala Phe His Lys Glu Gly Ala Phe Phe
145                 150                 155                 160

Leu Tyr Asp Arg Leu Ala Ser Thr Ile Ile Tyr Arg Ser Thr Thr Phe
                165                 170                 175
```

```
Ser Glu Gly Val Val Ala Phe Leu Ile Leu Pro Thr Lys Lys Asp
            180                 185                 190

Phe Phe Gln Ser Pro Pro Leu His Glu Pro Ala Asn Met Thr Thr Asp
        195                 200                 205

Pro Ser Ser Tyr Tyr His Thr Val Thr Leu Asn Tyr Val Ala Asp Asn
    210                 215                 220

Phe Gly Thr Asn Met Thr Asn Phe Leu Phe Gln Val Asp His Leu Thr
225                 230                 235                 240

Tyr Val Gln Leu Glu Pro Arg Phe Thr Pro Gln Phe Leu Val Gln Leu
            245                 250                 255

Asn Glu Thr Ile Tyr Thr Asn Gly Arg Arg Ser Asn Thr Thr Gly Thr
        260                 265                 270

Leu Ile Trp Lys Val Asn Pro Thr Val Asp Thr Gly Val Gly Glu Trp
    275                 280                 285

Ala Phe Trp Glu Asn Lys Lys Asn Phe Thr Lys Thr Leu Ser Ser Glu
        290                 295                 300

Glu Leu Ser Val Ile Phe Val Pro Arg Ala Gln Asp Pro Gly Ser Asn
305                 310                 315                 320

Gln Lys Thr Lys Val Thr Pro Thr Ser Phe Ala Asn Asn Gln Thr Ser
            325                 330                 335

Lys Asn His Glu Asp Leu Val Pro Glu Asp Pro Ala Ser Val Val Gln
        340                 345                 350

Val Arg Asp Leu Gln Arg Glu Asn Thr Val Pro Thr Pro Pro Pro Asp
    355                 360                 365

Thr Val Pro Thr Thr Leu Ile Pro Asp Thr Met Glu Glu Gln Thr Thr
            370                 375                 380

Ser His Tyr Glu Pro Pro Asn Ile Ser Arg Asn His Gln Glu Arg Asn
385                 390                 395                 400

Asn Thr Ala His Pro Glu Thr Leu Ala Asn Asn Pro Pro Asp Asn Thr
            405                 410                 415

Thr Pro Ser Thr Pro Pro Gln Asp Gly Glu Arg Thr Ser Ser His Thr
        420                 425                 430

Thr Pro Ser Pro Arg Pro Val Pro Thr Ser Thr Ile His Pro Thr Thr
    435                 440                 445

Arg Glu Thr His Ile Pro Thr Thr Met Thr Thr Ser His Asp Thr Asp
450                 455                 460

Ser Asn Arg Pro Asn Pro Ile Asp Ile Ser Glu Ser Thr Glu Pro Gly
465                 470                 475                 480

Pro Leu Thr Asn Thr Thr Arg Gly Ala Ala Asn Leu Leu Thr Gly Ser
            485                 490                 495

Arg Arg Thr Arg Arg Glu Ile Thr Leu Arg Thr Gln Ala Lys Cys Asn
        500                 505                 510

Pro Asn Leu His Tyr Trp Thr Thr Gln Asp Glu Gly Ala Ala Ile Gly
    515                 520                 525

Leu Ala Trp Ile Pro Tyr Phe Gly Pro Ala Ala Glu Gly Ile Tyr Thr
            530                 535                 540

Glu Gly Ile Met His Asn Gln Asn Gly Leu Ile Cys Gly Leu Arg Gln
545                 550                 555                 560

Leu Ala Asn Glu Thr Thr Gln Ala Leu Gln Leu Phe Leu Arg Ala Thr
            565                 570                 575

Thr Glu Leu Arg Thr Phe Ser Ile Leu Asn Arg Lys Ala Ile Asp Phe
        580                 585                 590
```

```
Leu Leu Gln Arg Trp Gly Gly Thr Cys His Ile Leu Gly Pro Asp Cys
            595                 600                 605

Cys Ile Glu Pro His Asp Trp Thr Lys Asn Ile Thr Asp Lys Ile Asp
610                 615                 620

Gln Ile Ile His Asp Phe Ile Asp Lys Pro Leu Pro Asp Gln Thr Asp
625                 630                 635                 640

Asn Asp Asn Trp Trp Thr Gly Trp Arg Gln Trp Val Pro Ala Gly Ile
                645                 650                 655

Gly Ile Thr Gly Val Ile Ile Ala Val Ile Ala Leu Leu Cys Ile Cys
                660                 665                 670

Lys Phe Leu Leu
            675

<210> SEQ ID NO 17
<211> LENGTH: 676
<212> TYPE: PRT
<213> ORGANISM: Ebola virus (Cote DIvoire)

<400> SEQUENCE: 17

Met Gly Ala Ser Gly Ile Leu Gln Leu Pro Arg Glu Arg Phe Arg Lys
1               5                   10                  15

Thr Ser Phe Phe Val Trp Val Ile Leu Phe His Lys Val Phe Ser
                20                  25                  30

Ile Pro Leu Gly Val Val His Asn Asn Thr Leu Gln Val Ser Asp Ile
            35                  40                  45

Asp Lys Phe Val Cys Arg Asp Lys Leu Ser Ser Thr Ser Gln Leu Lys
    50                  55                  60

Ser Val Gly Leu Asn Leu Glu Gly Asn Gly Val Ala Thr Asp Val Pro
65                  70                  75                  80

Thr Ala Thr Lys Arg Trp Gly Phe Arg Ala Gly Val Pro Pro Lys Val
                85                  90                  95

Val Asn Tyr Glu Ala Gly Glu Trp Ala Glu Asn Cys Tyr Asn Leu Ala
            100                 105                 110

Ile Lys Lys Val Asp Gly Ser Glu Cys Leu Pro Glu Ala Pro Glu Gly
        115                 120                 125

Val Arg Asp Phe Pro Arg Cys Arg Tyr Val His Lys Val Ser Gly Thr
    130                 135                 140

Gly Pro Cys Pro Gly Gly Leu Ala Phe His Lys Glu Gly Ala Phe Phe
145                 150                 155                 160

Leu Tyr Asp Arg Leu Ala Ser Thr Ile Ile Tyr Arg Gly Thr Thr Phe
                165                 170                 175

Ala Glu Gly Val Ile Ala Phe Leu Ile Leu Pro Lys Ala Arg Lys Asp
            180                 185                 190

Phe Phe Gln Ser Pro Pro Leu His Glu Pro Ala Asn Met Thr Thr Asp
        195                 200                 205

Pro Ser Ser Tyr Tyr His Thr Thr Thr Ile Asn Tyr Val Val Asp Asn
    210                 215                 220

Phe Gly Thr Asn Thr Thr Glu Phe Leu Phe Gln Val Asp His Leu Thr
225                 230                 235                 240

Tyr Val Gln Leu Glu Ala Arg Phe Thr Pro Gln Phe Leu Val Leu Leu
                245                 250                 255

Asn Glu Thr Ile Tyr Ser Asp Asn Arg Arg Ser Asn Thr Thr Gly Lys
            260                 265                 270

Leu Ile Trp Lys Ile Asn Pro Thr Val Asp Thr Ser Met Gly Glu Trp
        275                 280                 285
```

```
Ala Phe Trp Glu Asn Lys Lys Asn Phe Thr Lys Thr Leu Ser Ser Glu
        290                 295                 300

Glu Leu Ser Phe Val Pro Val Pro Glu Thr Gln Asn Gln Val Leu Asp
305                 310                 315                 320

Thr Thr Ala Thr Val Ser Pro Pro Ile Ser Ala His Asn His Ala Gly
                325                 330                 335

Glu Asp His Lys Glu Leu Val Ser Glu Asp Ser Thr Pro Val Val Gln
            340                 345                 350

Met Gln Asn Ile Lys Gly Lys Asp Thr Met Pro Thr Thr Val Thr Gly
        355                 360                 365

Val Pro Thr Thr Thr Pro Ser Pro Phe Pro Ile Asn Ala Arg Asn Thr
370                 375                 380

Asp His Thr Lys Ser Phe Ile Gly Leu Glu Gly Pro Gln Glu Asp His
385                 390                 395                 400

Ser Thr Thr Gln Pro Ala Lys Thr Thr Ser Gln Pro Thr Asn Ser Thr
                405                 410                 415

Glu Ser Thr Thr Leu Asn Pro Thr Ser Glu Pro Ser Ser Arg Gly Thr
            420                 425                 430

Gly Pro Ser Ser Pro Thr Val Pro Asn Thr Thr Glu Ser His Ala Glu
        435                 440                 445

Leu Gly Lys Thr Thr Pro Thr Thr Leu Pro Glu Gln His Thr Ala Ala
450                 455                 460

Ser Ala Ile Pro Arg Ala Val His Pro Asp Glu Leu Ser Gly Pro Gly
465                 470                 475                 480

Phe Leu Thr Asn Thr Ile Arg Gly Val Thr Asn Leu Leu Thr Gly Ser
                485                 490                 495

Arg Arg Lys Arg Arg Asp Val Thr Pro Asn Thr Gln Pro Lys Cys Asn
            500                 505                 510

Pro Asn Leu His Tyr Trp Thr Ala Leu Asp Glu Gly Ala Ala Ile Gly
        515                 520                 525

Leu Ala Trp Ile Pro Tyr Phe Gly Pro Ala Ala Glu Gly Ile Tyr Thr
530                 535                 540

Glu Gly Ile Met Glu Asn Gln Asn Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro Gln Asp Trp Thr Lys Asn Ile Thr Asp Lys Ile Asp
610                 615                 620

Gln Ile Ile His Asp Phe Val Asp Asn Asn Leu Pro Asn Gln Asn Asp
625                 630                 635                 640

Gly Ser Asn Trp Trp Thr Gly Trp Lys Gln Trp Val Pro Ala Gly Ile
                645                 650                 655

Gly Ile Thr Gly Val Ile Ile Ala Ile Ile Ala Leu Leu Cys Ile Cys
            660                 665                 670

Lys Phe Met Leu
        675

<210> SEQ ID NO 18
<211> LENGTH: 681
```

<212> TYPE: PRT
<213> ORGANISM: Marburg virus

<400> SEQUENCE: 18

```
Met Lys Thr Thr Cys Phe Leu Ile Ser Leu Ile Leu Ile Gln Gly Thr
1               5                   10                  15

Lys Asn Leu Pro Ile Leu Glu Ile Ala Ser Asn Asn Gln Pro Gln Asn
            20                  25                  30

Val Asp Ser Val Cys Ser Gly Thr Leu Gln Lys Thr Glu Asp Val His
        35                  40                  45

Leu Met Gly Phe Thr Leu Ser Gly Gln Lys Val Ala Asp Ser Pro Leu
    50                  55                  60

Glu Ala Ser Lys Arg Trp Ala Phe Arg Thr Gly Val Pro Pro Lys Asn
65                  70                  75                  80

Val Glu Tyr Thr Glu Gly Glu Ala Lys Thr Cys Tyr Asn Ile Ser
                85                  90                  95

Val Thr Asp Pro Ser Gly Lys Ser Leu Leu Asp Pro Pro Thr Asn
                100                 105                 110

Ile Arg Asp Tyr Pro Lys Cys Lys Thr Ile His His Ile Gln Gly Gln
            115                 120                 125

Asn Pro His Ala Gln Gly Ile Ala Leu His Leu Trp Gly Ala Phe Phe
    130                 135                 140

Leu Tyr Asp Arg Ile Ala Ser Thr Thr Met Tyr Arg Gly Lys Val Phe
145                 150                 155                 160

Thr Glu Gly Asn Ile Ala Ala Met Ile Val Asn Lys Thr Val His Lys
                165                 170                 175

Met Ile Phe Ser Arg Gln Gly Gln Gly Tyr Arg His Met Asn Leu Thr
            180                 185                 190

Ser Thr Asn Lys Tyr Trp Thr Ser Ser Asn Gly Thr Gln Thr Asn Asp
        195                 200                 205

Thr Gly Cys Phe Gly Ala Leu Gln Glu Tyr Asn Ser Thr Lys Asn Gln
    210                 215                 220

Thr Cys Ala Pro Ser Lys Ile Pro Pro Leu Pro Thr Ala Arg Pro
225                 230                 235                 240

Glu Ile Lys Leu Thr Ser Thr Pro Thr Asp Ala Thr Lys Leu Asn Thr
                245                 250                 255

Thr Asp Pro Ser Ser Asp Asp Glu Asp Leu Ala Thr Ser Gly Ser Gly
            260                 265                 270

Ser Gly Glu Arg Glu Pro His Thr Thr Ser Asp Ala Val Thr Lys Gln
        275                 280                 285

Gly Leu Ser Ser Thr Met Pro Pro Thr Pro Ser Pro Gln Pro Ser Thr
    290                 295                 300

Pro Gln Gln Gly Gly Asn Asn Thr Asn His Ser Gln Asp Ala Val Thr
305                 310                 315                 320

Glu Leu Asp Lys Asn Asn Thr Thr Ala Gln Pro Ser Met Pro Pro His
                325                 330                 335

Asn Thr Thr Thr Ile Ser Thr Asn Asn Thr Ser Lys His Asn Phe Ser
            340                 345                 350

Thr Leu Ser Ala Pro Leu Gln Asn Thr Thr Asn Asp Asn Thr Gln Ser
        355                 360                 365

Thr Ile Thr Glu Asn Glu Gln Thr Ser Ala Pro Ser Ile Thr Thr Leu
    370                 375                 380

Pro Pro Thr Gly Asn Pro Thr Thr Ala Lys Ser Thr Ser Ser Lys Lys
385                 390                 395                 400
```

Gly Pro Ala Thr Thr Ala Pro Asn Thr Thr Asn Glu His Phe Thr Ser
            405                 410                 415

Pro Pro Pro Thr Pro Ser Ser Thr Ala Gln His Leu Val Tyr Phe Arg
            420                 425                 430

Arg Lys Arg Ser Ile Leu Trp Arg Glu Gly Asp Met Phe Pro Phe Leu
            435                 440                 445

Asp Gly Leu Ile Asn Ala Pro Ile Asp Phe Asp Pro Val Pro Asn Thr
        450                 455                 460

Lys Thr Ile Phe Asp Glu Ser Ser Ser Gly Ala Ser Ala Glu Glu
465                 470                 475                 480

Asp Gln His Ala Ser Pro Asn Ile Ser Leu Thr Leu Ser Tyr Phe Pro
                485                 490                 495

Asn Ile Asn Glu Asn Thr Ala Tyr Ser Gly Glu Asn Glu Asn Asp Cys
            500                 505                 510

Asp Ala Glu Leu Arg Ile Trp Ser Val Gln Glu Asp Leu Ala Ala
        515                 520                 525

Gly Leu Ser Trp Ile Pro Phe Phe Gly Pro Gly Ile Glu Gly Leu Tyr
        530                 535                 540

Thr Ala Val Leu Ile Lys Asn Gln Asn Asn Leu Val Cys Arg Leu Arg
545                 550                 555                 560

Arg Leu Ala Asn Gln Thr Ala Lys Ser Leu Glu Leu Leu Leu Arg Val
                565                 570                 575

Thr Thr Glu Glu Arg Thr Phe Ser Leu Ile Asn Arg His Ala Ile Asp
            580                 585                 590

Phe Leu Leu Thr Arg Trp Gly Gly Thr Cys Lys Val Leu Gly Pro Asp
        595                 600                 605

Cys Cys Ile Gly Ile Glu Asp Leu Ser Lys Asn Ile Ser Glu Gln Ile
        610                 615                 620

Asp Gln Ile Lys Lys Asp Glu Gln Lys Glu Gly Thr Gly Trp Gly Leu
625                 630                 635                 640

Gly Gly Lys Trp Trp Thr Ser Asp Trp Gly Val Leu Thr Asn Leu Gly
                645                 650                 655

Ile Leu Leu Leu Leu Ser Ile Ala Val Leu Ile Ala Leu Ser Cys Ile
            660                 665                 670

Cys Arg Ile Phe Thr Lys Tyr Ile Gly
        675                 680

<210> SEQ ID NO 19
<211> LENGTH: 533
<212> TYPE: PRT
<213> ORGANISM: Ebola virus

<400> SEQUENCE: 19

Ser Met Pro Leu Gly Val Val Thr Asn Ser Thr Leu Glu Val Thr Glu
1               5                   10                  15

Ile Asp Gln Leu Val Cys Lys Asp His Leu Ala Ser Thr Asp Gln Leu
            20                  25                  30

Lys Ser Val Gly Leu Asn Leu Glu Gly Ser Gly Val Ser Thr Asp Ile
        35                  40                  45

Pro Ser Ala Thr Lys Arg Trp Gly Phe Arg Ser Gly Val Pro Pro Lys
    50                  55                  60

Val Val Ser Tyr Glu Ala Gly Glu Trp Ala Glu Asn Cys Tyr Asn Leu
65                  70                  75                  80

Glu Ile Lys Lys Pro Asp Gly Ser Glu Cys Leu Pro Pro Pro Pro Asp

```
            85                  90                  95
Gly Val Arg Gly Phe Pro Arg Cys Arg Tyr Val His Lys Ala Gln Gly
            100                 105                 110

Thr Gly Pro Cys Pro Gly Asp Tyr Ala Phe His Lys Asp Gly Ala Phe
            115                 120                 125

Phe Leu Tyr Asp Arg Leu Ala Ser Thr Val Ile Tyr Arg Gly Val Asn
            130                 135                 140

Phe Ala Glu Gly Val Ile Ala Phe Leu Ile Leu Ala Lys Pro Lys Glu
145                 150                 155                 160

Thr Phe Leu Gln Ser Pro Pro Ile Arg Glu Ala Val Asn Tyr Thr Glu
                165                 170                 175

Asn Thr Ser Ser Tyr Tyr Ala Thr Ser Tyr Leu Glu Tyr Glu Ile Glu
                180                 185                 190

Asn Phe Gly Ala Gln His Ser Thr Thr Leu Phe Lys Ile Asp Asn Asn
                195                 200                 205

Thr Phe Val Arg Leu Asp Arg Pro His Thr Pro Gln Phe Leu Phe Gln
            210                 215                 220

Leu Asn Asp Thr Ile His Leu His Gln Gln Leu Ser Asn Thr Thr Gly
225                 230                 235                 240

Arg Leu Ile Trp Thr Leu Asp Ala Asn Ile Asn Ala Asp Ile Gly Glu
                245                 250                 255

Trp Ala Phe Trp Glu Asn Lys Lys Asn Leu Ser Glu Gln Leu Arg Gly
                260                 265                 270

Glu Glu Leu Ser Phe Glu Ala Leu Ser Leu Asn Glu Thr Glu Asp Asp
                275                 280                 285

Asp Ala Ala Ser Ser Arg Ile Thr Lys Gly Arg Ile Ser Asp Arg Ala
            290                 295                 300

Thr Arg Lys Tyr Ser Asp Leu Val Pro Lys Asn Ser Pro Gly Met Val
305                 310                 315                 320

Pro Leu His Ile Pro Glu Gly Glu Thr Thr Leu Pro Ser Gln Asn Ser
                325                 330                 335

Thr Glu Gly Arg Arg Val Gly Val Asn Thr Gln Glu Thr Ile Thr Glu
                340                 345                 350

Thr Ala Ala Thr Ile Ile Gly Thr Asn Gly Asn His Met Gln Ile Ser
            355                 360                 365

Thr Ile Gly Ile Arg Pro Ser Ser Ser Gln Ile Pro Ser Ser Ser Pro
            370                 375                 380

Thr Thr Ala Pro Ser Pro Glu Ala Gln Thr Pro Thr Thr His Thr Ser
385                 390                 395                 400

Gly Pro Ser Val Met Ala Thr Glu Glu Pro Thr Thr Pro Pro Gly Ser
                405                 410                 415

Ser Pro Gly Pro Thr Thr Glu Ala Pro Thr Leu Thr Thr Pro Glu Asn
            420                 425                 430

Ile Thr Thr Ala Val Lys Thr Val Leu Pro Gln Glu Ser Thr Ser Asn
            435                 440                 445

Gly Leu Ile Thr Ser Thr Val Thr Gly Ile Leu Gly Ser Leu Gly Leu
450                 455                 460

Arg Lys Arg Ser Arg Gln Thr Asn Thr Lys Ala Thr Gly Lys Cys
465                 470                 475                 480

Asn Pro Asn Leu His Tyr Trp Thr Ala Gln Glu Gln His Asn Ala Ala
                485                 490                 495

Gly Ile Ala Trp Ile Pro Tyr Phe Gly Pro Gly Ala Glu Gly Ile Tyr
            500                 505                 510
```

```
Thr Glu Gly Leu Met His Asn Gln Asn Ala Leu Val Cys Gly Leu Arg
        515                 520                 525

Gln Leu Ala Asn Glu
    530

<210> SEQ ID NO 20
<211> LENGTH: 7
<212> TYPE: PRT
<213> ORGANISM: artificial
<220> FEATURE:
<223> OTHER INFORMATION: Synthetic heavy chain of Mab 17F6 amino acid

<400> SEQUENCE: 20

Ala Gly Asn Tyr Arg Trp Ser
1               5

<210> SEQ ID NO 21
<211> LENGTH: 16
<212> TYPE: PRT
<213> ORGANISM: artificial
<220> FEATURE:
<223> OTHER INFORMATION: synthetic ehavy chain construct of the Mab 17F6

<400> SEQUENCE: 21

Asn Ile Tyr Tyr Ser Gly Thr Ile Ala Tyr Asn Pro Ser Leu Thr Ser
1               5                   10                  15

<210> SEQ ID NO 22
<211> LENGTH: 9
<212> TYPE: PRT
<213> ORGANISM: artificial
<220> FEATURE:
<223> OTHER INFORMATION: synthetic construct of Mab 17F6 Heavy variable
      chain

<400> SEQUENCE: 22

Asp Arg Gly Trp Leu Leu Leu Asp Tyr
1               5

<210> SEQ ID NO 23
<211> LENGTH: 11
<212> TYPE: PRT
<213> ORGANISM: artificial
<220> FEATURE:
<223> OTHER INFORMATION: artificial construct of the light variable
      chain of the Mab 16F6

<400> SEQUENCE: 23

Lys Ala Ser Gln Asp Val Thr Thr Ala Val Ala
1               5                   10

<210> SEQ ID NO 24
<211> LENGTH: 7
<212> TYPE: PRT
<213> ORGANISM: artificial
<220> FEATURE:
<223> OTHER INFORMATION: Synthetic construct of the light variable chain
      of the Mab 16F6

<400> SEQUENCE: 24

Trp Ala Ser Thr Arg His Thr
1               5

<210> SEQ ID NO 25
<211> LENGTH: 9
<212> TYPE: PRT
```

-continued

```
<213> ORGANISM: artificial
<220> FEATURE:
<223> OTHER INFORMATION: synthetic construct of variable region of light
      chain Mab 16F6

<400> SEQUENCE: 25

Gln Gln His Tyr Ser Thr Pro Leu Thr
1               5
```

MONOCLONAL ANTIBODIES AGAINST GLYCOPROTEIN OF EBOLA SUDAN BONIFACE VIRUS

CROSS REFERENCE TO RELATED APPLICATION

This application is a National Stage of International Application No. PCT/US2010/047586 filed Sep. 1, 2010, and claims the benefit of U.S. Provisional Application No. 61/239,166, filed Sep. 2, 2009 and U.S. Provisional Application No. 61/290,725, filed Dec. 29, 2009, which are incorporated herein by reference in their entirety.

RIGHTS IN THE INVENTION

This invention was made with support from the United States Army Medical Research Institute of Infectious Diseases and with government support under R01AI111516-01 awarded by the National Institutes of Health. The United States government has certain rights in this invention.

REFERENCE TO A SEQUENCE LISTING

The instant application contains a Sequence Listing which has been submitted in ASCII format via EFS-Web and is hereby incorporated by reference in its entirety. Said ASCII copy, created on Feb. 18, 2015, is named sub_seq_listing_ST25.txt and is 54,175 bytes in size.

FIELD AND BACKGROUND OF THE INVENTION

The invention is related generally to the field of antibodies, and specifically to monoclonal antibodies against the Ebola Sudan Boniface virus (SBEBOV).

Ebola hemorrhagic fever is a disease in humans, chimpanzees, and monkeys, caused by infection with Ebola virus, and associated with high mortality. This virus was first recognized in Zaire, Africa in 1976. The exact origin and location of Ebola virus is still unknown. Ebola virus is one of only two known members of a family of RNA viruses, the Filoviridae. (The other member is the Marburg virus). Ebola virus (EBOV) is an enveloped, non-segmented, negative-strand virus. The virus causes a severe hemorrhagic fever disease with a high mortality rate and there are no licensed vaccines or therapeutics approved for human use. To date, most published reports have focused on exposure to a subtype of EBOV isolated from the Zaire region in 1976, Ebola virus Zaire (ZEBOV). ZEBOV is believed to have the highest mortality rate in humans (90%) of the different subtypes of Ebola.

In 1976, the Sudan subtype of the Ebola virus (SEBOV) was discovered concurrently with the Zaire subtype when simultaneous, but separate, outbreaks of Ebola hemorrhagic fever erupted in the nations of Sudan and Zaire, respectively. This new isolate was named Sudan Boniface Ebola virus (SBEBOV). The Sudan subtype has been responsible for four outbreaks of Ebola hemorrhagic fever, including the largest ever Ebola virus outbreak in Uganda in 2000 and 2001, with 425 cases and 224 deaths. This outbreak marked the reemergence of the Sudan subtype after 21 years, and originated close to the city of Gulu near the Uganda-Sudan border. The virus isolated from this outbreak was named Sudan Gulu Ebola Virus (SGEBOV). In 2004, a smaller epidemic occurred near the city of Yambio in southern Sudan, very near the location of the 1976 outbreak. Infection with SBEBOV and SGEBOV was 40-65% lethal in the human population. Genomic sequence of both the SBEBOV and the SGEBOV was determined and is 95.3% identical at the amino acid level. However, the sequence of SBEBOV and SGEBOV is only 54.2% and 54.6% identical to ZEBOV, respectively.

The Ebola genome shows a linear gene arrangement with the following protein coding regions—nucleoprotein (NP)—viral structural protein—(VP) 35—VP40—glycoprotein (GP)—VP30—VP24—and, polymerase (L). To date, four species of Ebola virus have been identified: Ebola Zaire, Ebola Sudan, Ebola Ivory Coast, and Ebola Reston. Different strains have been identified among within the species. Ebola Zaire consists of four identified strains, Zaire Maying a, Zaire-95, Eckron-76, and Gabon-94. Ebola Sudan consists of Sudan Boniface and Sudan Maleo-79. Ebola Reston consists of Reston and Reston Siena/Philippine-92. Ebola Ivory Coast consists of only one known strain, Ivory Coast-94. All four known species of Ebola virus have infected humans, but with differing degrees of lethality between species and even among different strains of the same species. Zaire Mayinga and Zaire-95 are the two most lethal forms of the Ebola virus, killing approximately 85% of all known infected humans. Zaire Gabon, Sudan Boniface, and Sudan Maleo-79 are less lethal, killing between 53 and 66% of its victims.

The majority of research in the filovirus community has focused on the Zaire virus species of EBOV; however, the Sudan ebolavirus (SEBOV) species is of similar public health concern. There are known murine monoclonal antibodies that recognize Ebola Zaire glycoprotein (Science, 3 Mar. 2000, volume 287, pp. 1664-1666, Wilson et al., Epitopes Involved in Antibody-Mediated Protection from Ebola Virus). The Zaire monoclonals are disclosed in U.S. Pat. Nos. 6,630,144 and 6,875,433 and U.S. patent application Ser. Nos. 60/560,086, 10/384,976 and 10/696,633, all of which are incorporated by reference in their entirety herein. However, no antibodies against the Sudan Boniface species of the Ebola Virus are known to exist.

Ebolavirus (EBOV) causes a severe hemorrhagic fever with up to 90% human mortality (1). Outbreaks of EBOV have become increasingly more frequent (four in the last two years, including appearance of EBOV infection in domesticated swine), yet no vaccines or treatments are approved for human use (2). Five species have been identified: Sudan, Zaire, Côte d'Ivoire, Reston and the proposed Bundibugyo (1, 3), although almost all human deaths have been the result of infection with either Sudan ebolavirus (SEBOV) or Zaire ebolavirus (ZEBOV). Indeed, SEBOV and ZEBOV were the first two species of ebolavirus to be identified, with their names derived from simultaneous outbreaks in 1976 in the nations of Sudan and Zaire, respectively. This original SEBOV outbreak was caused by a viral strain termed Boniface. However, a new SEBOV strain emerged in October 2000 in northwestern Uganda. This strain, termed Gulu, triggered the largest outbreak of Ebola hemorrhagic fever yet described, involving at least 425 individuals, of whom 224 died (4).

Multiple monoclonal antibodies against ZEBOV have been developed (5-10), however, not one has been shown to neutralize SEBOV. SEBOV is 40% divergent in sequence and antigenically distinct from ZEBOV. Consequently, the development of antibodies that neutralize SEBOV is critical for provision of therapeutics and for further development and improvement of broad-range vaccines.

Ebolavirus entry is a multi-step process including attachment of virions to target cells, internalization of virions into the endosome, and fusion of the virus with the endosomal membrane for release of viral contents into the cytoplasm. The surface glycoprotein GP is the sole EBOV protein responsible for attachment, fusion and entry. Hence, GP is a critical component of vaccines and the target of neutralizing antibodies.

The role of anti-GP antibodies in protection is confounded by the observation that Ebola GP occurs in several forms. The transmembrane glycoprotein of Ebola viruses is unusual in that it is encoded in two open reading frames. Expression of GP occurs when the 2 reading frames are connected by transcriptional or translational editing (Sanchez et al., Proc. Natl. Acad. Sci. USA 93; 3602-3607, 1996; Volchkov et al., Virology 214, 421-430, 1995). The unedited GP mRNA produces a non-structural secreted glycoprotein (sGP) that is synthesized in large amounts early during the course of infection (Volchkov et al., 1995, supra; Sanchez et al., 1996, supra; Sanchez et al., J. Infect. Dis. 179 (suppl. 1, S164, 1999). Following editing, the virion-associated transmembrane glycoprotein is proteolytically processed into 2 disulfide-linked products (Sanchez et al., J. Virol. 72, 6442-6447, 1998). The amino-terminal product is referred to as GP1 (140 kDa) and the carboxy-terminal cleavage product is referred to as GP2 (26 kDa). GP1 and membrane-bound GP, covalently associate to form a monomer of the GP spike found on the surfaces of virions (V E. Volchkov et al., Proc. Natl. Acad. Sci. U.S.A. 95, 5762, 1998; A. Sanchez et al., J. Virol. 72, 6442, 1998). GP1 is also released from infected cells in a soluble form (V E. Volchkov. et al., Virology 245, 110, 1998). sGP and GP1 are identical in their first 295 N-terminal amino acids, whereas the remaining 69 C-terminal amino acids of sGP and 206 amino acids of GP1 are encoded by different reading frames. It has been suggested that secreted GP1 or sGP may effectively bind antibodies that might otherwise be protective (Sanchez el al., 1996, supra; Volchkov el al. 1998, supra).

Ebola virus GP is a Type I transmembrane glycoprotein. Comparisons of the predicted amino acid sequences for the GPs of the different Ebola virus strains show conservation of amino acids in the amino-terminal and carboxy-terminal regions with a highly variable region in the middle of the protein (Feldmann el al., Virus Res. 24: 1-19, 1992). The GP of Ebola viruses are highly glycosylaled and contain both N-linked and O-linked carbohydrates that contribute up to 50% of the molecular weight of the protein. Most of the glycosylation sites are found in the central variable region of GP.

GP is expressed as a 676 amino acid precursor that is post-translationally cleaved by furin to yield two subunits, GP1 and GP2 (11). GP1 and GP2 remain covalently linked by a disulfide bond (12), and the resulting GP1-GP2 pair trimerizes to yield a ~450 kDa envelope spike on the viral surface. GP1 is responsible for attachment to new host cells while GP2 mediates fusion with those cells. GP1 also serves as a hydrophobic clamp on GP2, holding it in its metastable, pre-fusion conformation on the viral surface. When the clamp is released during entry, GP2 is thought to undergo irreversible conformational changes that drive fusion with host endosomal membranes (13, 14). Although a definitive receptor has yet to be identified for the ebolaviruses, virions can enter cells through an endocytic pathway (15-18). A key step in this pathway appears to be cleavage of a flexible loop containing GP1 residues 190-213 (19, 20), by endosomal cathepsins (15-17). Several neutralizing mAbs have been raised against ZEBOV (5, 7-10), but it is not yet known at what stage of entry these antibodies function.

Other studies have also demonstrated limited efficacy of passively transferred polyclonal antibodies in protection against Ebola challenge (Mikhailov et al, 1994, Voprosi Virusologii, 39, 82-84; Jahrling et al., 1996, Arch Virol, US, 135-140; Jahrling et al., 1999, J Infect Dis, 179 (Suppl 1), S224-234; Kudoyarova-Zubavichene et al., 1999, J Infect Dis, 179 (Suppl 1), S218-223). However, it is difficult to determine the effective therapeutic dose of antibodies in different preparations of polyclonal antibodies. Efforts to identify the role of antibodies in protection led to the isolation of monoclonal antibodies from mice vaccinated with Ebola GP (for instance, U.S. Pat. Nos. 6,630,144; 6,875,433; 7,335,356; and Wilson et al. Science 287, 1664, 2000), and from convalescent people (Maruyama et al. J. Infect. Dis. 179 (suppl 1), S235, 1999; Maruyama et al. J. Virol. 73, 6024, 1999; Parren et al. J. Virol 76, 6408, 2002). These were tested in rodents and protected against lethal infection (Wilson et al. Science 287, 1664, 2000; Parren et al. J. Virol 76, 6408, 2002).

Therefore, there exists a need for antibodies reactant to the Sudan Boniface virus and means to produce the same so that the virus may be detected and methods of treatment and prophylaxis against the same may be developed.

SUMMARY OF THE INVENTION

Monoclonal antibodies (MAbs) against glycoproteins (GPs) of the Ebola Sudan Boniface Virus are disclosed, as are hybridoma cells which produce the same. A crystal structure of the trimeric, prefusion Sudan ebolavirus glycoprotein, in complex with a novel Sudan ebolavirus-neutralizing antibody, illustrates a shared structural epitope which could be a "sweet spot" for neutralizing the ebolaviruses. These MAbs were protective against Ebola Sudan Boniface Virus challenge when administered prophylactically or therapeutically. (By "prophylactic", it is meant administered before challenge, and by "therapeutic", it is meant administered after challenge.)

The invention of these monoclonal antibodies that recognize the glycoprotein of Sudan Boniface mark the first time to our knowledege that a reagent has been developed that will specifically identify Ebola Sudan Boniface.

The monoclonals generated in this disclosure are the only known Sudan specific monoclonal antibodies. This invention will allow a scientist to specifically recognize the Sudan Boniface species of Ebola Virus in an outbreak situation.

Cross-reactivity across all the Ebola and Marburg viruses is not present. Therefore, a diagnostic or therapeutic medical countermeasure against one Ebola strain will not cross react with another Ebola strain. It is therefore prudent to have as many monoclonal antibodies (MAbs) MAbs in the art as possible to ensure a wide variety of MAbs against Ebola virus infections.

One embodiment of this invention relates to monoclonal antibodies that protect against Ebola Sudan Boniface virus and bind to epitopes on the virus GP.

Another embodiment relates to the sequences of these monoclonal antibodies, in particular, the sequences to MAbs: 16H11, 19B3, 17F6, 16F6, and 17F6.

A further embodiment relates to the complementary determining regions of these five antibodies (16H11, 19B3, 17F6, 16F6, and 17F6) which are involved with the binding of the monoclonal antibodies to Ebola Sudan Boniface virus.

Another embodiment of the invention relates to antibodies that are functionally equivalent to the antibodies listed above. These functionally equivalent antibodies substantially share at least one major functional property with an antibody listed above and herein described comprising: binding specificity to Ebola Sudan Boniface (ESB) GP, protection against ESB challenge when administered prophylactically or therapeutically, competition for same binding site on ESB GP, and/or use of the same combination of complementarity determining regions. The antibodies can be of any class such as IgG, IgM, or IgA or any subclass such as IgG1, IgG2a, and other subclasses known in the art. Further, the antibodies can be produced by any method, such as phage display, or produced in any organism or cell line, including bacteria, insect, mammal or other type of cell or cell line which produces antibodies with desired characteristics, such as humanized antibodies. The antibodies can also be formed by combining a Fab portion and a Fc region from different species, or by keeping the complementarity-determining regions and modifying the framework regions to that of another species (such a human, which is described in more detail below).

The monoclonal antibodies of the present invention described below recognize epitopes on Ebola Sudan Boniface GP (SEQ ID NO: 13 describes the amino acid sequence of ESB GP used as an immunogen) within the sequence extending from residues 32 and 533. More specifically, the MAbs 16H11 (SEQ ID NOS. 1 and 2), 19B3 (SEQ ID NOS. 3 and 4), 17F6 (SEQ ID NOS. 5, 11 and 6, 12), and 16F6 (SEQ ID NOS. 7-10) recognize conformational epitopes in the ESB GP sequence that compromise discontinuous ESB virus amino acids (SEQ ID NO. 19 and FIG. 17).

A further embodiment of the present invention provides for mixtures of the above-described antibodies, as well as to methods of using individual antibodies, or mixtures thereof for the prevention and/or therapeutic treatment of ESB infections in vitro and in vivo, and/or for improved detection of ESB infections.

Another embodiment relates to the treatment or prevention of ESB virus infection by administering a therapeutically or prophylactically effective amount of one antibody of the present invention or a mixture of antibodies of the present invention to a subject in need of such treatment.

A further embodiment provides passive vaccines for treating or preventing ESB virus infections comprising a therapeutically or prophylactically effective amount of the antibodies of the present invention which protect against ESB virus, in combination with a pharmaceutically acceptable carrier or excipient.

Yet another embodiment provides methods for diagnosis of ESB virus infection by assaying for the presence of ESB in a sample using the antibodies of the present invention.

Still another embodiment provides novel immunoprobes and test kits for detection of ESB virus infection comprising antibodies according to the present invention. For immunoprobes, the antibodies are directly or indirectly attached to a suitable reporter molecule, e.g., and enzyme or a radionuclide. The test kit includes a container holding one or more antibodies according to the present invention and instructions for using the antibodies for the purpose of binding to ESB virus to form an immunological complex and detecting the formation of the immunological complex such that presence or absence of the immunological complex correlates with presence or absence of ESB virus.

In another embodiment, there are provided anti-idiotypic antibodies raised against one of the present monoclonal antibodies for use as a vaccine to elicit an active anti-GP response.

In a further embodiment, there are provided antigenic epitopes as a component of a ESB virus vaccine. The epitopes described above comprising SEQ ID NO: 19, or conservative changes thereof which are still recognized by the antibodies, are useful for actively immunizing a host to elicit production of protective antibodies against ESB.

It is an object of the present invention to facilitate the identification of the Sudan Boniface species of Ebola virus in an outbreak situation.

It is another object of the present invention that these antibodies or "humanized" versions of these monoclonals could be used as therapeutic treatment in Ebola Sudan patients.

It is, further still, an object of the present invention that the glycoprotein disclosed be produced by alternative cells such as insect cell lines and mammalian cell lines producing this protein.

Another object of this invention is to disclose means for quantification for dosing determination of vaccine candidates utilizing the Sudan Boniface glycoprotein.

The various features of novelty that characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

Figure 2:
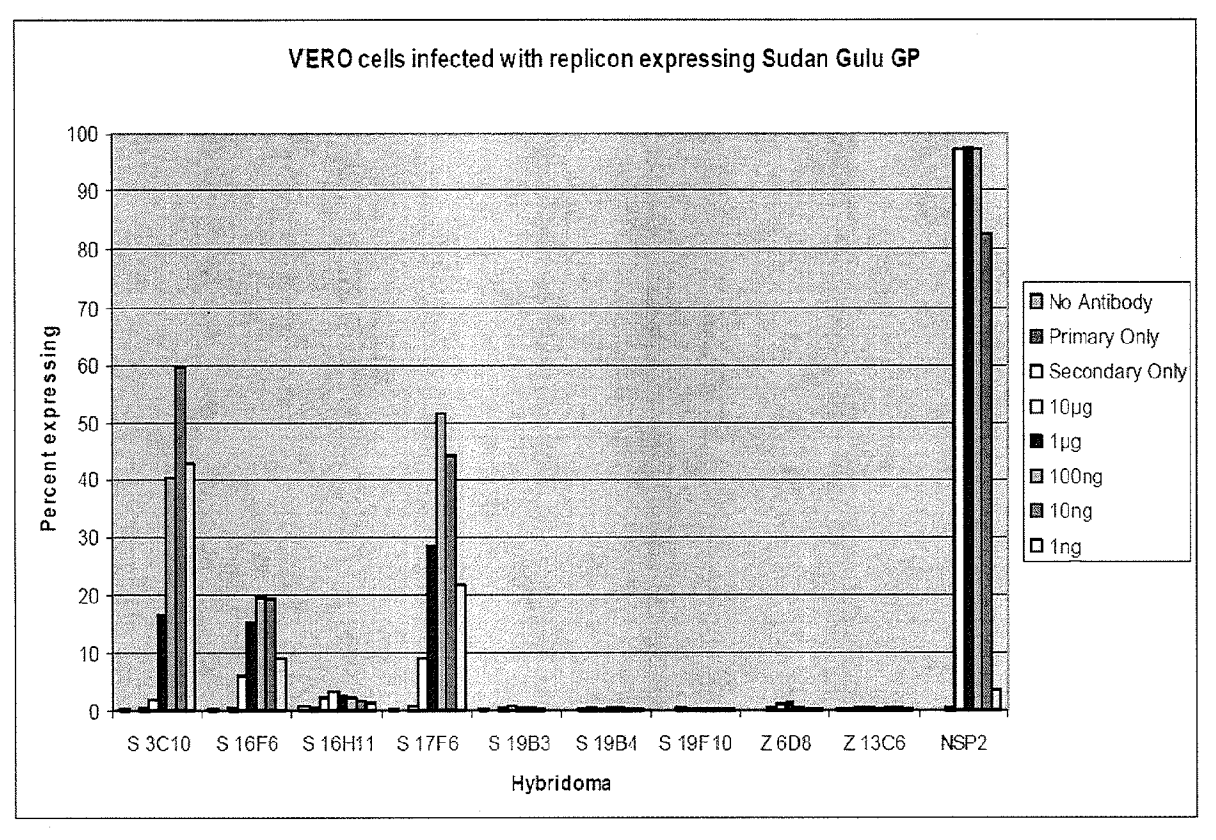

FIG. 2 is a graph showing percentage of primary antibody antibody expression (at specified concentrations) in VERO cells infected with replicon expressing Sudan Gulu GP using a goat-anti mouse IgG FITC-conjugated secondary antibody.

Figure 4:
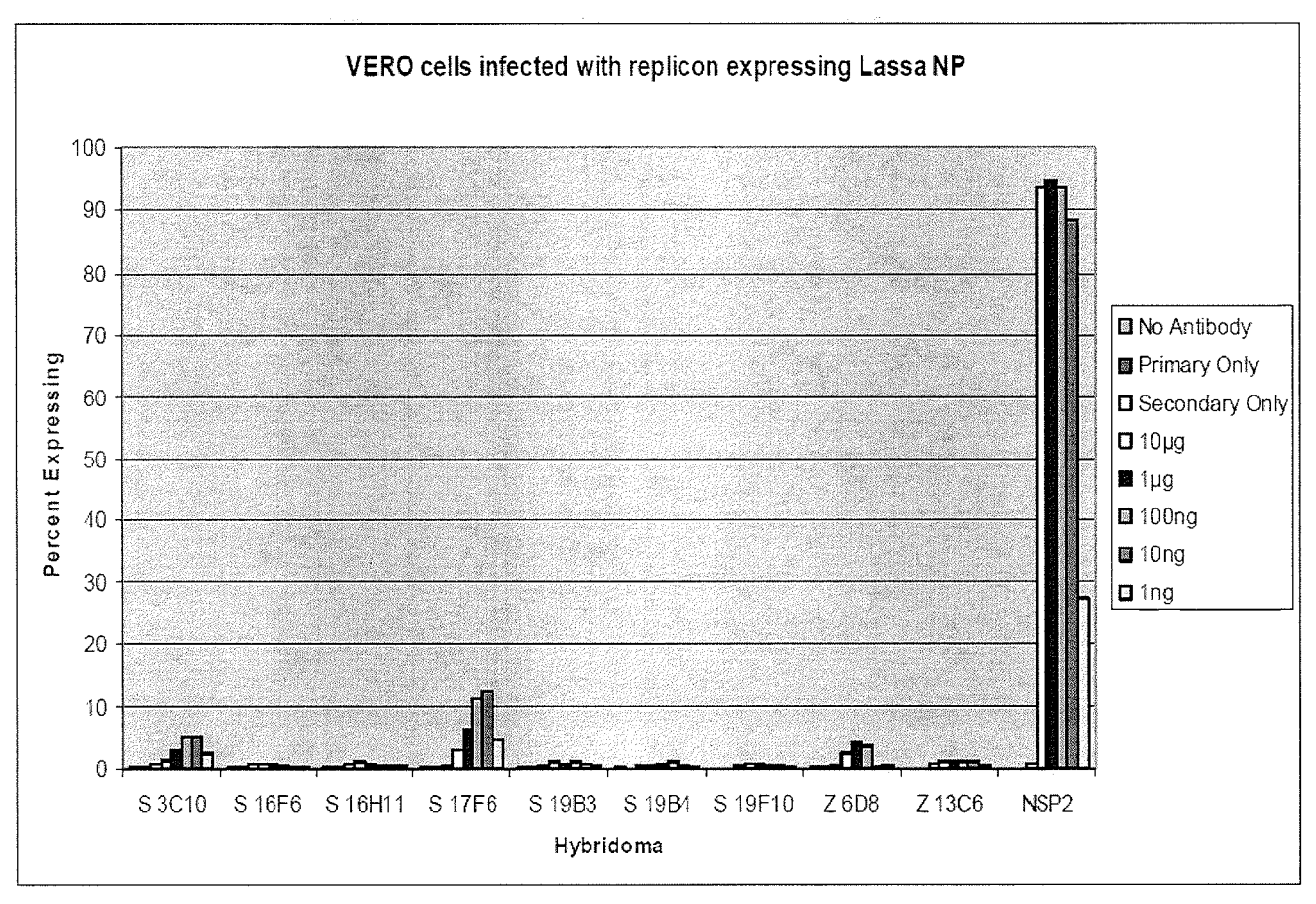

FIG. 4 is a graph showing percentage of primary antibody antibody expression (at specified concentrations) in VERO cells infected with replicon expressing Lassa NP using a goat-anti mouse IgG FITC-conjugated secondary antibody.

FIG. 6 is a photograph of 96-well nitrocelluslose plates containing overlapping 13-mer peptides of Ebolda Sudan GP incubated from antibodies generated from the 3C10 and 17F6 hybridomas. Dark spots identify the linear sequence of binding by indirect immunochemical means.

FIG. 7 is a table showing an overview of murine antibodies generated against Sudan Boniface Glycoprotein.

FIG. 8 is a table showing an overview of murine antibodies generated against Sudan Boniface Glycoprotein.

FIG. 18 is an overall structural model of the Sudan Ebolavirus GP with ribbon diagram (top) and domain schematic (bottom) of the GP Monomer (residues 32-192, 212-287, 300-311 and 510-615). The GP monomer is divided into two subunits GP1 and GP2. The GP1 subunit is divided in three subdomains (base, head, glycan cap). The base (B) comprises four discontinuous regions that form two mixed beta-sheet domains (residues 32-69, 95-104, 158-167, 176-192). The head (H) is also formed by four discontinuous regions (residues 70-94, 105-157, 168-175 and 212-227) and forms a four-stranded, mixed beta sheet supported by an alpha-helix and a smaller two-stranded, antiparallel beta sheet. The glycan cap (GC) is formed by residues 228-331 in a continuous polypeptide chain, and forms an alpha helix packed against a two stranded, antiparallel beta-sheet. The GP2 internal fusion loop (IFL) comprises residues 510-551 and the HR1 motif comprises residues 552-615 respectively. HR2, in the C-terminal region of GP2 after residue 615 is disordered and not visible in electron density maps. The intramolecular disulfide bridges are located between Cys108-Cys135, Cys121-Cys147, Cys511-Cys556 and Cys601-Cys608) and the interdisulfide bridge between GP1 and GP2 is located between Cys53-Cys609.

DESCRIPTION OF THE PREFERRED EMBODIMENTS

Figure 1:
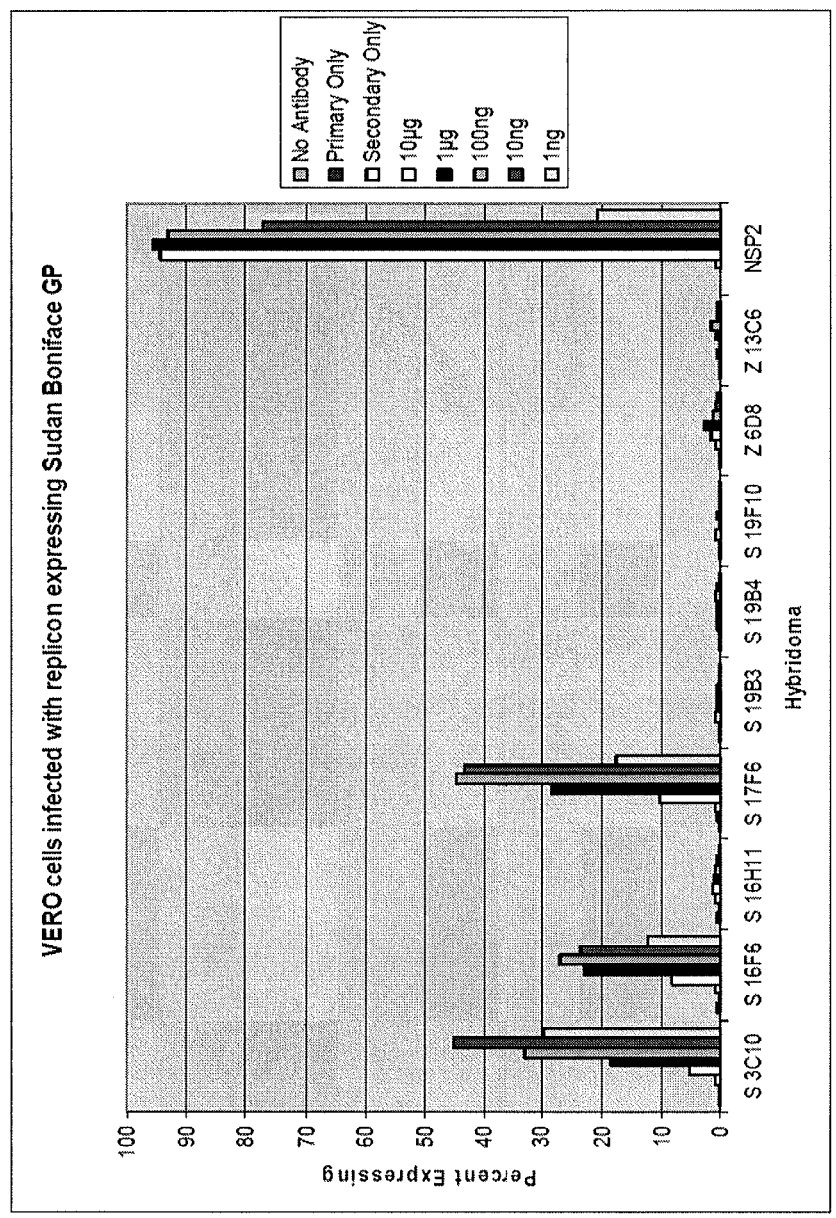
FIG. 1 is a graph showing percentage of primary antibody antibody expression (at specified concentrations) in VERO cells infected with replicon expressing Sudan Boniface GP using a goat-anti mouse IgG FITC-conjugated secondary antibody.
Figure 3:
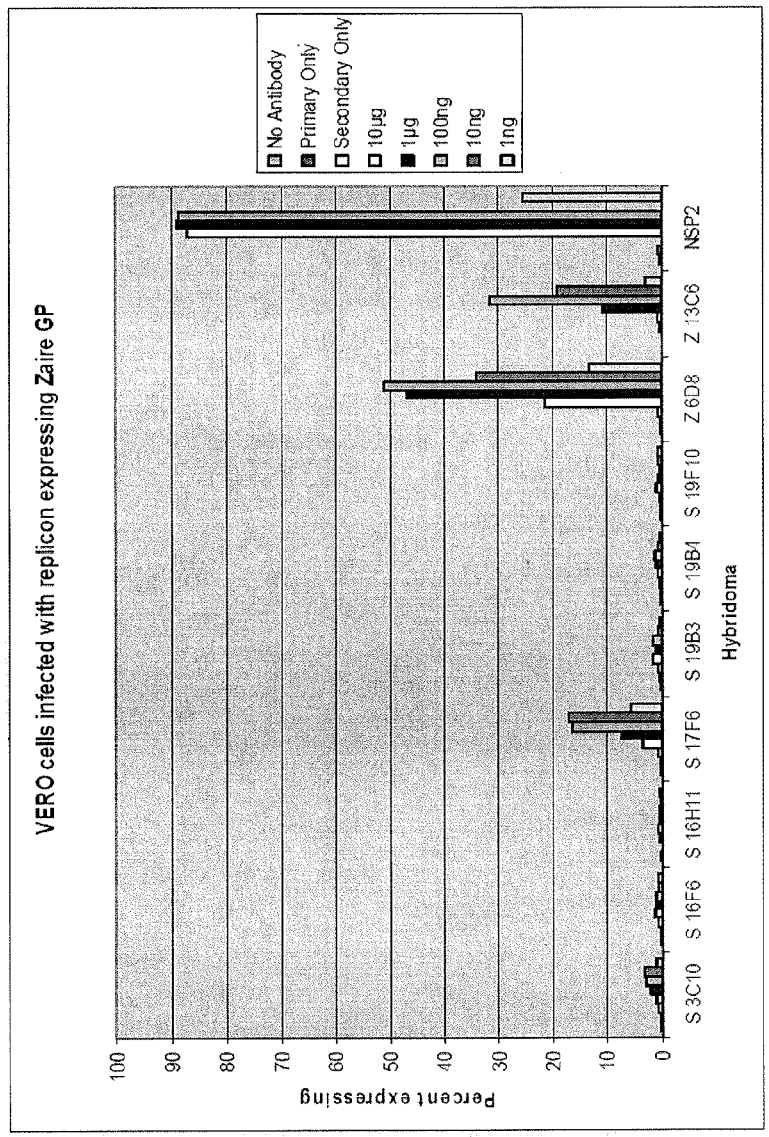
FIG. 3 is a graph showing percentage of primary antibody antibody expression (at specified concentrations) in VERO cells infected with replicon expressing Zaire GP using a goat-anti mouse IgG FITC-conjugated secondary antibody.

In the description that follows, a number of terms used in recombinant DNA, virology and immunology are extensively utilized. In order to provide a clearer and consistent understanding of the specification and claims, including the scope to be given such terms, the following definitions are provided. "Ebola viruses", members of the family Filoviridae, are associated with outbreaks of highly lethal hemorrhagic fever in humans and nonhuman primates. Human pathogens include Ebola Zaire, Ebola Sudan, and Ebola Ivory Coast. Ebola Reston is a monkey pathogen and is not considered a human pathogen. The natural reservoir of the virus is unknown and there are currently no available vaccines or effective therapeutic treatments for filovirus infections. The genome of Ebola virus consists of a single strand of negative sense RNA that is approximately 19 kb in length. This RNA contains seven sequentially arranged genes that produce 8 mRNAs upon infection. Ebola virions, like virions of other filoviruses, contain seven proteins: a surface glycoprotein (GP), a nucleoprotein (NP), four virion structural proteins (VP40, VP35, VP30, and VP24), and an RNA-dependent RNA polymerase (L) (Feldmann et al. (1992) Virus Res. 24, 1-19; Sanchez et al., (1993) Virus Res. 29, 215-240; reviewed in Peters et al. (1996) In Fields Virology, Third ed. pp. 1161-1176. Fields, B. N., Knipe, D. M., Howley, P. M., et al. eds. Lippincott-Raven Publishers, Philadelphia). The glycoprotein of Ebola virus is unusual in that it is encoded in two open reading frames. Transcriptional editing is needed to express the transmembrane form that is incorporated into the virion (Sanchez et al. (1996) Proc. Natl. Acad. Sci. USA 93, 3602-3607; Volchkov et al, (1995) Virology 214, 421-430). The unedited form produces a nonstructural secreted glycoprotein (sGP) that is synthesized in large amounts early during the course of infection. Little is known about the biological functions of these proteins and it is not known which antigens significantly contribute to protection and should therefore be used to induce an immune response.

The term "antibody" is art-recognized terminology and is intended to include molecules or active fragments of molecules that bind to known antigens. Examples of active fragments of molecules that bind to known antigens include Fab and F(ab')2 fragments. These active fragments can be derived from an antibody of the present invention by a number of techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. J. Nucl. Med. 23:1011-1019 (1982). The term "antibody" also includes bispecific and chimeric antibodies.

The language "monoclonal antibody" is art-recognized terminology. It is generally understood by those of skill in the art to refer to the antibody produced by one clone of B lymphocytes. The monoclonal antibodies of the present invention can be prepared using classical cloning and cell fusion techniques. The immunogen (antigen) of interest, Ebola Sudan Boniface GP protein, is typically administered (e.g. intraperitoneal injection) to wild type or inbred mice (e.g. BALB/c) or transgenic mice which produce desired antibodies, rats, rabbits or other animal species which can produce native or human antibodies. The immunogen can be administered alone, or mixed with adjuvant, or expressed from a vector (VEE replicon vector, vaccinia), or as DNA, or as a fusion protein to induce an immune response. Fusion proteins comprise the peptide against which an immune response is desired coupled to carrier proteins, such as b-galactosidase, glutathione S-transferase, keyhole limpet hemocyanin (KLH), and bovine serum albumin, to name a few. In these cases, the peptides serve as haptens with the carrier proteins. After the animal is boosted, for example, two or more times, the spleen can be removed and splenocytes can be extracted and fused with myeloma cells using the well-known processes of Kohler and Milstein (Nature 256: 495-497 (1975)) and Harlow and Lane (Antibodies: A Laboratory Manual (Cold Spring Harbor Laboratory, New York 1988)). The resulting hybrid cells can then be cloned in the conventional manner, e.g. using limiting dilution, and the resulting clones, which produce the desired monoclonal antibodies, cultured.

Monoclonal antibodies raised against ESB GP as described herein are 16H11, 19B3, 17F6, 16F6, and 17F6. Detailed structural information of Mab 16F6 is described below.

The monoclonal antibodies of this invention contain at least one "complementarity-determining region" (CDR). By "complementarity-determining region", it is meant the hypervariable regions in the heavy and light chains of an antibody molecule that form the 3-dimensional cavity by which the antibody binds to an epitope on the antigen.

The term "epitope" is art-recognized. It is generally understood by those of skill in the art to refer to the region of an antigen, such as ESB GP, that interacts with an antibody. An epitope of a peptide or protein antigen can be formed by contiguous or noncontiguous amino acid sequences of the antigen. ESB GB, like many large proteins, contains many epitopes.

An Example of a ESB GP epitope recognized by antibodies of the present invention include the region extending from 32 to 533 and described herein as SEQ ID NO. 19. The epitopes or peptides recognized by the antibodies of the present invention and conservative substitutions of these peptides which are still recognized by the antibody are an embodiment of the present invention. Further truncation of these epitopes may be possible, as would be understood by someone having ordinary skill in this art having this disclosure in hand.

By further mapping of the binding site of the monoclonal antibodies described in this disclosure other peptides useful as a vaccine or a therapeutic can be determined using known methodologies. Therefore, in another aspect, this invention relates to a method for identifying protective antigenic epitopes, which method comprises the steps of (i) reacting a monoclonal antibody described herein to different overlapping fragments encompassing the complete antigen, (ii) identifying a fragment to which the protective antibody binds, (iii) narrowing the region containing sites further by reacting the monoclonal with smaller overlapping fragments encompassing the region identified in (ii), and (iv) choosing peptides to which the antibody binds as possible antigenic epitopes. The peptides can then be assayed for their ability to protect an animal from disease, or to reduce the severity of disease. Peptides defining antigenic protective epitopes can be used in a vaccine as described below and in the Examples.

The epitopes or peptides on ESB GP to which the monoclonal antibodies bind can constitute all or part of an active vaccine. An active vaccine or therapeutic candidate might comprise these peptide sequences and others. These may be delivered as synthetic peptides, or as fusion proteins, alone or co-administered with cytokines and/or adjuvants or carriers safe for human use, e.g. aluminum hydroxide, to increase immunogenicity. In addition, sequences such as ubiquitin can be added to increase antigen processing for more effective immune responses.

Antibody molecules produced in vivo comprise two identical heavy chains that are covalently bound and two identical light chains, each of which is covalently bound to a heavy chain. Heavy and light chains each have one variable region and three constant regions. Within the variable regions of light and heavy chains are hypervariable sequences called complementarity-determining regions flanked by framework regions. The binding specificity of an antibody is conferred by its combination of complementarity-determining regions. There are three complementarity determining regions on the light chain and three on the heavy chain of an antibody molecule. Together, these form the 3-dimensional cavity that will bind (hold) an epitope on an antigen. Although these regions are hypervariable, a particular complementarity-determining region on one antibody may also be found on antibodies with different specificities, as it is the total combination of complementarity determining regions that is important. Generally, binding specificity is determined by the complementarity-determining regions on both chains, although it has been suggested that the complementarity-determining regions on the heavy chain do not contribute to specificity when the light chain is produced by a gene called lambda x. Identification of the complementarity-determining regions is useful for changing the "speciation" of an antibody, for example changing a mouse antibody to a humanized form suitable for human use, because one would want to preserve the complementarity-determining regions so as not to eliminate the binding specificity. Using the numbering system of Kabat et al, (NIH Publication No. 91-3242, 1991) in which the signal sequences of the heavy and light chains are indicated with negative numbers, the complementarity-determining regions of the light chain are between amino acids 24-34 (CDR1), 50-56 (CDR2) and 89-97 (95 a-f, CDR3). The complementarity-determining regions of the heavy chain are between amino acids 31-35 (35 a-b, CDR1), 50-65 (52 a-c, CDR2), and 95-102 (100 a-k, CDR3). Insertions of extra amino acids into the complementarity-determining regions can be observed and their locations are represented above in parentheses, e.g 95 a-f. Deletions are also observed, for example in CDR3 of some types of heavy chains.

Throughout this description we refer to the CDRs in terms of both the amino acid sequence and the location within the light or heavy chain. As someone having ordinary skill in this art would understand, the "location" of the CDRs is conserved between species, but through the use the well known Kabat system—an arbitrary numbering system that aligns sequences. Therefore, according to the Kabat system, the first invariant amino acid of a given type of light chain might be used to define the CDR beginning at, for example, "position 24" even if there are not 23 preceding amino acids. Therefore, for the purposes of the description of this invention we are defining CDRs as according to the Kabat system which is accepted in the art. The Kabat system aligns the Mab sequences of different species, for example mouse and human, such that all species have CDRs aligned at the same numbered "positions". Alignment of the sequences occurs through the identification of invariant residues in either the CDR or the framework regions adjacent to the CDR. There are different forms of light and heavy chain variable regions that differ in the use and location of the invariant residues, but Kabat et al. identify these. Using the nomenclature in the 1991 edition of Kabat et al, Mab 16H11 uses a heavy chain variable region of the IIB type. Mab 19B3 uses a heavy chain variable region of the IIB type. Mab 17F6 uses a heavy chain variable region of the IA type. Mab 16F6 uses a heavy chain variable region of the IIIA type and a kappa light chain of the miscellaneous type.

The DNA sequence of the variable regions of the heavy chain of Mab 16H11 is represented in SEQ ID NO. 1, and the amino acid sequence is represented in SEQ ID NO. 2. The DNA Sequence of the variable regions of the heavy chain of Mab 19B3 is represented in SEQ ID NO. 3, and the amino acid sequence is represented in SEQ ID NO. 4. The DNA Sequence of the variable regions of the heavy chain of Mab 17F6 is represented in SEQ ID NO. 5, and the amino acid sequence is represented in SEQ ID NO. 6. For the heavy chain, the CDRs were identified as located at the following positions:

31-35b: (where, as noted above, "b" signifies the insertion of an extra amino acid) having the amino acid sequence AGNYRWS with the last two amino acids representing insertions as 35a and 35b (SEQ ID NO. 20);

50-65: having the amino acid sequence NIYYSGTIAYNPSLTS (SEQ ID NO. 21), and;

95 to 102: having the amino acid sequence DRGWLLLDY (SEQ ID NO. 22).

The DNA Sequence of the variable regions of the heavy chain of Mab 16F6 is represented in SEQ ID NO. 7, and the amino acid sequence is represented in SEQ ID NO. 8. The DNA Sequence of the variable regions of the light chain of Mab 16F6 is represented in SEQ ID NO. 9, and the amino acid sequence is represented in SEQ ID NO. 10. For the light chain, the CDRs were identified as located at the following positions:

46-56: having the amino acid sequence KASQDVTTAVA (SEQ ID NO. 23);

71-77: having the amino acid sequence WASTRHT (SEQ ID NO. 24); and, 107-115: having the amino acid sequence QQHYSTPLT (SEQ ID NO. 25).

The invention also contemplates monoclonal antibodies having sequences that are at least 90%, and preferably 95%, homologous to the heavy and/or light chain regions described here as SEQ ID NOS. 1-10. There can be a 5% variation normally in even the more conserved framework regions, and someone having ordinary skill in this art using known techniques would be able to determine without undue experimentation such homologous, competing monoclonal antibodies.

Specificity generally is conferred with both heavy and light chains, and not usually with just the heavy or light chain alone; therefore, it is preferred that when this monoclonal antibody is used to detect ESB in a sample (as described below), or to prevent or treat ESB infection (as described below), both heavy and light chains are present.

The present invention also pertains to hybridomas producing antibodies which bind to an epitope of ESB GP. The term "hybridoma" is art recognized and is understood by those of ordinary skill in the art to refer to a cell produced by the fusion of an antibody-producing cell and an immortal cell, e.g. a multiple myeloma cell. This hybrid cell is capable of producing a continuous supply of antibody. See the definition of "monoclonal antibody" above and the Examples below for a more detailed description of the method of fusion.

The present invention still further pertains to a method for detecting ESB GP in a sample suspected of containing ESB GP. The method includes contacting the sample with an antibody which binds an epitope of ESB GP, allowing the antibody to bind to ESB GP to form an immunological complex, detecting the formation of the immunological complex and correlating the presence or absence of the immunological complex with the presence or absence of ESB GP in the sample. The sample can be biological, environmental or a food sample.

The language "detecting the formation of the immunological complex" is intended to include discovery of the presence or absence of ESB GP in a sample. The presence or absence of ESB GP can be detected using an immunoassay. A number of immunoassays used to detect and/or quantitate antigens are well known to those of ordinary skill in the art. See Harlow and Lane, Antibodies: A Laboratory Manual (Cold Spring Harbor Laboratory, New York 1988 555-612). Such immunoassays include antibody capture assays, antigen capture assays, and two-antibody sandwich assays. These assays are commonly used by those of ordinary skill in the art. In an antibody capture assay, the antigen is attached to solid support, and labeled antibody is allowed to bind. After washing, the assay is quantitated by measuring the amount of antibody retained on the solid support. A variation of this assay is a competitive ELISA wherein the antigen is bound to the solid support and two solutions containing antibodies which bind the antigen, for example, serum from an Ebola virus vaccinee and a monoclonal antibody of the present invention, are allowed to compete for binding of the antigen. The amount of monoclonal bound is then measured, and a determination is made as to whether the serum contains anti Ebola GP antibodies. This competitive ELISA can be used to indicate immunity to known protective epitopes in a vaccinee following vaccination.

In an antigen capture assay, the antibody is attached to a solid support, and labeled antigen is allowed to bind. The unbound proteins are removed by washing, and the assay is quantitated by measuring the amount of antigen that is bound. In a two-antibody sandwich assay, one antibody is bound to a solid support, and the antigen is allowed to bind to this first antibody. The assay is quantitated by measuring the amount of a labeled second antibody that can bind to the antigen.

These immunoassays typically rely on labeled antigens, antibodies, or secondary reagents for detection. These proteins can be labeled with radioactive compounds, enzymes, biotin, or fluorochromes. Of these, radioactive labeling can be used for almost all types of assays and with most variations. Enzyme-conjugated labels are particularly useful when radioactivity must be avoided or when quick results are needed. Biotin-coupled reagents usually are detected with labeled streptavidin. Streptavidin binds tightly and quickly to biotin and can be labeled with radioisotopes or enzymes. Fluorochromes, although requiring expensive equipment for their use, provide a very sensitive method of detection. Antibodies useful in these assays include monoclonal antibodies, polyclonal antibodies, and affinity purified polyclonal antibodies. Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al., 1976 (Clin. Chim. Acta 70:1-31), and Schurs, A. H. W. M., et al. 1977 (Clin. Chim Acta 81:1-40). Coupling techniques mentioned in the latter are the glutaraldehyde method, the periodate method, the dimaleimide method, and others, all of which are incorporated by reference herein.

The language "biological sample" is intended to include biological material, e.g. cells, tissues, or biological fluid. By "environment sample" is meant a sample such as soil and water. Food samples include canned goods, meats and others.

Yet another aspect of the present invention is a kit for detecting ESB virus in a biological sample. The kit includes a container holding one or more antibodies which binds an epitope of ESB GP and instructions for using the antibody for the purpose of binding to ESB GP to form an immunological complex and detecting the formation of the monoclonal antibodies of immunological complex correlates with presence or absence of ESB virus in the sample. Examples of containers include multiwell plates which allow simultaneous detection of ESB virus in multiple samples.

Given these results, monoclonal antibodies according to the present invention are suitable both as therapeutic and prophylactic agents for treating or preventing ESB infections in susceptible subjects. Subjects include rodents such as mice or guinea pigs, monkeys, and other mammals, including humans.

In general, this will compromise administering a therapeutically or prophylactically effective amount of one or more monoclonal antibodies of the present invention to a susceptible subject. Any active form of the antibody can be administered, including Fab and F(ab')2 fragments. Antibodies of the present invention can be produced in any system, including insect cells, baculovirus expression systems, chickens, rabbits, goats, cows, or plants such as tomato, potato, corn, banana or strawberry.

Methods for the production of antibodies in these systems are known to a person of ordinary skill in the art. Preferably, the antibodies used are compatible with the recipient species such that the immune response to the MAbs does not result in clearance of the MAbs before the virus can be controlled, and the induced immune response to the MAbs in the subject does not induce "serum sickness" in the subject. Preferably, the MAbs administered exhibit some secondary functions such as binding to Fc receptors of the subject.

Treatment of individuals having ESB infection may compromise the administration of a therapeutically effective amount of ESB antibodies of the pre present invention. The antibodies can be provided in a kit as described herein. The antibodies can be used or administered as a mixture, for example in equal amounts, or individually, provided in sequence, or administered all at once. In providing a patient with antibodies, or fragments thereof, capable of binding to ESB GP, or an antibody capable of protecting against ESB virus in a recipient patient, the dosage of administered agent will vary depending upon such factors as the patient's age, weight, height, sex, general medical condition, previous medical history, etc.

Active immunization can be induced by administering one or more antigenic and/or immunogenic epitopes as a component of a subunit vaccine. Vaccination could be performed orally or parenterally in amounts sufficient to enable the recipient to generate protective antibodies against the biologically functional region, prophylactically or therapeutically. The host can be actively immunized with the antigenic/immunogenic peptide in pure form, a fragment of the peptide, or a modified form of the peptide. One or more amino acids, not corresponding to the original protein sequence can be added to the amino or carboxyl terminus of the original peptide, or truncated form of the peptide. Such extra amino acids are useful for coupling the peptide to another peptide, to a large carrier protein, or to a support. Amino acids useful for these purposes include: tyrosine, lysine, glutamic acid, aspartic acid, cysteine and derivatives thereof. Alternative protein modification techniques may be used, e.g., NH2-acetylation or COOH-terminal amidation, to provide additional means for coupling or fusing the peptide to another protein or peptide molecule or to a support.

The antibodies capable of protecting against ESB virus are intended to be provided to recipient subjects in an amount sufficient to effect a reduction in the ESB virus infection symptoms. An amount is said to be sufficient to "effect" the reduction of infection symptoms if the dosage, route of administration, etc. of the agent are sufficient to influence such a response. Responses to antibody administration can be measured by analysis of subject's vital signs.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

The compounds of the present invention can be formulated according to known methods to prepare pharmaceutically useful compositions. Suitable vehicles and their formulation, inclusive of other human proteins, e.g., human serum albumin, are described in Remington's Pharmaceutical Sciences ($16^{th}$ ed. Osol, A. ed., Mack Easton Pa. (1980)). In order to form a pharmaceutically acceptable composition suitable for effective administration, such compositions will contain an effective amount of the above-described compounds together with a suitable amount of carrier vehicle. Additional pharmaceutical methods may be employed to control the duration of action. Control release preparations may be achieved through the use of polymers to complex or absorb the compounds. The controlled delivery may be exercised by selecting the appropriate macromolecules (for example polyesters, polyamino acids, polyvinyl, pyrrolidone, ethylenevinylacetate, methylcellulose, carboxymethylcellulose, or protamine sulfate) and the concentration of macromolecules as well as the method of incorporation in order to control release. Another possible method to control the duration of action by controlled release preparations is to incorporate the compounds of the present invention into particles of a polymeric material such as polyesters, polyamino acids, hydrogels, poly(lacticacid) or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly(methylmethacylate)-microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

Administration of the antibodies disclosed herein may be carried out by any suitable means, including parenteral injection (such as intraperitoneal, subcutaneous, or intramuscular injection), in ovo injection of birds, orally, or by topical application of the antibodies (typically carried in a pharmaceutical formulation) to an airway surface. Topical application of the antibodies to an airway surface can be carried out by intranasal administration (e.g., by use of dropper, swab, or inhaler which deposits a pharmaceutical formulation intranasally). Topical application of the antibodies to an airway surface can also be carried out by 3Q inhalation administration, such as by creating respirable particles of a pharmaceutical formulation (including both solid particles and liquid particles) containing the antibodies as an aerosol suspension, and then causing the subject to inhale the respirable particles. Methods and apparatus for administering respirable particles of pharmaceutical formulations are well known, and any conventional technique can be employed. Oral administration may be in the form of an ingestable liquid or solid formulation. The treatment may be given in a single dose schedule, or preferably a multiple dose schedule in which a primary course of treatment may be with 1-10 separate doses, followed by other doses given at subsequent time intervals required to maintain and or reinforce the response, for example, at 1-4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms, or reduce severity of disease.

The present invention also provides kits which are useful for carrying out the present invention. The present kits comprise a first container containing or packaged in association with the above-described antibodies. The kit may also comprise another container containing or packaged in association solutions necessary or convenient for carrying out the invention. The containers can be made of glass, plastic or foil and can be a vial, bottle, pouch, tube, bag, etc. The kit may also contain written information, such as procedures for carrying out the present invention or analytical information, such as the amount of reagent contained in the first container means. The container may be in another container apparatus, e.g. a box or a bag, along with the written information.

While specific embodiments of the invention will be shown and described in detail to illustrate the application of the principles of the invention, it will be understood that the invention may be embodied otherwise without departing from such principles. All forthcoming examples are illustrative of the invention and should be in no way construed to be exhaustive of the possible embodiments.

EXAMPLE 1

Production and Characterization of Ebola GP MAbs

Materials and Methods
Animals.
Female BALB/c mice (5- to 8-weeks old) were obtained from the National Cancer Institute (Frederick, Md.) and housed under specific-pathogen free conditions. Research was conducted in compliance with the Animal Welfare Act and other federal statutes and regulations relating to animals and experiments involving animals and adhered to principles stated in the Guide for the Care and Use of Laboratory Animals (National Research Council, 1996). The facility where this research was conducted is fully accredited by the Association for the Assessment and Accreditation of Laboratory Animal Care International.

Vaccinations.
Balb/c mice were vaccinated subcutaneously in the dorsal neck region with Venezuelan equine encephalitis replicons (VRP) ($2\times10^6$ focus forming units (ffu)/mouse) expressing the glycoprotein of Sudan Boniface. The mice were boosted three times over consecutive months with VRP ($1\times10^7$ ffu/mouse). One month after the last subcutaneous boost, mice were intravenously injected with inactivated-irradiated Ebola virus.

Hybridoma Cell Lines.
Spleens were removed from mice 7 days after the final vaccination and splenocytes were prepared using standard techniques. Splenocytes were fused to p3X63Ag8.653 myeloma cells to produce hybridoma cell lines. Hybridoma cell lines were cultured in serum-free media (Life Technologies, Calsbad, Calif.) in INTEGRA CELLINE flasks. Antibody specificity of the supernatants of the cell lines was determined by ELISA assay against irradiated-whole Ebola Sudan Boniface virus and irradiated-whole Ebola Zaire virus. Hybridoma cell lines with a positive result by ELISA for Ebola Sudan Boniface underwent a second cloning and were reassessed for specificity by ELISA. Hybridomas of interest were cultured and supernatants were collected for 2 months. Supernatants were filtered and antibody was isolated over a protein G affinity column.

Antibody Characterization.
Antibodies were isotyped using ISOSTRIP Mouse Monoclonal Antibody Isotyping kit (ROCHE, CH). Antibody concentrations were determined by commercially available BCC test. Antibody purity was confirmed by Western blot assays against irradiated Ebola Zaire and Ebola Sudan virus. Antibody utility for flow cytometry was determined using the following method. VERO cells were infected with VRP expressing one of four different proteins (Sudan Gulu GP, Sudan Boniface GP, Zaire GP or Lassa NP) at 10-fold serial dilutions. After a 24-h incubation, cells were harvested using an EDTA/PBS solution and incubated with serial 10-fold dilutions of the various hybridoma antibodies. After incubation, cells were stained with secondary FITC-labeled goat-anti mouse IgG. Samples were analyzed by flow cytometry for specificity against different viral proteins. To determine the epitope sequence of the Ebola glycoprotein to which the antibodies were binding, we performed SPOTS membrane analysis. Thirteen-mers of synthetic peptides that covered the glycoprotein were immobilized on membranes and hybridoma antibodies were added. Horseradish peroxide secondary antibody with addition of a conjugate was utilized to visualize positive results. This technique was only useful for identifying antibodies that bind linear sequences of the viral protein.

A summary of Sudan murine antibodies utility in flow cytometry is described in FIGS. 1-4. These FIGs demonstrate graphically the results that were obtained when Vero cells were infected with VRP expressing the different viral proteins. After a 24-h incubation, cells were incubated with the indicated primary antibody at the specified concentrations and a goat-anti mouse IgG FITC-conjugated secondary antibody.

Figure 5:
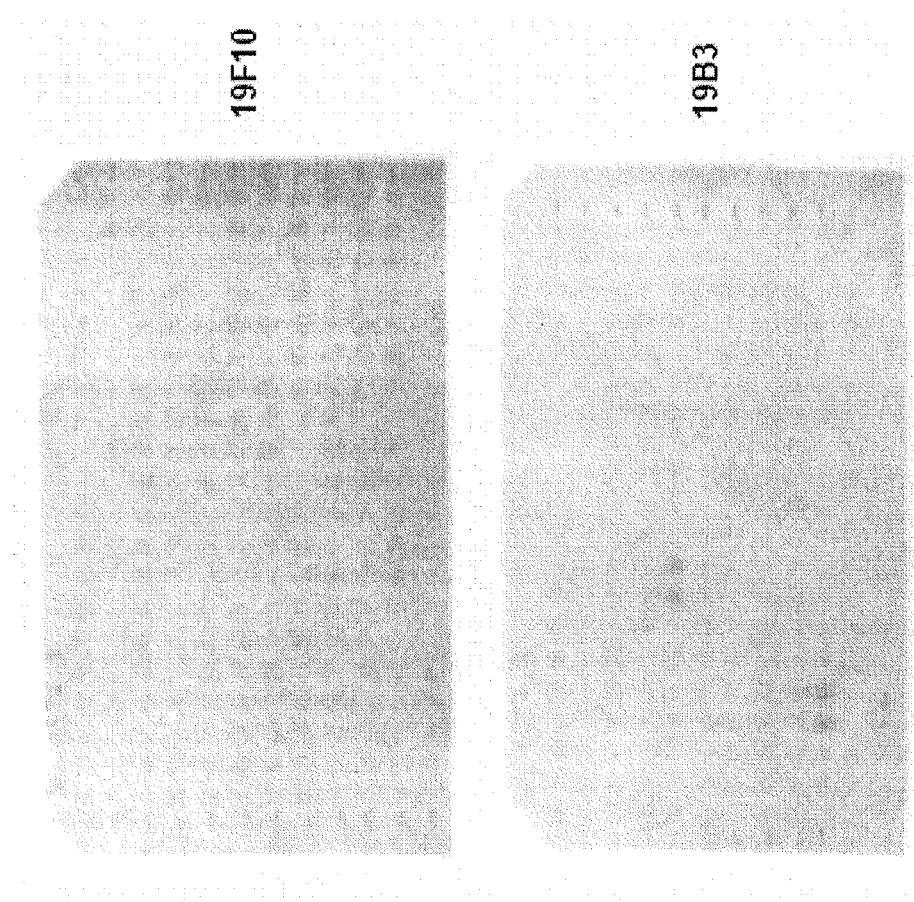
FIG. 5 is a photograph of 96-well nitrocelluslose plates containing overlapping 13-mer peptides of Ebolda Sudan GP incubated from antibodies generated from the 19F10 and 19B3 hybridomas. Dark spots indentify the linear sequence of binding by indirect immunochemical means.
Figure 6:
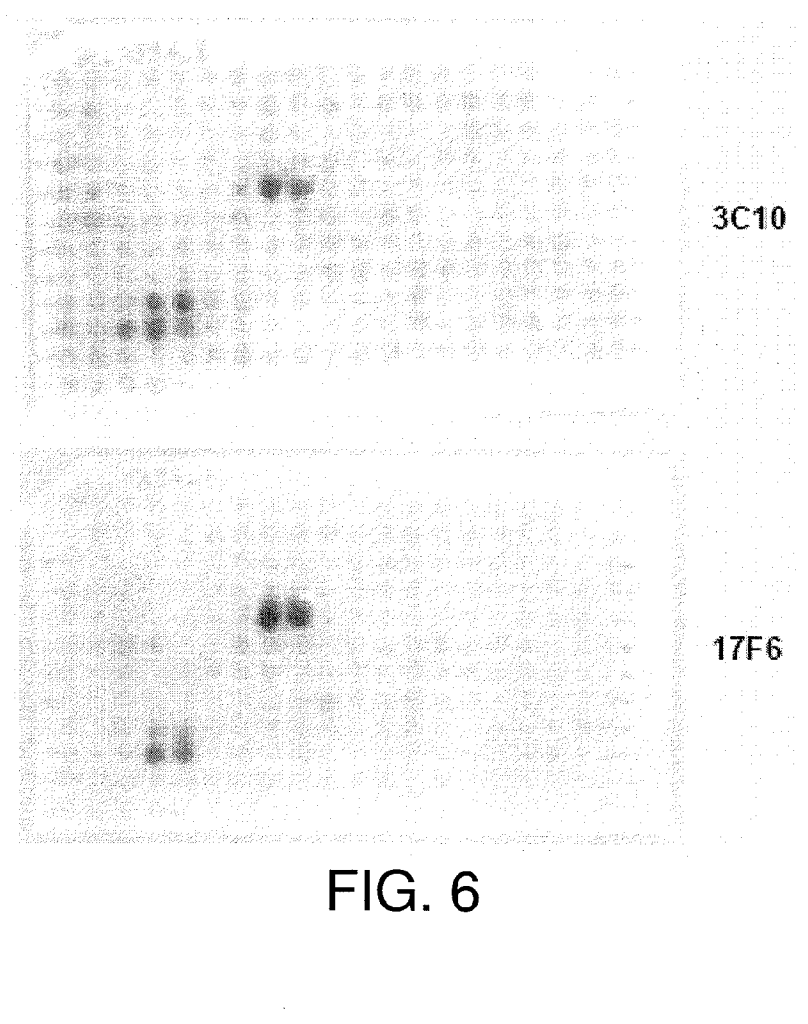

FIGS. 5-6 show the results of the use of SPOTS membranes for determining antibodies with linear epitope specificity. Overlapping 13-mer peptides of Ebola Sudan GP were coated onto 96-well nitrocellulose plates. Antibodies were incubated and secondary antibody was added for detection. Dark spots indicate wells where the specific antibody bound, thus identifying the linear sequence of binding.

FIG. 7 is a table showing the overview of the experimental results of Example 1.

EXAMPLE 2

Competitive Binding of Ebola Mabs and Protective Efficacy of Ebola GP MAbs In Vivo Materials and Methods
Animals.
Female BALB/c mice and severe combined immunodeficiency (SCID) mice (5- to 8-weeks old) were obtained from the National Cancer Institute, Frederick, Md. and housed under specific-pathogen-free conditions. Research was conducted in compliance with the Animal Welfare Act and other federal statutes and regulations relating to animals and experiments involving animals and adhered to principles stated in the Guide for the Care and Use of Laboratory Animals (National Research Council, 1996). The facility where this research was conducted is fully accredited by the Association for the Assessment and Accreditation of Laboratory Animal Care International.

Vaccinations for Antibody Generation.

Balb/c mice were vaccinated subcutaneously in the dorsal neck region with Venezuelan equine encephalitis replicons (VRP) ($2\times10^6$ focus-forming units (ffu)/mouse) expressing the glycoprotein of Sudan Boniface. The mice were boosted three times over consecutive months with VRP ($1\times10^7$ ffu/mouse). One month after the last subcutaneous boost, mice were intravenously injected with inactivated-irradiated Ebola virus.

Hybridoma Cell Lines.

Spleens were removed from mice 7 days after the final vaccination and splenocytes were prepared using standard techniques. Splenocytes were fused to p3X63Ag8.653 myeloma cells to produce hybridoma cell lines. Hybridoma cell lines were cultured in serum-free media (LIFE TECHNOLOGIES) in INTEGRA CELLINE flasks. Antibody specificity of the supernatants of the cell lines was determined by ELISA assay against irradiated-whole Ebola Sudan Boniface virus and irradiated-whole Ebola Zaire virus. Hybridoma cell lines with a positive result by ELISA for Ebola Sudan Boniface underwent a second cloning and were reassessed for specificity by ELISA. Hybridomas of interest were cultured and supernatants were collected for two months. Supernatants were filtered and antibody was isolated over a protein G affinity column. Prior to characterization, these monoclonal antibodies were confirmed for Sudan specificity by ELISA.

Antibody Characterization.

Antibodies were isotyped using ISOSTRIP Mouse Monoclonal Antibody Isotyping kit (ROCHE, CH). Antibody concentrations were determined by commercially available BCA test (THERMO FISHER SCIENTIFIC, Rockford, Ill.). The purity of the monoclonal was confirmed by electrophoresis using Tris-Glycine SDS-Polyacrylamide gel. Further characterization was performed by Western Blot assays against irradiated Ebola Zaire and Ebola Sudan viruses. To determine the epitope sequence of the Ebola glycoprotein to which the antibodies were binding, we performed SPOTS membrane analysis. Thirteen-mers of synthetic peptides (MIMOTOPES) overlapping by five amino acids that covered the glycoprotein were immobilized on cellulose membranes and hybridoma antibodies were added. Beta-galactosidase conjugate secondary antibody was used to visualize positive results. This technique was only useful for identifying antibodies that bind linear sequences of the viral protein.

Plaque Assays.

100 ug/ml of monoclonal antibodies were mixed with 100 plaque-forming units of Ebola Sudan at 37° C. for 1 hour in the presence or absence of 5% guinea pig complement (CEDERLANE, Burlington, Calif.). Vero cells monolayers were overlaid with agarose. A second overlay containing 5% agarose was added 7 days later and plaques were counted the next day. Neutralization was determined by 80% plaque reduction compared with controls.

In Vivo Activity.

SCID mice were challenged with a homogentate of livers and spleens from mice by Intraperitoneal route with passaged-Sudan virus, which is historically lethal in SCID mice in 16-18 days post infection. Following challenge mice were treated with 100/ug of 16F6 monoclonal antibody on day 5, 10, 15 and 20 diluted in 200 ul of PBS. Mice were monitored daily for morbidity and mortality. Time to death was determined for the treated mice and compared to untreated and mock treated controls to determine statistical significance.

FIG. 8 is a table showing the overview of the experimental results of Example 2.

A summary of Sudan murine antibodies utility in flow cytometry is described in FIGS. 1-4. These FIGs demonstrate graphically the results that were obtained when Vero cells were infected with VRP expressing the different viral proteins. After a 24-h incubation, cells were incubated with the indicated primary antibody at the specified concentrations and a goat-anti mouse IgG FITC-conjugated secondary antibody.

Figure 9:
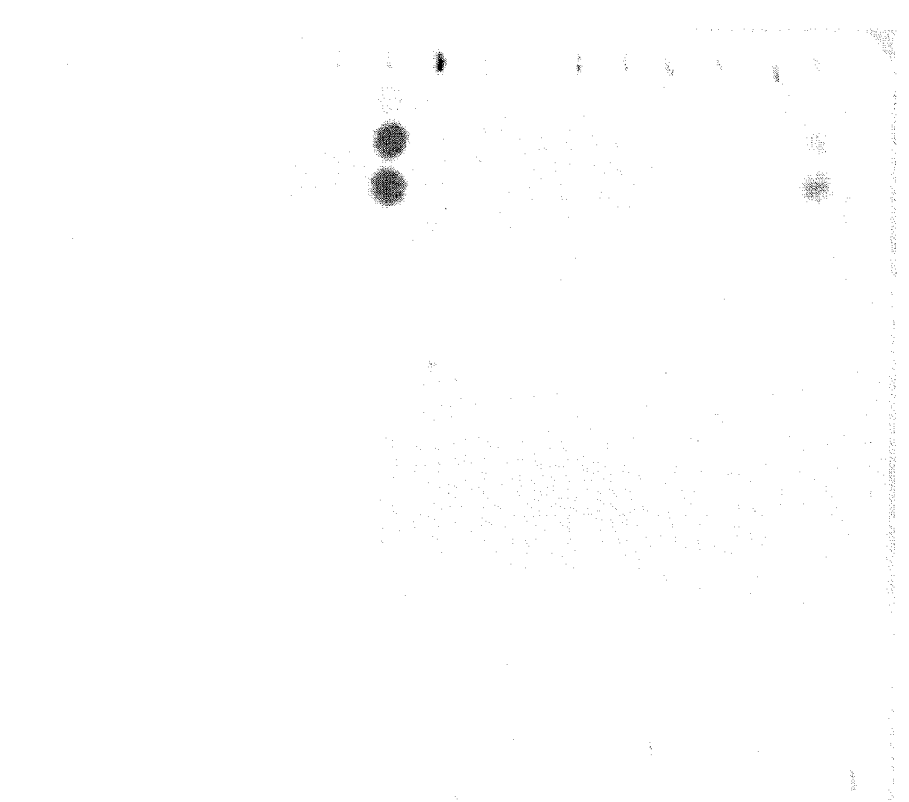
FIG. 9 is a photograph of 96-well nitrocelluslose plates containing overlapping 13-mer peptides of Ebolda Sudan GP incubated from antibodies generated from the 5B4 hybridoma. Dark spots identify the linear sequence of binding by indirect immunochemical means.

The photograph in FIG. 9 shows the results of the use of SPOTS membranes for determining antibodies from the 5B4 hyrbidoma with linear epitope specificity. Overlapping 13-mer peptides of Ebola Sudan GP were coated onto 96-well nitrocellulose plates. Antibodies form the 5B4 hybridoma were incubated and secondary antibody was added for detection. Dark spots indicate wells where the specific antibody bound, thus identifying the linear sequence of binding.

Figure 10:
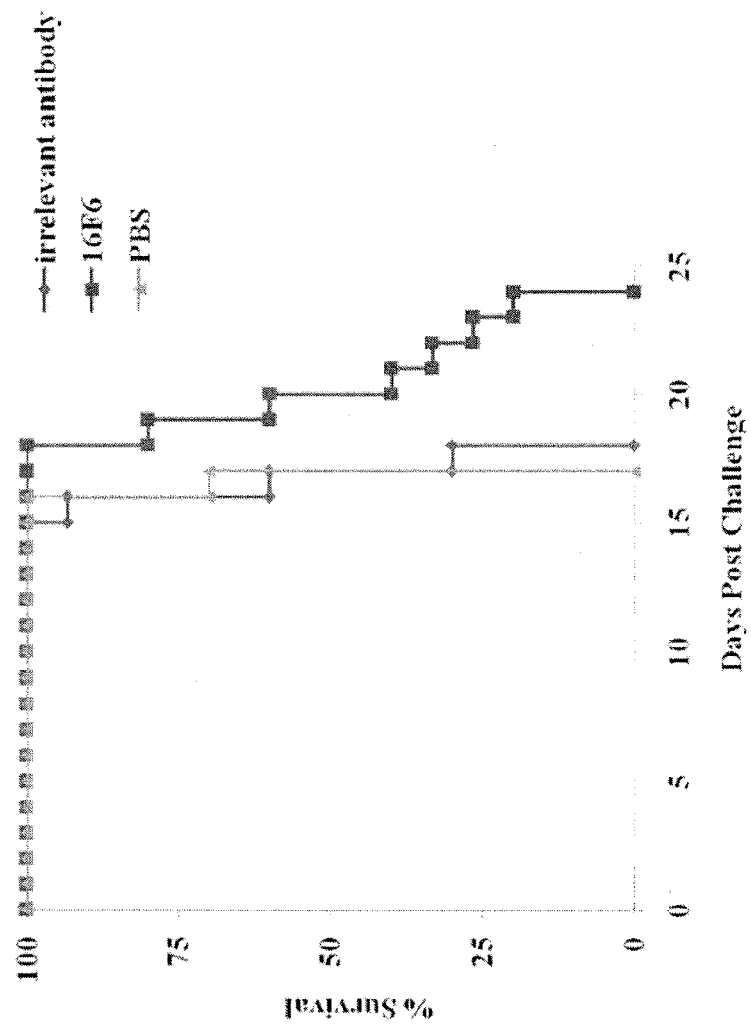
FIG. 10 is a graph showing in vivo activity of 16F6 Sudan monoclonal antibody in SCID mice.

In FIG. 10 we see the In Vivo Activity Of 16F6 Sudan Monoclonal Antibody in SCID Mice. SCID mice were infected IP with ~500 pfu of "SCID-adapted" Ebola Sudan homogenate. At 5, 10, 15 and 20 days post challenge, groups of SCID mice were treated IP with 100 ug of either 16F6, a Sudan specific antibody, or 13C6, an irrelevant Ebola Zaire specific antibody, (n=15) or PBS (n=10) in volume of 200 ul. Mice were monitored for 25 days for morbidity and mortality. The data is presented on a Meier-Kaplan curve as percent survival for each group. A t-test showed a significant difference in mean time-to-death between those that received 16F6 when compared to those that PBS or the irrelevant antibody, p<0.0001 for each comparison group.

EXAMPLE 3

Characterization of ESB MAbs Demonstrating In Vitro Neutralization of ESB Virus

Materials and Methods

Four Balblc mice were vaccinated by subcutaneous route with $1\times10^7$ ffu of Sudan Boniface glycoprotein (GP) expressed by Venezuelan equine encephalitis virus replicon developed and prepared at the United States Army Medical Research Institute of Infectious Diseases (USAMRIID). Mice were boosted with the same dose of the same construct three times at one month intervals. Mice were boosted one final time with irradiated Ebola Sudan Boniface virus by tail vein injection. Four days following final injection, mice were harvested and spleens were fused with an immortalized cell line to create hybridoma fusions. Hybridoma plasma cells secreting glycoprotein (GP) specific monoclonal antibodies were isolated and confirmed by Enzyme linked Immunosorbant Assay (ELISA) against irradiated Ebola Sudan Boniface virus. Eighteen Sudan OP-specific antibodies of the IgG isotype have been identified as the 18 Sudan hybridoma cells producing the monoclonal antibodies are hereby disclosed. The sequence to which some of these monoclonal antibodies are directed within the glycoprotein itself has been identified (SEQ ID NO. 19). Several of these monoclonals can neutralize Sudan virus in culture (SEQ ID NOS. 1-12).

Murine monoclonal antibodies directed against the glycoprotein (GP) of Boniface that were generated through vaccination with Venezuelan equine encephalitis virus replicons (VRP). IgG monoclonals specific for Boniface and Gulu strains were identified by ELISA and western blot. The majority of these monoclonals were IgG1 isotype; however, we also identified three IgG2a and one IgG2b isotypes. After infecting VERO cells with VRP expressing the GP of Boniface or Gulu, we showed the utility of three of these antibodies by flow cytometry. Sequences of the GP to which these antibodies were binding were determined by utilizing SPOTs membranes.

EXAMPLE 4

Characterization of ESB MAb 16F6 Structure

We disclose herein the structure of MAb 16F6 that neutralizes Sudan ebolavirus and present its crystal structure in complex with a trimeric Sudan glycoprotein GP linked to the largest outbreak of Ebola hemorrhagic fever recorded. Unexpectedly, the epitope of 16F6 overlaps that of KZ52, the only other antibody to be structurally characterized. Despite the distinct origins and species reactivity of these antibodies, the similarity of their GP1/GP2-bridging epitopes suggests that this could be a predominant neutralization site on the heavily carbohydrate-cloaked filovirus GP core. Further, we find that antibodies against this shared "sweet spot" neutralize similarly, at a post-internalization step.

In order to generate antibodies specific for SEBOV, we immunized BALB/c mice with Venezuelan equine encephalitis virus replicons bearing SEBOV GP (strain Boniface), followed by a final boost with radiation-inactivated Sudan ebolavirus (also Boniface). Monoclonal antibodies from the resulting hybridomas were analyzed for reactivity against irradiated SEBOV by Western blot and ELISA. Among the antibodies identified, $IgG_1$ 16F6 is directed against a conformational epitope on GP, is specific for the Sudan species, and is able to react with both the Boniface and Gulu strains. In order to map the epitope and understand the SEBOV-specificity of 16F6, we crystallized a trimeric complex of SEBOV GP (strain Gulu) and the 16F6 Fab fragment.

Crystal Structure of the 16F6-Sudan ebolavirus Gulu GP Complex.

The Gulu strain of SEBOV was chosen for structural study to reflect a modern, circulating sequence linked to the largest outbreak of Ebola hemorrhagic fever yet recorded. Gulu GP was expressed for crystallization by transient transfection of human embryonic kidney 293T cells and was purified by anti-HA affinity chromatography using previously described strategies (21). The transmembrane domain and a heavily glycosylated, unstructured mucin-like domain, which is not required for any of attachment, fusion or entry (17, 22-24), were excised from the construct in order to optimize expression and homogeneity. No mutations to N-linked glycosylation sites were necessary, such as those required to improve diffraction of ZEBOV GP (at Asn40 and Asn228). Rather, mutation of N-linked glycosylation sites in SEBOV GP accelerated GP degradation and did not improve expression yields. The differing requirements for glycosylation of the two species may relate to observed differences in stability of the different glycoproteins and species pathogenicity.

SEBOV GP-16F6 Fab complexes were purified by gel filtration and crystallized at pH 8.4, in 15% PEG 3350, 0.2 M Lithium Citrate and 1% benzamidine hydrochloride (as an additive to promote crystal nucleation and growth). In contrast to the previously determined ZEBOV GP structure, which was crystallized in space group R32 with four monomeric GP-Fab complexes per asymmetric unit (25), Sudan GP-16F6 crystallizes in the space group I23 with just one monomeric GP-Fab complex in the asymmetric unit. Hence, each Sudan GP monomer is identical and the biologically relevant trimer is formed by crystallographic symmetry. In general, the Sudan crystals are better ordered with improved electron density over those observed for a previous structure of Zaire GP (25).

Figure 11:
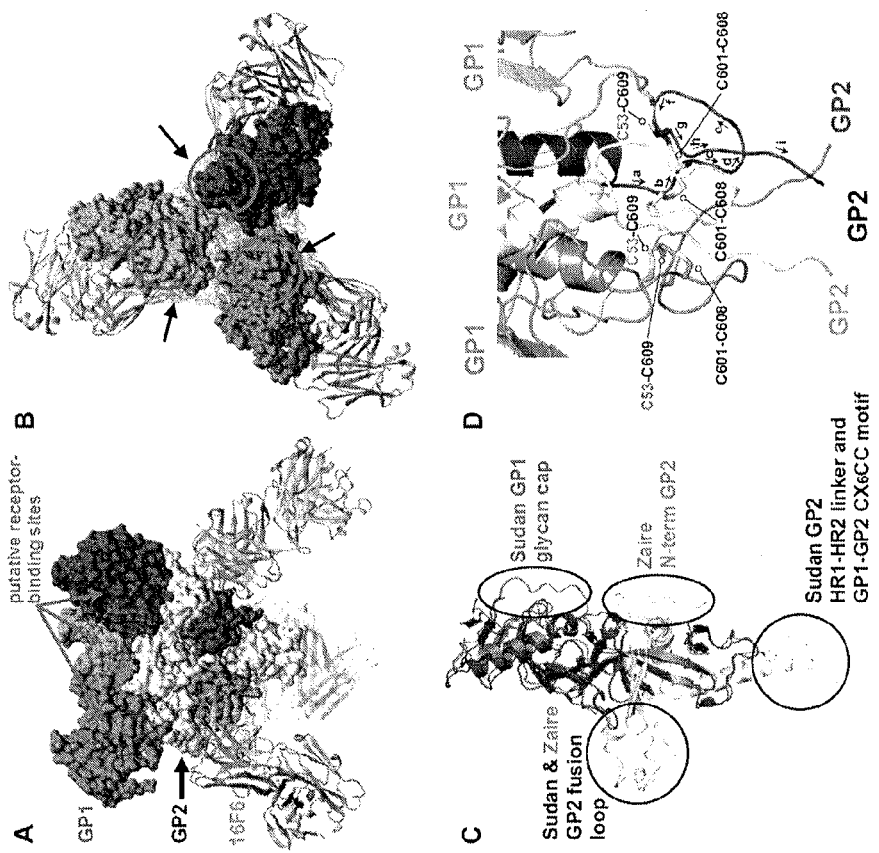
FIG. 11 is Structure of Sudan ebolavirus GP in complex with Fab 16F6. GP1 subunits (dark grey molecular surface), GP2 subunits (white molecular surface), and bound 16F6 Fab fragments (light grey strand) are shown. (A) Side view with viral membrane toward bottom and target cell toward the top. Note that 16F6 binds the base of the GP peplomer, distal from putative receptor-binding sites. (B) Top view, from the perspective of the target cell. Putative receptor-binding sites are indicated by circles and arrows. (C) Superposition of the Sudan and Zaire ebolavirus GP monomers (indicated by circles). Sudan GP1/GP2 and Zaire GP1/GP2 are labeled. Sudan GP now shows an additional region of the glycan cap (top), the HR1-HR2 linker and the CX6CC motif (bottom). (D) The linker region between HR1 and HR2 forms two disulfide bonds per monomer: one linking GP1 to GP2 (Cys 53-Cys 609) and one within GP2 (Cys 601-Cys 608). Arrows labeled a-i may be followed to trace one disulfide-anchored lobe of the trimeric cloverleaf structure.
Figure 22:
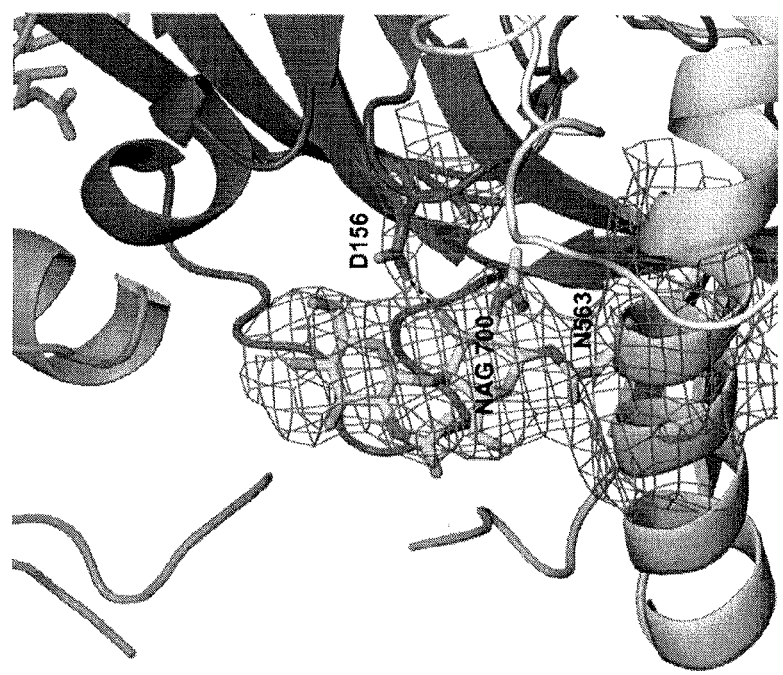
FIG. 22 is an graphical representation of electron density for glycan NAG 700-701, which is covalently linked to Asn563. The Sigma A-weighted 2Fo-Fc electron density map is contoured at 1 sigma and shown around NAG 700 in a 3 Angstrom radius for clarity of the figure. Note that OD1 of Asp 156 makes a hydrogen bond with O3 from NAG 700, helping to anchor the carbohydrate moiety to the protein core. The glycan residue is present, even after the deglycosylation treatment with PNGase-F.

The structure was determined at 3.35 Å by molecular replacement. Three antibody fragments (Fabs) are bound per GP trimer with GP in its supposed metastable, prefusion conformation (FIG. 11). The final refined SEBOV GP model comprises residues 32-192, 212-287 and 300-311 of the GP1 subunit and 510-615 of the GP2 subunit. Although GP was treated natively with peptide-N-glycosidase F (PNGase F), clear electron density is still observed for the first two monosaccharides of the glycans attached to Asn257 (NAG 350) in GP1 and Asn563 (NAG 701) in GP2 (FIG. 22), indicating that these sites, like the corresponding sites on ZEBOV GP (25), are resistant to PNGaseF digestion. Overall, the folds of SEBOV and ZEBOV GP are similar with r.m.s.d. of 1.2 Å for GP1 (alignment of 227/236 residues) and 0.9 Å for GP2 (alignment of 82/98 residues).

Newly Visualized Regions of GP.

The novel packing and improved order of these SEBOV GP-16F6 crystals allows visualization of key regions of ebolavirus GP not observed in the ZEBOV GP structure (FIG. 11C), including outer portions of the glycan cap and the functionally important linker region between the N- and C-terminal heptad repeats. This linker region contains a CX6CC motif. We now observe that first two cysteines in this motif, Cys 601 and Cys 608, form an intra-GP2 disulfide bond that anchors the intervening polypeptide in a circle looping down towards the membrane, up towards GP and down towards the membrane again (FIG. 11D). In the trimer, these three loops together assemble a three-lobed cloverleaf structure between the bulk of GP above and the C-terminal heptad repeat below. The shape and location of these regions in the structure invites speculation that each disulfide-anchored cloverleaf restricts flexibility between the N- and C-terminal heptad repeats to an elbow-like range of motion, which may be important in lifting the viral membrane-anchored C-terminal heptad repeat up toward the target cell membrane during fusion.

Further, the disulfide bond that anchors GP1 to GP2 can now be visualized at the top of each of these loops in the cloverleaf. This linkage is mediated by Cys 53 of GP1 and Cys 609 of GP2, the final Cys in the CX6CC motif of GP2 (FIG. 11D), and may serve to further restrict range of motion of the heptad repeats and anchor the prefusion GP1+GP2 trimeric assembly. The C-terminal heptad repeat is disordered, as in the ZEBOV structure, which may result from the functional mobility of this region as well as the lack of the transmembrane regions that tether GP on the viral surface.

Differences in Electrostatics Between Sudan and Zaire ebolavirus GP.

Figure 12:
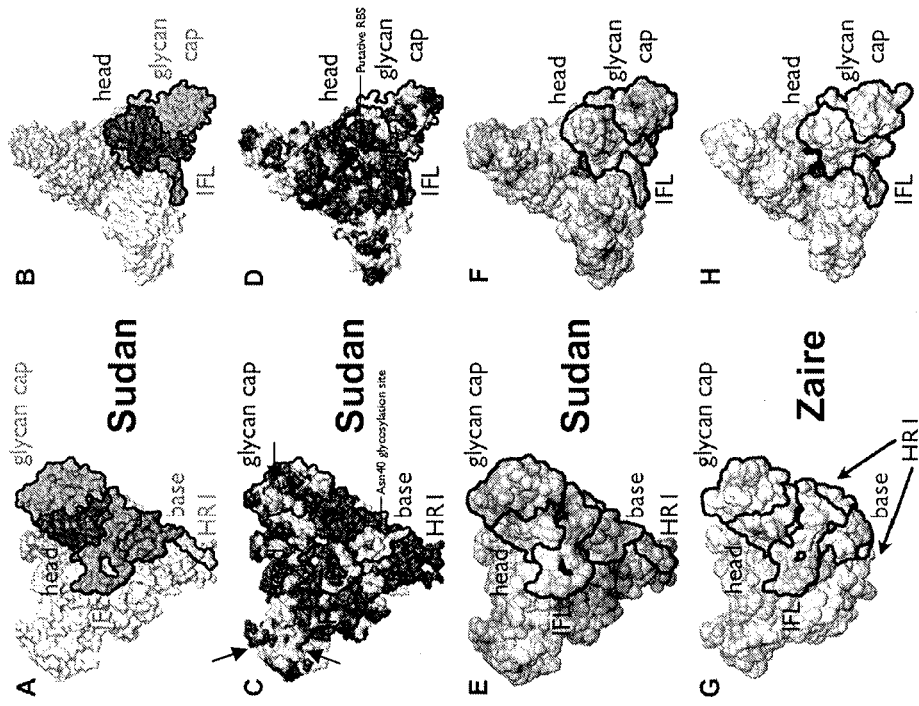
FIG. 12. Surface representation of Sudan and Zaire GPs. The domains of one GP monomer are outlined in black. (A and B) One monomer of the Sudan Gulu GP trimeric structure has different regions specifically identified (base, head, glycan cap, internal fusion loop (IFL), HR1. (C and D) Sequence conservation between Sudan and Zaire GPs. Residues that are identical between Sudan and Zaire are colored dark grey, while these that are different are colored light grey. A few residues in the glycan cap, that are entirely different, are indicated with arrows. The bottom of the IFL, the glycan cap and the base of GP1 show the most sequence diversity. (E and F) Electrostatic potential representation of the Sudan GP surface. (G and H) Electrostatic potential representation of the Zaire GP surface. A comparison of electrostatic potential maps (E and F) with (G and H) demonstrate that Sudan GP is much more negative than Zaire GP.

Visible portions of GP2 are conserved in sequence between SEBOV and ZEBOV, with the exception of the C-terminal half of the fusion loop (FIGS. 12C and 12D). Correspondingly, this half of the fusion loop adopts a different structure in SEBOV than ZEBOV (FIG. 11C). The upper half of the fusion loop (conserved) packs into the neighboring GP monomer while the lower half (variable) is free, suggesting that the conservation of the upper half of the fusion loop may reveal its importance in trimer stability or alternately, in host membrane penetration (which cannot be observed in this crystal structure).

In GP1, differences between SEBOV and ZEBOV lie throughout the glycan cap, but also occur in the head and base regions where they cluster into distinct patches. In the head subdomain, differences cluster in a ring below the putative receptor-binding site (RBS). Conserved portions of the RBS that project toward the target cell may thus provide the three-dimensional surface gripped by receptor (FIG. 12D). In the base subdomain, the outer region is conserved while the inner region varies between SEBOV and ZEBOV (FIG. 12C). On the outer face is the conserved NXT sequon for an N-linked glycosylation site at Asn 40; the conservation of this sequon throughout the EBOV genome suggests it has some functional importance. At the inner face of the base subdomain, sequence differences cluster at the attachment point of the flexible loop (residues 190-213) cleaved by cathepsins in viral entry, suggesting that there may be some functional differences in proteolytic susceptibility or enzyme recognition between the species.

Overall, the differences in sequence cause distinctly different electrostatics for the SEBOV GP trimer than the ZEBOV GP trimer. SEBOV GP is acidic overall (FIG. 12), especially in the base of the trimer where the metastable GP1-GP2 assembly intertwines. By contrast, the ZEBOV GP structure is more neutral overall, and slightly basic where GP1 and GP2 intertwine. Although the physiological manifestation of the different electrostatic profiles is not yet clear, it is possible that the intact SEBOV GP may trigger more easily through electrostatic repulsion. The acidic residues of SEBOV GP would be protonated in the low pH of the endosome, while the uncharged and basic residues of ZEBOV GP would not be protonated. Hence, SEBOV GP would be more susceptible to the effects of low pH in the endosome if acidic protons play an accessory role in facilitating conformational change after the action of other host factors.

Figure 20:
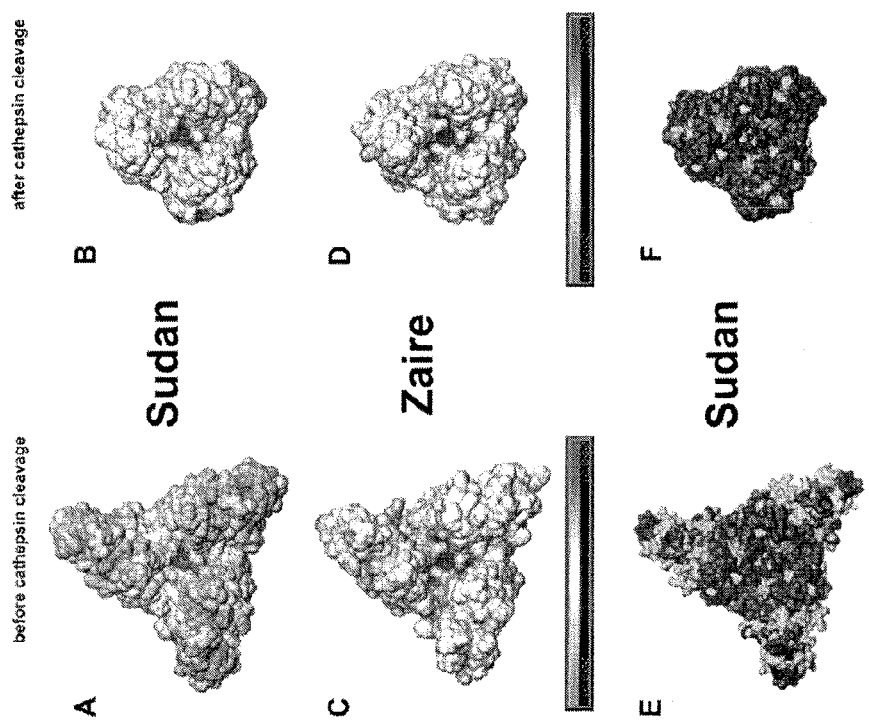
FIG. 20 is a panel of electrostatic surface representations comparing Sudan and Zaire GP before and after cathepsin cleavage. Despite the large difference in electrostatic surface properties between Sudan and Zaire GP before cathepsin, the structures show a high degree of similarity after cleavage demonstrating main core conservation across strains.
Figure 21:
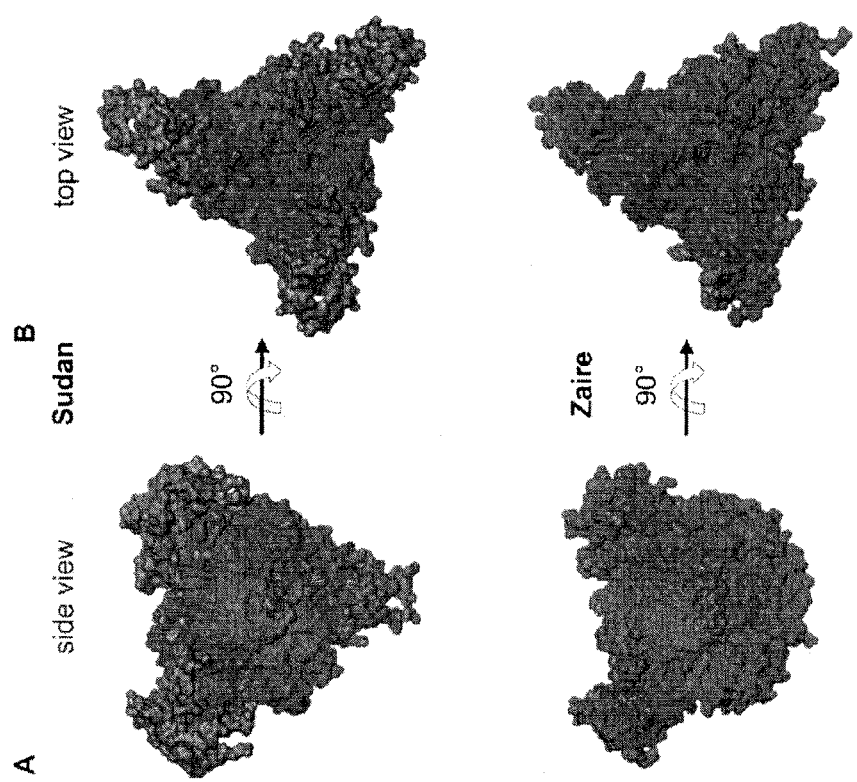
FIG. 21 is a Sudan and Zaire GP trimer surface representation of B-factor as an indication molecular flexibility. Lighter regions represent higher B-values (flexibility). The inner core of the molecule presents lower B-values, while the glycan cap and the linker region between the C-terminal heptad repeats present higher B-values. Note that some regions of Sudan have higher B-values (lighter peripheries) than that characteristic of the Zaire structure.

Although the bases and glycan caps of SEBOV and ZEBOV GP differ electrostatically, their receptor-binding regions are probably similar in charge (once the variable mucin-like domains and glycan caps are deleted by cathepsin cleavage; FIG. 20). SEBOV and ZEBOV likely bind the same receptor, and both viral species appear to present nonpolar surfaces for receptor engagement. Hence, although a trio of lysine residues cluster in the putative receptor-binding site and are important for host attachment (19), EBOV GP overall presents an uncharged surface for binding, and interactions with the as-yet unidentified receptor are likely to be mediated through a combination of van der Waals interactions and shape complementarity.

The 16F6 Epitope.

Figure 13:
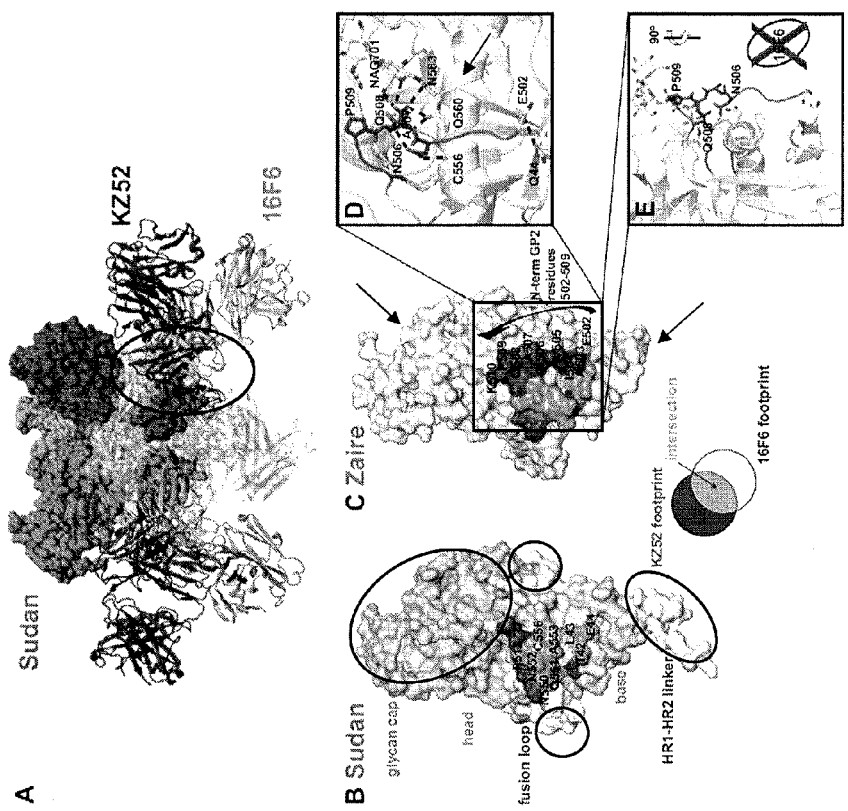
FIG. 13. (A) mAbs 16F6 and KZ52 recognize similar GP1/GP2-bridging epitopes (black oval). Here, the structure of Sudan GP in complex with 16F6 (light strands) is superimposed with the structure of Zaire GP in complex with KZ52 (dark strands). Only the Sudan GP trimer (molecular surface protein) is shown for clarity. (B) and (C) Epitope footprints of 16F6 (light grey) and KZ52 (dark grey) are mapped onto the Sudan and Zaire surfaces (see legend bottom). (B) Sudan GP surface. A single GP monomer is shown (circles). Residues shared between the two antibody epitopes (T42, L43, E44, P513, N550, Q551, N552, A553 and C556) are with the "intersection" color (see legend bottom). (C) Zaire GP surface. GP1 and GP2 are indicated with arrows. N-terminal GP2 residues are labeled. In the Sudan structure, the N terminus of GP2 is visible beginning at residue 510 (residues 502-509 are disordered). (D and E) Inset, the N-terminus of Zaire GP2 sterically blocks the would-be site of 16F6 binding underneath (indicated by arrow). Residues N506, Q508 and P509 that define the rigidity of the Zaire GP2 N terminus, bridge the HR1A helix, and help anchor the Zaire GP2 N-terminus onto the GP core. These three residues differ in sequence between the Sudan and Zaire species; this region is mobile and disordered in Sudan GP.
Figure 14:
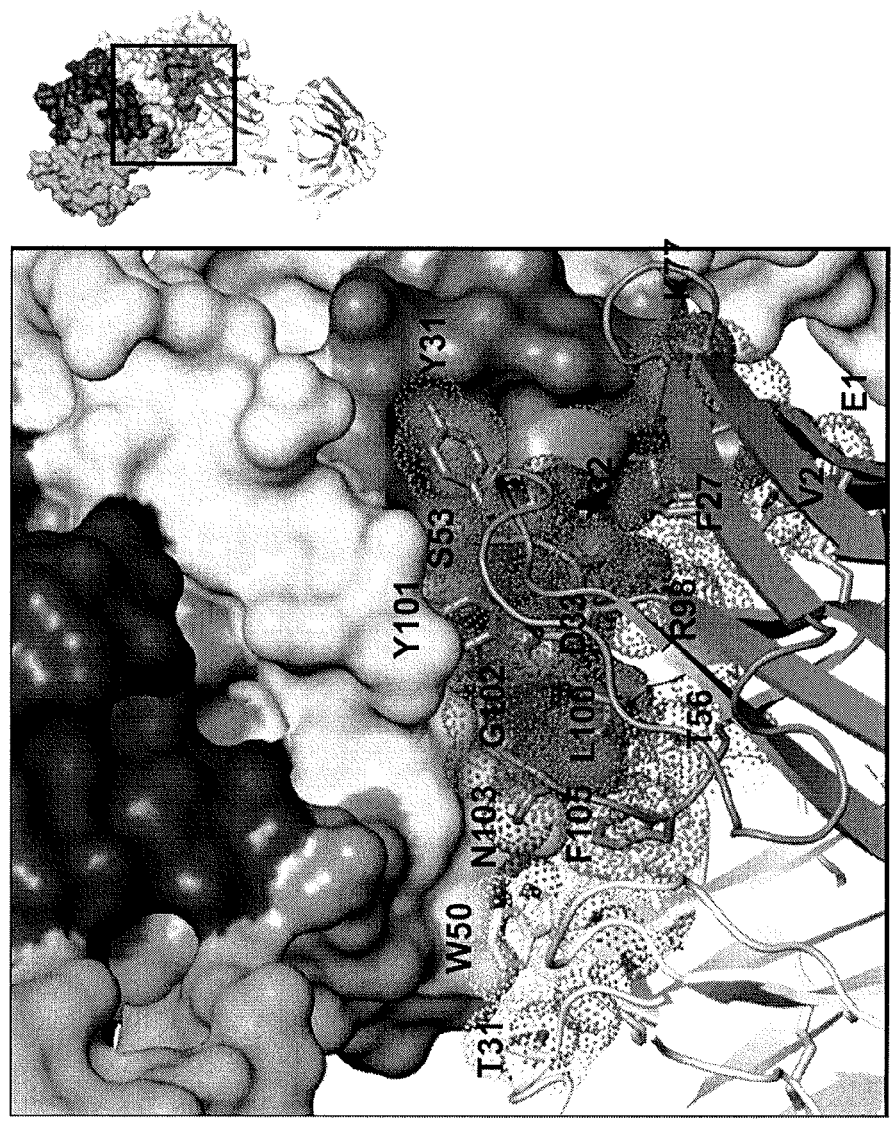
FIG. 14. The Antibody 16F6 binds the membrane-proximal side of GP. Here, one monomer of Sudan GP is shown as a molecular surface with the GP1 base, GP1 head, GP1 glycan cap, GP2 fusion loop, GP2 heptad repeat 1 shown. 16F6 is shown as a ribbon model with the heavy chain in dark grey and the light chain in light grey. The molecular surface of the 16F6 paratope is indicated by a speckled pattern and the Fab residues are labeled. Contact between 16F6 and GP is mediated by 1 salt bridge (GP1 Glu44 to CDRH3 Arg98), 9 hydrogen bonds, and 33 van der Waals contacts. The shape complementarity, Sc, is 0.61 (32). The Fab 16F6 binds to a conformational epitope that extends from the GP1 base to the GP2 heptad repeat region.
Figure 23:
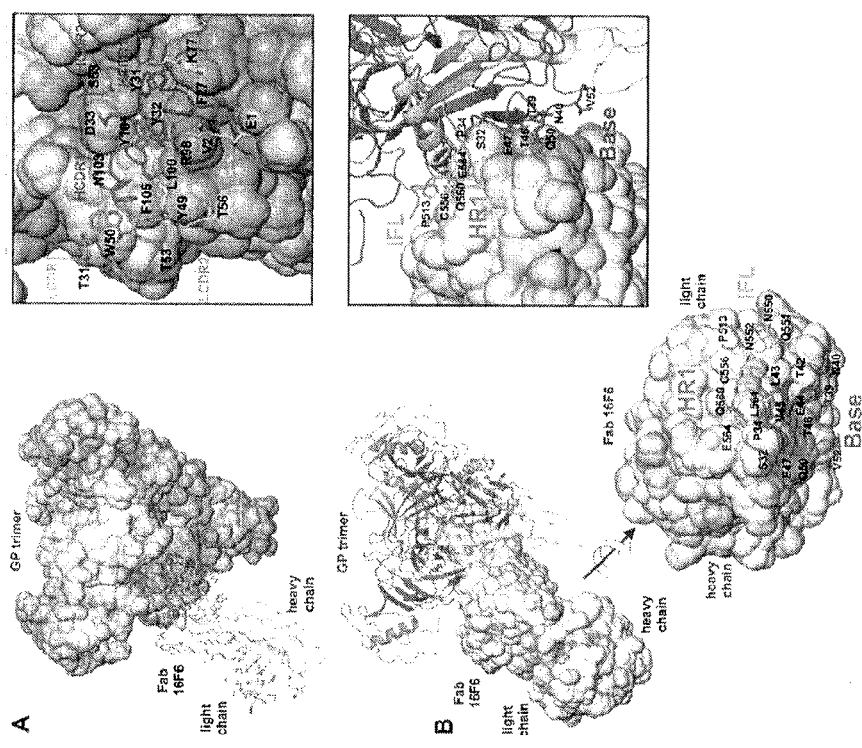
FIG. 23. (A) shows the electrostatic surface potential representation of the Sudan GP trimer. Only one Fab 16F6 is represented for clarity (ribbon) with the interacting Fab residues represented in ball-and-stick, with the CDRs labeled accordingly as HCDR1 (F27, Y31, Y32, D33), HCDR2 (S53), HCDR3 (R98, L100, Y101, N103, F105), LCDR1 (T31), LCDR2 (Y49, W50, T53), LCDR3 and three residues from the framework (E1, V2, T56); (B) shows the electrostatic surface potential representation of the 16F6 Fab with the Sudan GP trimer in ribbon. The GP2 epitope is represented in ball-and-stick. Residues of GP that interact with the Fab are labeled: Base (S32, P34, T39, N40, T42, L43, E44, V45, T46, E47, Q50, V52); IFL (P513, N550, Q551); and HR1 (N552, A553, C556, G557, Q560, L561, E564). The right panel insets show key interacting residues of the 16F6 Fab and the Sudan GP.

In EBOV GP assembly, the internal hydrophobic fusion loop and the first heptad repeat of GP2 wrap around the base of the GP1 subunit. The crystal structure reveals that mAb 16F6 binds this site where GP1 and GP2 meet, and 16F6 directly bridges the base of GP1 to the stem of the internal fusion loop of GP2 (FIGS. 11 and 13). The complementarity determining regions (CDRs) H1 and H3 of 16F6 form a network of hydrogen bonds, van der Waals interactions and one salt bridge to the GP1 base. CDR L2 also hydrogen bonds to the GP1 base and forms additional hydrophobic interactions to the stem region of the internal fusion loop of GP2 (FIGS. 14 and 23). The proportional distribution of the total surface buried on GP by 16F6 is 56% GP1 and 44% GP2 (specifically, 819 Å$^2$ of GP1 surface and 647 Å$^2$ of GP2 surface, 1466 Å$^2$ in total).

Figure 17:
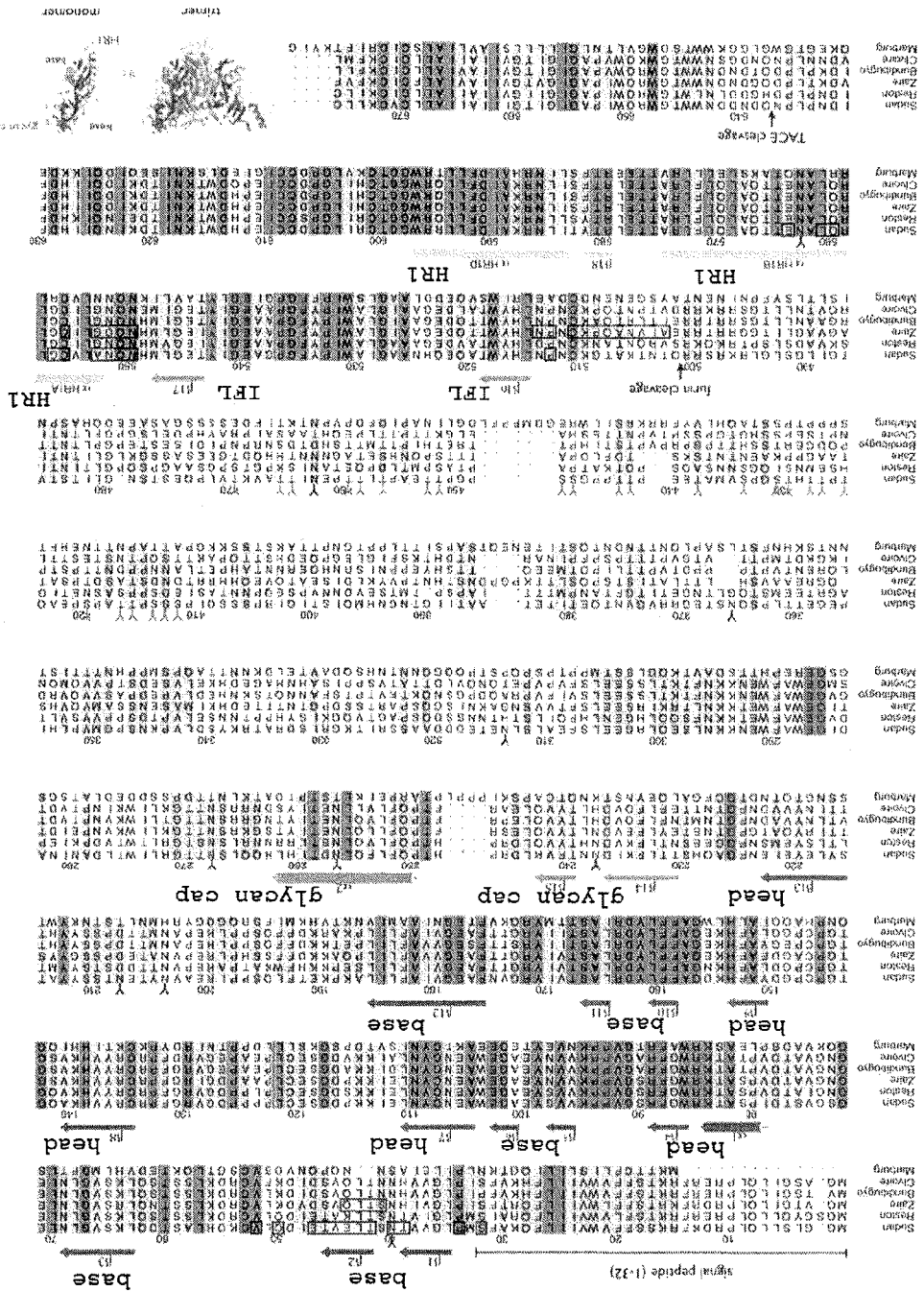
FIG. 17. Shows the alignment of GP sequences from representative filoviral species: Sudan (strain Gulu, Uganda 2000, Q7T9D9), Reston (strain Philippines, Philippines 1996, Q91DD8), Zaire (strain Mayinga, Zaire 1976, Q05320), Bundibugyo (strain Bundibugyo, Uganda 2008, ACI28624), Cote d'Ivoire (strain Cote d'Ivoire, Tai Forest 1994, Q66810) species Ebolvirus and Lake Victoria Margburvirus (strain Musoke, Kenya 1980, DQ217792). Dark grey boxes indicate conversion of residues among all species, light grey boxes indicate similar residues conservation, while no conservation among sequences is collared white. The secondary structure elements of the Sudan Gulu GP structure are indicated in text (base, head, glycan cap, internal fusion loop (IFL) and HR1 motif (HR1)). 16F6 antibody binds Sudan GP and its epitope is marked by a black box outlining the Sudan sequence. The respective KZ52 epitope is outline with a black box in the Zaire GP sequence. N-linked and O-linked glycosylation sites for Sudan ebolavirus, predicted by the NetNGlyc and NetOGlyc servers are indicated by black and grey-colored Y-shaped symbols respectively. Sugars at positions 257 and 563 are observed in the electron density maps and are resistant to PNGaseF deglycosylation. The trimeric and monomeric forms of Sudan GP are represented in the bottom right corner.
Figure 19:
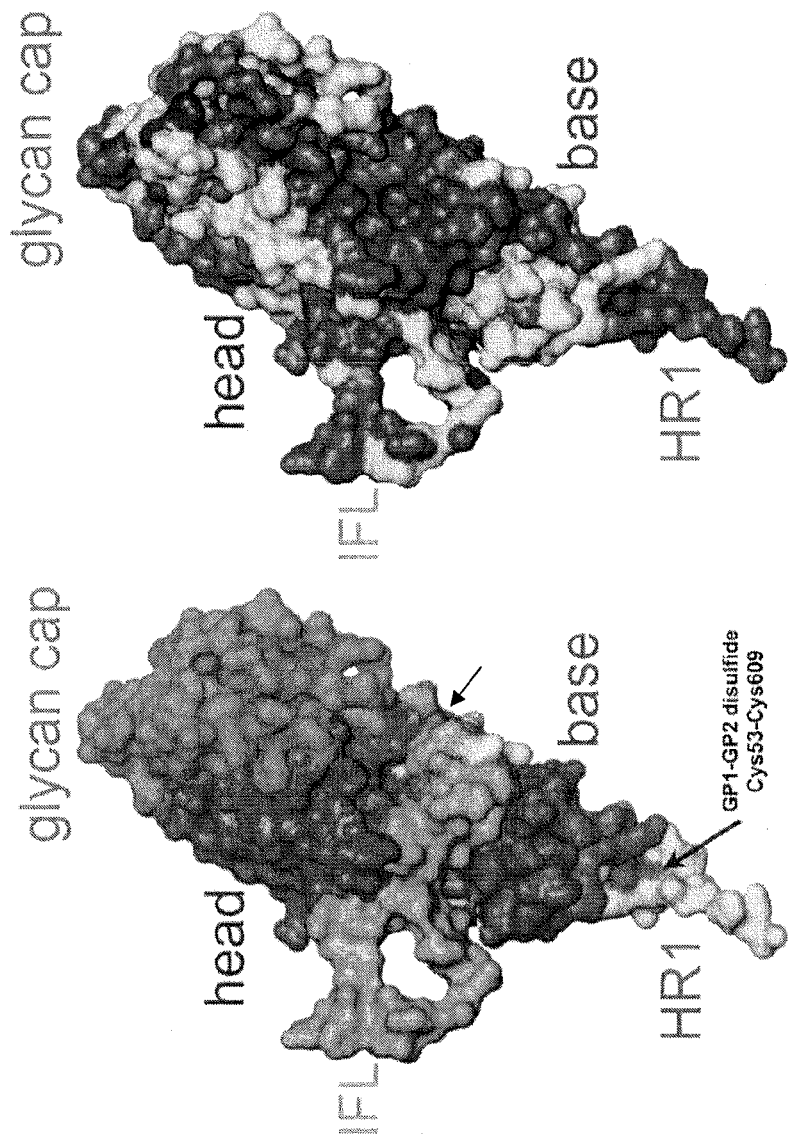
FIG. 19 is a surface representation of the GP monomer with domains labeled as indicated. On the left, the GP1-GP2 disulfide bridge and the intramolecular disulfide bridges are indicated by arrows. On the right, the surface map is colored according to sequence conservation between Sudan and Zaire GP. Dark grey coloring indicates conservation of residues among Sudan and Zaire GP, while light-grey coloring indicates similar residues conservation. The main differences occur in GP1 base and glycan cap as well as in the bottom of the GP2 IFL.

Unexpectedly, the epitope of 16F6 overlaps that of mAb KZ52, the only other antibody against the core of GP to be structurally mapped (25) (FIG. 13). KZ52 is specific for ZEBOV and was identified in a phage display library derived from a human survivor of the 1995 outbreak in Zaire (5, 6). The footprint of KZ52 on GP is shifted a bit more towards GP2 relative to the footprint of 16F6. However, both epitopes intersect where the base of GP1 meets the internal fusion loop of GP2, and the antibody epitopes have nine residues in common: 42-44 of GP1 and 513, 550-553 and 556 of GP2 (FIG. 17). Hence, although the two antibodies were raised against distinct viral species and in different immunological contexts (one by an immunized mouse, the other by a naturally infected human), these antibodies recognize overlapping epitopes and have arrived at a shared, structural solution for neutralizing ebolaviruses.

Figure 15:
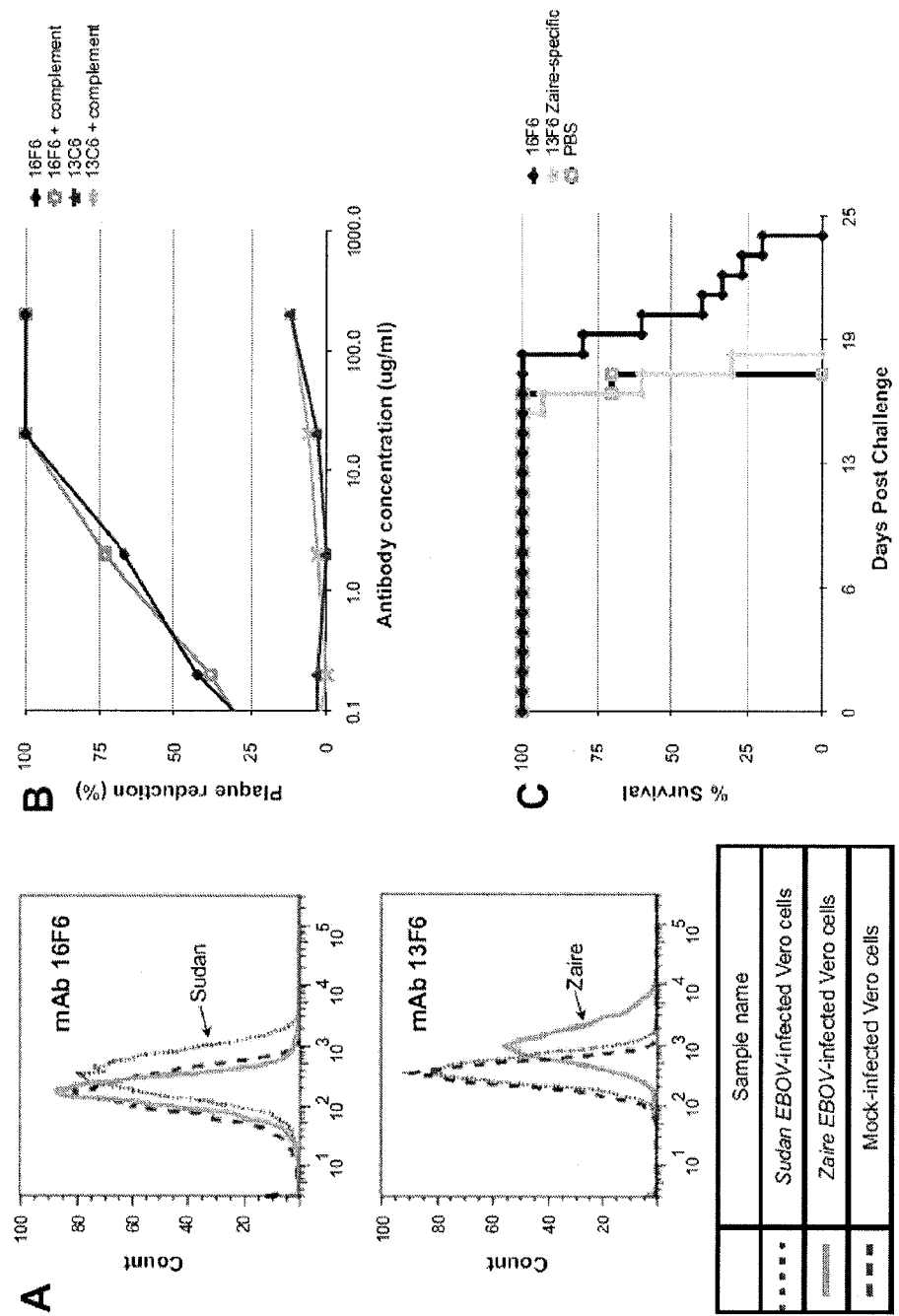
FIG. 15. Sudan ebolavirus specificity and neutralization by mAb 16F6. 13C6 and 13F6 are distinct mAbs raised vs. Zaire. 13F6 is ZEBOV-specific and directed against a linear epitope in the mucin-like domain (8, 33), while 13C6 weakly cross-reacts with SEBOV and recognizes the core of GP. (A) mAb 16F6 specifically stains Vero cells infected with SEBOV (top, dotted line), while 13F6 specifically stains Vero cells infected with ZEBOV (bottom, solid line). (B) Neutralization of SEBOV by mAb 16F6 in the presence (squares) or absence (diamonds) of complement. 90% neutralization is achieved at about 10 µg/ml 16F6. By contrast, mAb 13C6, which weakly cross-reacts with SEBOV GP (8) is non-neutralizing for SEBOV. (C) In vivo activity of mAb 16F6 in SCID mice. SCID mice were infected IP with 500 pfu "SCID-adapted" SEBOV homogenate. At 5, 10, 15 and 20 days post challenge, groups of SCID mice were treated IP with 100 ug either 16F6 or 13F6 (ZEBOV-specific), (n=15) or PBS (n=10) in volume of 200 ul. Mice were monitored for 25 days for morbidity and mortality. Data are presented on a Meier-Kaplan curve as % survival for each group. A t-test showed a significant difference in mean time-to-death between mice that received 16F6 vs. mice that received PBS or the irrelevant antibody: $p<0.0001$ for each comparison group.

Although these antibodies recognize overlapping sites with multiple residues in common, the antibodies are nonetheless species specific: 16F6 only recognizes SEBOV, while KZ52 only recognizes ZEBOV (FIG. 15). Six of these nine residues shared between their epitopes are conserved. The remaining three have only single-atom differences in side chain between SEBOV and ZEBOV and do not appear critical for determining species specificity of 16F6. For example, position 552, at the intersection of the antibody footprints, is Asn in SEBOV and Asp in ZEBOV. 16F6 forms only a hydrophobic contact to the Cb that is shared between Asp and Asn. Hence, determinants of species specificity probably lie outside the shared intersection of the epitopes.

One key structural difference that might explain the species specificity is the differential mobility of the N terminus of GP2, which is released from GP1 by furin cleavage in the producer cell. In ZEBOV, this region is well-ordered and hydrogen-bonded to the GP core (residues 506-510, FIG. 13) and KZ52 forms multiple contacts to it. By contrast, this region is disordered in the Sudan GP structure and not bound by 16F6. It may be that the GP2 N terminus is simply tacked down in the Zaire crystal structure by KZ52 binding. An alternative explanation is that the mobility of this region fundamentally differs between Sudan and Zaire, even in the absence of antibody binding. Key differences in sequence between Sudan and Zaire at this site support this hypothesis. The anchor point of the GP2 N terminus to the GP core is residue 509. At position 509, Zaire contains a proline, which may restrict mobility, while Sudan contains a glycine, which may enhance mobility. Further, residues Asn 506 and Gln 508 of Zaire use both their terminal oxygen and nitrogen atoms to form a network of hydrogen bonds to the Zaire GP core, specifically, to amino acids as well as the attached glycan of heptad repeat 1. By contrast, position 506 is Lys in Sudan Gulu (Gln in Sudan Boniface), and position 508 is Thr in both Sudan GPs (Gulu and Boniface). None of those hydrogen bonds made by Zaire are observed for Sudan, and the specific hydrogen bonds made by the side-chain oxygens of Asn 506 and Gln 508 in Zaire are not possible for the corresponding residues in Sudan.

In summary, although the two antibodies differ in their recognition of the GP2 N terminus, they fundamentally bind the same underlying site on the membrane-proximal base of the GP core, where they bridge the GP1-GP2 intersection. Indeed, this site is one of only a very few sites on the surface of GP that are not masked by carbohydrate and available for immune surveillance (20). It is possible that this site remains exposed in order to permit access by a host factor required for entry, or alternatively, it must remain unencumbered by carbohydrate in order to achieve the conformational rearrangements necessary for fusion. Perhaps this overlapping 16F6/KZ52 binding site is a "sweetspot" for ebolavirus neutralization.

EXAMPLE 5

Protective Efficacy of ESB GP MAbs In Vitro and In Vivo

16F6 Confers Protection Against Sudan Ebolavirus In Vitro and In Vivo.

In order to confirm that 16F6 recognizes conformationally native GP on the surface of infected cells (in addition to the truncated, recombinant protein used for crystallization), we infected Vero cells with SEBOV under (Bio Safety Level 4) BSL-4 conditions and performed flow cytometric analysis to assess the binding capacity of 16F6. Our data indicates that 16F6 selectively binds SEBOV-infected Vero cells over ZEBOV-infected Vero cells, while a control mAb, 13F6 (8), selectively recognizes only ZEBOV-infected cells (FIG. 15A).

Next, we performed plaque reduction neutralization tests (PRNT) with SEBOV under BSL-4 conditions to address in vitro functionality of 16F6. We determined that 16F6 confers a >90% reduction of viral plaques (100 pfu) at 20 mg/ml both in the presence or absence of complement. This data suggests that binding of 16F6 alone, in the absence of complement-mediated effects, is sufficient to block SEBOV infection in vitro (FIG. 15B).

As a lethal, wild-type mouse model is not yet available for SEBOV, we tested the in vivo effect of 16F6 in mice with severe combined immunodeficiency syndrome (SCID) infected with 500 pfu SEBOV. SCID mice were treated with 100 mg 16F6 every 5 days following infection. We found that 16F6 extends the life of SEBOV-infected SCID mice from 16.7 to 20.6 days. The increase in mean time to death of 4 days has a statistical significance of $p<0.0001$, demonstrating the in vivo functionality of 16F6 (FIG. 15C). The lack of a fully functional immune repertoire in SCID mice precludes these animals from ever being able to clear the viral infection, and thus, a delay to death in the absence of adaptive immunity is the best possible result.

EXAMPLE 6

ESB GP MAb 16F6 Versus MAb KZ53 Neutralization Study

In order for 16F6 to be considered further for medical use, it is important to determine if 16F6 offers similar or greater neutralization capacity than the well-studied KZ52 antibody. Direct comparison of the capacity of the anti-Sudan antibody to neutralize Sudan ebolavirus vs. the anti-Zaire antibody to neutralize Zaire ebolavirus is probably not meaningful because internal components of the viruses lead to different replication kinetics, unrelated to any antibody-GP binding events on the viral surface. Comparison of pseudotyped viruses (in which Sudan GP or Zaire GP were pseudotyped on the surface of otherwise identical VSV carriers) offers a comparison with fewer variables. Sudan GP-pseudotyped VSV and Zaire GP-pseudotyped VSV, each labeled with GFP, were used to infect 293 cells in the presence or absence of each antibody. We find that 100 mg/ml IgG 16F6 reduces infectivity of Sudan-pseudotyped VSV by 99%. By contrast, the same quantity of IgG KZ52 neutralizes Zaire-pseudotyped VSV by 90%, suggesting that mAb 16F6 is equal to, or even somewhat more effective against Sudan GP than KZ52 is against Zaire GP.

Neutralizing antibodies directed against HIV-1 and influenza virus often function by blocking initial attachment to target cells. Blocking may occur directly, by occupying the receptor-binding sites, or indirectly, by occupying a distal site and using the bulky antibody framework to sterically interfere with attachment (26, 27). Other neutralizing antibodies function later in the entry pathway by preventing conformational rearrangements required for entry (28). We determined at what stage of entry antibodies against the overlapping 16F6/KZ52 epitope neutralize EBOV infection.

EXAMPLE 7

Characterization of MAb 16F6/KZ52 Mechanisms of Action

16F6/KZ52 do not Block Attachment or Internalization

The 16F6/KZ52 epitopes are distal from the expected receptor-binding sites on GP1 (FIG. 11). However, as a definitive receptor is not yet known for EBOV, the precise binding sites of host receptor(s) or any other attachment factors are unclear. To determine whether 16F6 and KZ52 neutralize by blocking attachment, saturating quantities of these or irrelevant isotype-matched control antibodies were incubated with Sudan or Zaire GP-pseudotyped VSV particles (24, 29) and then allowed to bind to chilled Vero cells. Cells were washed to remove unattached virions and probed for the presence of VSV matrix protein (of attached virions). The matrix protein was indeed present even in saturating quantities of antibody, indicating that 16F6 and KZ52 do not attachment of pseudotyped VSV.

To test whether 16F6 and KZ52 block viral internalization, Vero cells were incubated at 37° C. rather than 4° C. Cells were then treated with proteinase K and washed to strip virions that had bound but not entered cells. Cell lysates were probed for the VSV matrix protein. The matrix protein was again present in cell lysates indicating that pseudotyped VSV enters cells whether or not 16F6 or KZ52 are present.

Figure 16:
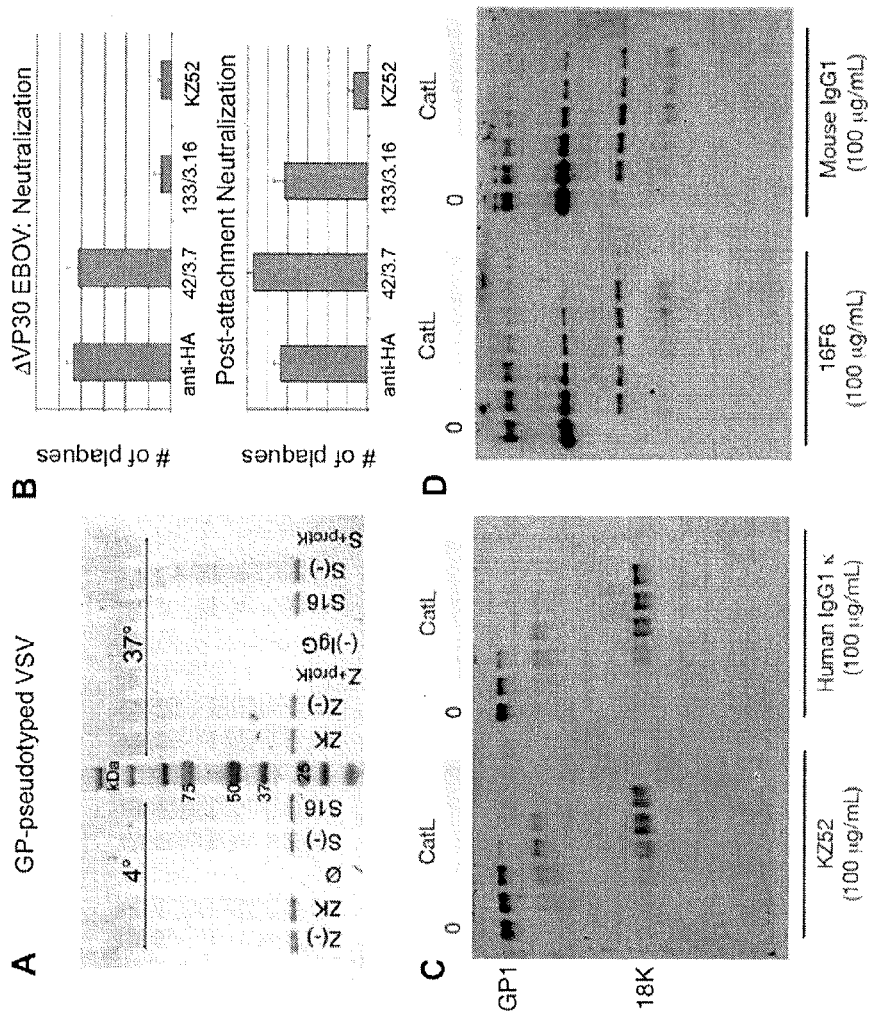
FIG. 16. 16F6 and KZ52 neutralize at a post-attachment, non-cathepsin step. (A) Left: VSV pseudotyped with ZEBOV or SEBOV GP attach to Vero cells at 4° C. in the presence of KZ52, 16F6 or a negative control anti-dengue murine IgG1 3H5. Lysates were probed for VSV M (~28 kDa). Z(-)=Zaire+3H5. ZK=Zaire+KZ52. Ø=no virions. S(-)=Sudan+3H5. S16=Sudan+16F6. Right: After attachment, cells were warmed to 37° C. to permit internalization, then treated with proteinase K to remove bound virus. Cell lysates were probed for the presence of VSV M. As a control, cold cells with bound virus were also treated with proteinase K (Z+protK or S+protK). (-) IgG is 3H5 alone. (B) Top, ΔVP30 ebolavirus in the presence of one of several antibodies was allowed to attach to Vero cells at 4° C. Cells were washed of unbound material, warmed to 37° C. and plagued. mAbs 133/3.16 and KZ52 neutralize, while 42/3.7 and anti-HA do not. Bottom: ΔVP30 ebolavirus was attached to Vero cells at 4° C., washed, incubated with mAb, washed again, warmed to 37° C. to permit internalization, and plaqued. KZ52 still neutralizes while 133/3.16 does not, indicating that KZ52 neutralizes at a post-attachment step while 133/3.16 neutralizes at the attachment step. (C and D) KZ52 and 16F6 do not prevent cleavage of virion-surface, mucin-containing GP. ZEBOV or SEBOV GP-pseudotyped VSV were incubated with increasing concentrations of CatL in the presence of KZ52 or control human IgG1 (for ZEBOV) or 16F6 or control murine IgG1 (for SEBOV).

As the packing of GP spikes on the surface of VSV pseudotypes may differ from that observed on actual EBOV, we repeated attachment assays with VP30-deleted, biologically contained ZEBOV that is identical to wild-type EBOV in morphology and GP spike density (30) (note that no similar model yet exists for the SEBOV species). Similar to our results obtained using SEBOV- and ZEBOV GP-pseudotyped VSV, biologically contained ZEBOV attaches to and enters cells (FIG. 16B). Hence, attachment assays, performed using two different experimental systems, indicate that neither 16F6 nor KZ52 function by preventing the initial steps of attachment to target cells or internalization of viral particles into the cell. Consequently, antibodies against this shared site must neutralize at a post-attachment, post-internalization step.

16F6/KZ52 do not Block Cathepsin L Cleavage

Another step in the EBOV life cycle is cleavage of GP1 by cathepsin in the endosome (16), which facilitates attachment to host factors (17, 24). Cathepsins B and L initially trim the 150 kDa GP1 monomer to a ~50 kDa species and ultimately an 18-19 kDa species of GP1. We incubated the recombinant ZEBOV and SEBOV GP used for crystallization with 1:1 and 1:10 (GP:mAb) molar ratios KZ52, 16F6 or irrelevant, isotype-matched control antibodies, and subjected the GP-antibody complexes to cleavage using 0.20 mg cathepsin L per mg GP. All antibodies, whether GE-specific or irrelevant control, slightly slowed the rate of cathepsin cleavage, but none of them prevented cathepsin cleavage. The slight slowing of the cleavage reaction may simply be the result of the presence of interfering protein in the reaction, because even irrelevant control antibody that does not bind GP slows the reaction. By 30 min and 60 min, respectively, the SEBOV and ZEBOV GPs are completely digested to ~19 kDa fragments, suggesting that 16F6 and KZ52 do not block cathepsin L cleavage of recombinant GP.

Soluble GP ectodomain may cleave differently than transmembrane-anchored GP on a viral surface. Hence, we next digested SEBOV and ZEBOV GP-pseudotyped VSV particles in the presence or absence of 16F6, KZ52, or irrelevant control antibodies. Again, we observed a slight slowing, but no prevention of cathepsin cleavage of GP in the presence of saturating quantities of 16F6 and KZ52. These data indicate that mAbs 16F6 and KZ52 do not block cathepsin cleavage of SEBOV and ZEBOV GP, whether in the context of soluble, recombinant GP or transmembrane GP borne on a VSV viral surface. Hence, it appears that 16F6 and KZ52 could function at a post-attachment step other than cathepsin cleavage.

Both 16F6 and KZ52 physically link GP1 to GP2 and are specific for the prefusion conformation of GP2. Hence, it is plausible that 16F6 and KZ52 function by locking GP into a prefusion conformation, thereby preventing fusion of viral and endosomal membranes. Indeed, recently identified antibodies capable of broad-spectrum neutralization of influenza virus similarly bind epitopes bridging the receptor binding subunit (HA1) to the fusion subunit (HA2) of the glycoprotein, are specific for the prefusion conformation of HA2, and function by blocking conformational changes of HA required for fusion (28, 31). Unfortunately, no specific fusion assay for EBOV is yet in wide use, due to a number of complications. For example, EBOV fuses with the endosomal membrane rather than the plasma membrane, cathepsin cleavage of EBOV may be required for fusion, no clear receptor for EBOV entry has yet been identified, and the identity of the precise trigger of conformational change in GP remains unknown. Indeed, GP remains in its trimeric state after proteolytic cleavage and low pH treatment. However, both KZ52 and 16F6 can be used as probes of conformational change and will be useful tools in the search for triggers of EBOV viral fusion.

Here we structurally illustrate that two out of two neutralizing antibodies directed against the EBOV GP core bind overlapping GP1/GP2-bridging epitopes. Hence, this may be a key neutralization site on the heavily carbohydrate-cloaked EBOV GP. Further, we show that antibodies at this shared site function similarly, neutralizing infection after EBOV has attached to and entered target cells. As fusion of EBOV occurs with the host endosomal membranes, and these antibodies could only bind prior to fusion and not after, 16F6 and KZ52 must neutralize in the endosome at or prior to fusion. Data shown here indicate that they do not block cleavage of GP by endosomal cathepsin L. Hence, these antibodies either block the function of an as-yet-unidentified endosomal cofactor in entry, or more likely, they block fusion itself by anchoring the prefusion conformation of GP.

In summary, we present structural and functional evidence that antibodies elicited in two unique host species by different immunological selection scenarios, bind overlapping epitopes and neutralize a virus using similar, post-internalization mechanisms. The ability of neutralizing antibodies directed against antigenically distinct viral species to nevertheless recognize a shared site suggests that this region is a key sweetspot for neutralization of ebolaviruses. Antibodies against this GP1-GP2 bridging, prefusion-specific epitope appear to function by blocking structural rearrangements of GP required for fusion with target cells. This new co-crystal structure and accompanying mechanistic analysis provide a necessary template for discovery and development of therapeutics against Sudan and other currently circulating species of ebolavirus.

EXAMPLE 8

Humanizing the Monoclonal Antibodies

To "humanize" the Mabs to be able to safely administer them to humans with a reduced chance of rejection as foreign proteins, it is necessary to sequence the variable regions of the Mabs so that the important regions involved in binding can be retained in the "humanized" product. Sequences for the heavy and/or light chain variable regions of MAbs 16H11, 19B3, 17F6, and 16F6 were determined by techniques known in the art (SEQ ID NOS. 1-12).

Using techniques currently known, these CDRs may then be generated into a backbone that is a human MAb with human framework and constant regions. Those having ordinary skill in the art of molecular biology could clone the entire variable regions onto human constant region genes to produce a chimeric mouse-human antibody. To reduce the amount of mouse sequence retained in the product (which can induce human anti-mouse responses) the CDRs can be molecularly cloned into an otherwise completely human antibody sequence. This produces a "humanized" Mab which retains only the mouse CDR sequences. Alternatively, one could use a mouse strain that has been genetically altered to produce fully human antibodies to functionally reproduce the Mabs described in this application in human form. Such mice can be obtained, for example, from Abgenix or Medarex. The use of phage display libraries, in which Mabs are derived from a human repertoire, is another way to produce the Mabs described herein in a fully human form. Screening the human Mabs for reactivity with the Ebola GP sequences SEQ ID: Nos 1-12 or by competition ELISA with the mouse Mabs described in this disclosure provides a quick, easy method of identifying Mabs with the same functional properties as ours.

REFERENCES

The contents of each of which, and the contents of every other publication, including patent publications such as PCT International Patent Publications, are incorporated herein by this reference.

1) A. Sanchez, T. W. Geisbert, H. Feldmann, in *Fields Virology*, D. M. Knipe, P. M. Howley, Eds. (Lippincott, Williams, and Wilkins, Philadelphia, 2007), pp. 1409-1448.
2) N. J. Sullivan, J. E. Martin, B. S. Graham, G. J. Nabel, *Nat. Rev. Microbiol.* 7, 8 (2009).
3) J. S. Towner et al., *PLoS Pathog* 4, e1000212 (November, 2008).
4) S. I. Okware et al., *Trop Med Int Health* 7, 1068 (December, 2002).
5) T. Maruyama et al., *J Infect Dis* 179 Suppl 1, S235 (1999).
6) T. Maruyama et al. *J Virol* 73, 6024 (1999).
7) A. Takada et al., *J Virol* 77, 1069 (January, 2003).
8) J. A. Wilson et al., *Science* 287, 1664 (2000).
9) S. Shahhosseini et al., *J Virol Methods* 143, 29 (July, 2007).
10) J. S. Yu et al., *J Virol Methods* 137, 219 (November, 2006).
11) V. E. Volchkov, H. Feldmann, V. A. Volchkova, H. D. Klenk, *Proc Natl Acad Sci USA* 95, 5762 (1998).
12) S. A. Jeffers, D. A. Sanders, A. Sanchez, *J Virol* 76, 12463 (December, 2002).
13) J. E. Lee, E. O. Saphire, *Future Virology* in press, (2009).
14) W. Weissenhorn et al., *Mol Membr Biol* 16, 3 (1999).
15) A. Sanchez, *J. Infect. Dis.* 196, S251 (2007).
16) K. Chandran, N. J. Sullivan, U. Felbor, S. P. Whelan, J. M. Cunningham, *Science* 308, 1643 (2005).
17) K. Schornberg et al., *J Virol* 80, 4174 (2006).
18) C. J. Empig, M. A. Goldsmith, *J. Virol.* 76, 5266 (2002).

19) D. Dube et al., *Journal of Virology* 83, 2883 (2009).
20) J. E. Lee, E. O. Saphire, *Current Opinion in Structural Biology* 19, 1 (2009).
21) J. E. Lee, M. L. Fusco, E. O. Saphire, *Nature Protocols* 4, 592 (2009).
22) G. Simmons, R. J. Wool-Lewis, F. Baribaud, R. C. Netter, P. Bates, *J Virol* 76, 2518 (2002).
23) Z. Y. Yang et al., *Nat Med* 6, 886 (2000).
24) R. L. Kaletsky, G. Simmons, P. Bates, *J Virol* 81, 13378 (December, 2007).
25) J. E. Lee et al., *Nature* 474, 177 (2008).
26) D. R. Burton, E. O. Saphire, P. W. Parren, *Curr Top Microbiol Immunol* 260, 109 (2001).
27) P. D. Kwong, I. A. Wilson, *Nat Immunol* 10, 573 (June, 2009).
28) D. C. Ekiert et al., *Science* 324, 246 (2009).
29) A. Takada et al., *Proc Natl Acad Sci USA* 94, 14764 (1997).
30) P. Halfmann et al., *Proc Natl Acad Sci USA* 105, 1129 (Jan. 29, 2008).
31) J. Sui et al., *Nat Struct Mol Biol* 16, 265 (March, 2009).
32) M. C. Lawrence, P. M. Colman, *J Mol Biol* 234, 946 (1993).
33) J. E. Lee et al., *J Mol Biol* 375, 202 (2008).

What is claimed is:

1. An isolated monoclonal antibody comprising a heavy chain variable region having at least 90% sequence identity to the amino acid sequence of SEQ ID NO: 8 and a light chain variable region having at least 90% sequence identity to the amino acid sequence of SEQ ID NO: 10,
- wherein the monoclonal antibody binds Ebola Sudan Boniface virus (ESB) glycoprotein (GP);
- wherein the heavy chain variable region comprises amino acid residues Glu23, Val24, and Lys99, of the amino acid sequence of SEQ ID NO: 8;
- wherein the heavy chain variable region comprises:
  - a CDR1 comprising amino acid residues 48-55 of SEQ ID NO: 8;
  - a CDR2 comprising amino acid residues 73-80 of SEQ ID NO: 8; and
  - a CDR3 comprising amino acid residues 119-130 of SEQ ID NO: 8; and
- wherein the light chain variable region comprises:
  - a CDR1 comprising amino acid sequence of SEQ ID NO: 23;
  - a CDR2 comprising amino acid sequence of SEQ ID NO: 24; and
  - a CDR3 comprising amino acid sequence of SEQ ID NO: 25.

2. The isolated monoclonal antibody of claim 1, which monoclonal antibody comprises a heavy chain variable region having the amino acid sequence of SEQ ID NO: 8 and a light chain variable region having the amino acid sequence of SEQ ID NO: 10.

3. A composition comprising the isolated monoclonal antibody of claim 1.

4. The composition of claim 3, further comprising a pharmaceutically acceptable excipient.

5. A method for inhibiting the replication of ESB in a mammal, comprising administering the composition of claim 3 to the mammal in an amount effective to ESB replication.

6. The method of claim 5, wherein the composition further comprises a pharmaceutically acceptable excipient.

7. A method for detecting ESB virus in a sample, the method comprising:
  (a) incubating the sample with an effective amount of the isolated monoclonal antibody of claim 1 under conditions that allow for the formation of an antibody-ESB virus complex;
  (b) removing unbound antibody; and
  (c) detecting the antibody-ESB virus complex, wherein the presence or absence of the complex indicates the presence or absence of ESB virus in the sample.

8. A kit for detecting ESB virus in a biological sample, the kit comprising:
  (a) a container holding the isolated monoclonal antibody of claim 1, and
  (b) instructions for using said monoclonal antibody to form an immunological complex with ESB virus and to detect the formation of the immunological complex, such that the presence or absence of the immunological complex correlates with presence or absence of ESB in the sample.

* * * * *